US008961426B2

(12) United States Patent
Martin et al.

(10) Patent No.: US 8,961,426 B2
(45) Date of Patent: *Feb. 24, 2015

(54) METHOD AND APPARATUS FOR CONTROL OF NON-INVASIVE PARAMETER MEASUREMENTS

(75) Inventors: Gregory J. Martin, Carlsbad, CA (US); Gregory I. Voss, Solana Beach, CA (US); Manouchehr Goharlaee, Encinitas, CA (US); Stuart L. Gallant, San Diego, CA (US); Warren Craycroft, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 305 days.
This patent is subject to a terminal disclaimer.

(21) Appl. No.: 13/180,315

(22) Filed: Jul. 11, 2011

(65) Prior Publication Data
US 2011/0263991 A1 Oct. 27, 2011

Related U.S. Application Data

(60) Continuation of application No. 11/982,975, filed on Nov. 5, 2007, now Pat. No. 7,976,471, which is a division of application No. 10/393,660, filed on Mar. 20, 2003, now Pat. No. 7,291,112, which is a continuation-in-part of application No. 10/211,115, filed on Aug. 1, 2002, now Pat. No. 6,974,419.

(51) Int. Cl.
*A61B 5/02* (2006.01)
*A61B 5/00* (2006.01)
*A61B 5/021* (2006.01)

(52) U.S. Cl.
CPC .............. *A61B 5/021* (2013.01); *A61B 5/7207* (2013.01); *A61B 5/0048* (2013.01); *A61B 5/7285* (2013.01); *A61B 5/7264* (2013.01)
USPC ........................................................ 600/500

(58) Field of Classification Search
USPC .................................................. 600/481–507
See application file for complete search history.

(56) References Cited

U.S. PATENT DOCUMENTS 3,880,145 A 4/1975 Blick
4,280,494 A 7/1981 Cosgrove, Jr. et al.
(Continued)

FOREIGN PATENT DOCUMENTS

JP 2177937 7/1990
JP 3007139 1/1991

OTHER PUBLICATIONS

Clinical Cardiology article entitled "Apparent Bigeminy and Pulsus Alternans in Intermittent Left Bundle-Branch Block" by Laszlo Littman, M.D. and Jeffrey R. Goldberg, M.D., Departments of Internal Medicine and Family Practice, Carolinas Medical Center. Charlotte, NC (Jun. 1999) ( 3 pages) (www.clinicalcardiology.org).
(Continued)

*Primary Examiner* — Michael Kahelin
*Assistant Examiner* — Karen Toth
(74) *Attorney, Agent, or Firm* — Gazdzinski & Associates, PC

(57) ABSTRACT

Improved methods and apparatus for non-invasively assessing one or more parameters associated with fluidic systems such as the circulatory system of a living organism, when such parameters are potentially affected by other concurrent events. In one exemplary embodiment, apparatus and methods for compensating for occlusive events (e.g., pressure cuff inflation) occurring ipsilateral to the location of parameter measurement are disclosed. Upon passive detection of signal degradation resulting from the event, the apparatus selectively enters a "wait state" wherein further processing of the hemodynamic data is suspended until the degrading event subsides. This behavior mitigates any adverse effects the event might have on the accuracy of the representation of the measured hemodynamic parameter generated by the system. In another exemplary embodiment, the measured data is analyzed in order to classify the type of event (e.g., occlusive or other), such classification allowing the system to appropriately tailor its response to the event.

12 Claims, 37 Drawing Sheets

(56) References Cited

U.S. PATENT DOCUMENTS

| | | | | |
|---|---|---|---|---|
| 4,539,997 | A | * | 9/1985 | Wesseling et al. ............ 600/480 |
| 4,718,427 | A | | 1/1988 | Russell |
| 4,869,261 | A | | 9/1989 | Penaz |
| 4,880,013 | A | | 11/1989 | Chio |
| 5,094,244 | A | | 3/1992 | Callahan et al. |
| 5,119,822 | A | | 6/1992 | Niwa |
| 5,261,414 | A | * | 11/1993 | Aung et al. .................. 600/496 |
| 5,322,069 | A | | 6/1994 | Gallant et al. |
| 5,329,931 | A | | 7/1994 | Clauson et al. |
| 5,533,511 | A | | 7/1996 | Kaspari et al. |
| 5,649,542 | A | | 7/1997 | Archibald et al. |
| 5,680,869 | A | | 10/1997 | Ogura |
| 5,755,670 | A | | 5/1998 | McKown et al. |
| 5,797,850 | A | | 8/1998 | Archibald et al. |
| 5,833,602 | A | | 11/1998 | Osemwota |
| 5,848,970 | A | | 12/1998 | Voss et al. |
| 5,882,311 | A | | 3/1999 | O'Rourke |
| 5,908,027 | A | | 6/1999 | Butterfield et al. |
| 5,964,711 | A | | 10/1999 | Voss et al. |
| 6,047,201 | A | | 4/2000 | Jackson, III |
| 6,068,601 | A | | 5/2000 | Miyazaki |
| 6,176,831 | B1 | | 1/2001 | Voss et al. |
| 6,228,034 | B1 | | 5/2001 | Voss et al. |
| 6,270,461 | B1 | | 8/2001 | Chio |
| 6,290,650 | B1 | | 9/2001 | Butterfield et al. |
| 6,322,516 | B1 | | 11/2001 | Masuda et al. |
| 6,334,850 | B1 | | 1/2002 | Amano et al. |
| 6,340,349 | B1 | | 1/2002 | Archibald et al. |
| 6,371,921 | B1 | * | 4/2002 | Caro et al. .................. 600/485 |
| 6,554,773 | B1 | | 4/2003 | Nissila et al. |
| 6,554,774 | B1 | | 4/2003 | Miele |
| 6,612,993 | B2 | | 9/2003 | Narimatsu |
| 6,632,181 | B2 | | 10/2003 | Flaherty et al. |
| 6,711,424 | B1 | | 3/2004 | Fine et al. |
| 6,730,038 | B2 | | 5/2004 | Gallant |
| 7,048,691 | B2 | * | 5/2006 | Miele et al. .................. 600/504 |
| 7,291,112 | B2 | * | 11/2007 | Martin et al. ................. 600/485 |
| 7,976,471 | B2 | * | 7/2011 | Martin et al. ................. 600/490 |
| 2002/0038090 | A1 | * | 3/2002 | Sunagawa et al. ............ 600/485 |
| 2002/0055680 | A1 | | 5/2002 | Miele et al. |

OTHER PUBLICATIONS

Article entitled "A Fourier Transform Based Tof-Hreels Spectrometer" by R.H. Jackson, L.J. LeGore, Z. Yang, P. Keiban and B.G. Frederick, Laboratory for Surface Science and Technology (LASST) and Dept. of Chemistry, Univ. of Maine, Orono, ME (no date) (1 page/p. O-36).

System Theory and Frequency-Selective Filters (Jun. 20, 2003) G. Baura, (6 pages/pp. 1, 24-28); System Theory and Practical Applications of Biomedical Signals, Wiley-Interscience, A John Wiley & Sons, Inc., Publication (.Copyrgt. 2002).

Article entitled "Dynamic Ventilatory Response to $CO_2$ in Congestive Heart Failure Patients With and Without Central Sleep Apnea" by Zbigniew L. Topor, Linda Johannson, Jerry Kasprzyk and John E. Remmers, Center for Biomedical Engineering, Univ. of Kentucky (accepted Feb. 28. 2001) (9 pages/pp. 408-416) (www.jap.org).

American Journal of Respiratory and Critical Care Medicine, vol. 158, No. 4 article entitled "Instability of Ventilatory Control in Patients with Obstructive Sleep Apnea" by David W. Hudgel, Elizabeth A. Gordon, Sitthep Thanakitchara and Eugene N. Bruce, Case Western Reserve Univ. MetroHealth Medical Center, Cleveland, Ohio (Oct. 1998) (2 pages) (http://ajrcem.atsjournals.org).

American Journal Regulatory Integrative Comp Physiol article entitled "Dynamic Baroreflex Control of Blood Pressure: Influence of the Heart vs. Peripheral Resistance" by Huang-Ku Liu, Sara-Jane Guild, et al., Depts. of Physiology and Electrical and Electronic Engineering, Univ. of Auckland, New Zealand (accepted Mar. 22, 2002) (10 pages/pp. R533-R542) (www.aipregu.org).

Article entitled "Monitoring Vital Signs in Clinical and Research Animals" by Janice M. Bright, Cardiology Consultant, Vetronics, Inc.—Current Separations 16:2 (1997) (4 pages/pp. 43-46).

System Specification for SphygmoCor Pulse Wave Analysis System: Model SCOR-Px (no date) (2 pages) (http://www.pwvmedical.com).

Article entitled "Annals of Internal Medicine Established in 1927 by the American College of Physicians" by M. Chiara Cavallino, MD, et al., vol. 124, Issue 10, (11 pages/pp. 877-883), (May 15, 1996) (http://www.annals.org).

Circulation 1996; 93:2135-2141 article entitled "Randomized, Double-Blind, Placebo-Controlled Study of Supple,mental Oral L-Arginine in Patients With Heart Failure" by Thomas S. Rector, PhD, et al. (pp. 1-5 of 18) (http://circ.ahajournals.org).

Circulation 1996; 93:2135-2141 article entitled "Randomized, Double-Blind, Placebo-Controlled Study of Supplemental Oral L-Arginine in Patients With Heart Failure" by Thomas S. Rector. PhD, et al. (pp. 1-5 of 18) (http://circ.ahajoamals.org).

Clinical Science (1998) 95. 669-679 article entitled "Non-invasive Measurements of Arterial Structure and Function: Repeatability, Interrelationships and Trial Sample Size" by Ye-Lu Liang, et al. (13 pages) (http://www.clinsci.org).

* cited by examiner

METHOD AND APPARATUS FOR CONTROL OF NON-INVASIVE PARAMETER MEASUREMENTS

PRIORITY

This application is a continuation of and claims priority to U.S. patent application Ser. No. 11/982,975 filed Nov. 5, 2007 of the same title, which is a divisional of and claims priority to U.S. patent application Ser. No. 10/393,660 filed Mar. 20, 2003 of the same title, now U.S. Pat. No. 7,291,112, which is a continuation-in-part of and claims priority to U.S. patent application Ser. No. 10/211,115 entitled "METHOD AND APPARATUS FOR CONTROL OF NON-INVASIVE PARAMETER MEASUREMENTS" filed Aug. 1, 2002, each of which is incorporated by reference herein in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to methods and apparatus for monitoring parameters associated with circulating fluid systems, and specifically in one aspect to the non-invasive monitoring of arterial blood pressure in a living subject under varying conditions including concurrent application of a cuff or other occlusive device.

2. Description of Related Technology

The accurate, continuous, non-invasive measurement of blood pressure has long been sought by medical science. The availability of such measurement techniques would allow the caregiver to continuously monitor a subject's blood pressure accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's peripheral (predominately brachial) artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. Note that other measures analogous to maximum pulsatile pressure, including maximum rate of change in pressure (i.e., maximum dP/dT) can also be implemented.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This can result in inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement.

Tonometry systems are also commonly quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Furthermore, compliance in various apparatus components (e.g., the strap and actuator assembly) and the lack of soft padding surrounding the sensor which minimizes edge effects may adversely impact the accuracy of tonometric systems to a significant extent.

One very significant limitation of prior art tonometry approaches relates to the magnitude and location of the applied applanation pressure during varying conditions of patient motion, position, mean pressure changes, respiration, etc. Specifically, even when the optimum level of arterial compression at the optimal coupling location is initially achieved, there are commonly real-world or clinical factors beyond reasonable control that can introduce significant error into the measurement process, especially over extended periods of time. For example, the subject being monitored may voluntarily or involuntarily move, thereby altering (for at least a period of time) the physical relationship between the tonometric sensor and the subject's tissue/blood vessel. Similarly, bumping or jarring of the subject or the tonometric measurement apparatus can easily occur, thereby again altering the physical relationship between the sensor and subject. The simple effect of gravity can, under certain circumstances, cause the relative positions of the sensor and subject blood vessel to alter with time as well.

Furthermore, physiologic responses of the subject (including, for example, relaxation of the walls of the blood vessel due to anesthesia or pharmacological agents) can produce the need for changes in the applanation level (and sometimes even the lateral/proximal position of the sensor) in order to maintain optimal sensor coupling. Additionally, due to the compliance of surrounding tissue and possibly measurement system, the applanation level often needs to adjust with changes in mean arterial pressure.

Several approaches have heretofore been disclosed in attempts to address the foregoing limitations. In one prior art approach, an occlusive cuff is used to provide a basis for periodic calibration; if the measured pressure changes a "significant" amount or a determined time has elapsed, then the system performs a cuff calibration to assist in resetting the applanation position. Reliable pressure data is not displayed or otherwise available during these calibration periods. See for example U.S. Pat. No. 5,261,414 to Aung, et al issued Nov. 16, 1993 and entitled "Blood-Pressure Monitor Apparatus," assigned to Colin Corporation (hereinafter "Aung"). See also U.S. Pat. No. 6,322,516 issued Nov. 27, 2001 and entitled "Blood-Pressure Monitor Apparatus," also assigned to Colin Corporation, wherein an occlusive cuff is used as the basis for calibration of a plurality of light sensors.

In another prior art approach, a pressure cuff or a pelotte equipped with a plethysmographic gauge; such as an impedance or a photo-electric device, is used to drive a servo control loop. See, e.g., U.S. Pat. No. 4,869,261 to Penaz issued Sep. 26, 1989 and entitled "Automatic noninvasive blood pressure monitor," assigned to University J. E. Purkyne v Brne (hereinafter "Penaz"). In this device, the sensor is connected through at least one amplifier and a phase corrector to an electro-pressure transducer. All these components constitute the closed loop of a servo control system which (at least ostensibly) continuously changes the pressure in the cuff and attempts to maintain the volume of the artery at a value corresponding to zero tension across the arterial wall. The servo control system loop further includes a pressure vibration generator, the frequency of vibration being higher than that of the highest harmonic component of blood pressure wave. A correction circuit is also provided, the input of which is connected to the plethysmographic sensor and output of which is provided to correct the setpoint of the servo control system. The Penaz system therefore in effect constantly "servos" (within a cardiac cycle) to a fixed light signal level received from the sensor. Unlike the Colin systems described above, the system continuously displays pressure to the operator. However, the operation of the plethysmographic sensor of Penaz limited the application of this device to a peripheral section of a limb (preferably a finger) where the peripheral pressure, especially under conditions of compromised peripheral circulation, may not accurately reflect aortic or brachial artery pressure. This presents a potentially significant cause of error.

Yet another prior art approach uses a series of varying pressure "sweeps" performed successively to attempt to identify the actual intra-arterial blood pressure. The applanation pressure applied during each of these sweeps is generally varied from a level of arterial undercompression to overcompression (or vice-versa), and the system analyzes the data obtained during each sweep to identify, e.g., the largest pressure waveform amplitude. See, e.g., U.S. Pat. No. 5,797,850 to Archibald, et al issued Aug. 25, 1998 and entitled "Method and apparatus for calculating blood pressure of an artery," assigned to Medwave, Inc. (hereinafter "Archibald"). The system of Archibald is not truly continuous, however, since the sweeps each require a finite period of time to complete and analyze. In practice the sweeps are repeated with minimal delay, one after another, throughout the operation of the device. During applanation mechanism resetting and subsequent sweep operations, the system is effectively "dead" to new data as it analyzes and displays the data obtained during a previous sweep period. This is clearly disadvantageous from the standpoint that significant portions of data are effectively lost, and the operator receives what amounts to only periodic indications of the subject's blood pressure (i.e., one new pressure beat display every 15-40 seconds).

Lastly, the techniques for non-invasive pressure measurement disclosed by the Assignee of the present invention in U.S. Pat. Nos. 6,228,034, 6,176,831, 5,964,711, and 5,848,970, each entitled "Apparatus and method for non-invasively monitoring a subject's arterial blood pressure" and incorporated herein by reference in their entirety, include modulation of applanation level at, inter cilia, frequencies higher than the heart rate (e.g., sinusoidal perturbation at 25 Hz). While the foregoing methods are effective, Assignee has determined over time that it is desirable at certain circumstances to control the applanation level according to other modulation schemes and/or frequencies, and/or which are not regular or deterministic in nature. Furthermore, certain modulation schemes (e.g., intra-beat modulation) can place significant demands on the applanation hardware, since more rapid (and often precise) variations in applanation level must occur. Accordingly, the more capable hardware required in such applications ultimately raises the cost of the parent device in which it is used.

Occlusive Cuff and Tonometric Combinations

Several instances exist where it is desired to use both occlusive cuff or comparable devices in conjunction with tonometric non-invasive pressure devices. Such instances may include, for example, situations where confirmatory checks between the devices are required, and critical situations where redundancy or fault tolerance is required (such as surgery). In many cases, the cuff or other occlusive device is applied "upstream" on the same limb (ipsilateral) as the non-invasive device for any number of reasons including lack of accessibility to the opposite limb, and/or use of an intravenous (IV) apparatus in the other limb (for which continued and non-occluded blood flow is desired). With the occlusion resulting from the application and inflation of a cuff, the volume of the upper limb to which the cuff is applied (e.g., human arm) increases as arterial blood flows into the region while venous return is prohibited. As cuff pressure increases flow (and thereby pulse pressure) ceases and the arterial blood begins to transfer from the arterial tree to the high compliance venous system in the arm. The resultant pressure curve generally approximates an exponentially decaying function wherein the resultant pressure is below diastolic pressure but significantly above central venous pressure. Variations in the performance of the cuff and associated inflation/deflation systems, as well as the patient's anatomy, can influence this decay function. Hence, the tonometric apparatus should ideally be able to determine that an upstream cuff or other occlusive device is in use, and compensate accordingly as required in order to accurately reflect this exponentially decaying pressure signal (or at minimum mitigate the effect of the decaying signal on the accuracy of the blood pressure representation generated by the system).

Based on the foregoing, there is needed an improved methodology and apparatus for accurately and continuously controlling the non-invasive measurement of parameters such as pressure during loss-of-pressure conditions such as those created by inflation of an occlusive cuff. Such improved methodology and apparatus would ideally allow for, inter alga, continuous measurement (tonometrically or otherwise) of one or more hemodynamic parameters, the measured values of such parameters being reflective of true intra-arterial parameters, while also providing robustness during the aforementioned conditions where the signal is temporarily lost or degraded. Such method and apparatus would also ideally be completely passive in the sense that it would not require any external information or input (other than the existing signal) to detect the onset of such events.

SUMMARY OF THE INVENTION

The present invention satisfies the aforementioned needs by improved methods and apparatus for non-invasively and continuously controlling the measurement of parameters in a fluidic system, including arterial blood pressure within a living subject, during conditions where the hemodynamic signal is either degraded or lost.

In a first aspect of the invention, an improved method of measuring blood pressure in a living subject is disclosed, the method generally comprising: measuring pressure from a blood vessel at a first location on the subject; at least partly occluding a blood vessel at a second location on the subject, the act of occluding having at least some effect on the blood pressure measurement; and adjusting the measurement based at least in part on this effect. In one exemplary embodiment, blood pressure is measured tonometrically from an artery (e.g., radial artery), with the second location being ipsilateral thereto; i.e., the upper arm. A cuff inflated at the second location causes decay of the pressure signal sensed by the tonometric pressure sensor, such decay being detected by the system and compensated for by delaying subsequent processing of pressure data until the cuff is deflated.

In a second aspect of the invention, improved blood pressure measuring apparatus, the apparatus generally comprising: a non-invasive pressure sensor adapted for sensing the pressure applied thereto by a blood vessel at a first location on the body of a subject, and generating a signal relating thereto; a processor operatively coupled to the sensor; and a computer program running on the processor and adapted to process the signal to produce a representation of said blood pressure, the program further adapted to (i) detect a loss of pressure event within the signal; and (ii) adjust the processing of the pressure data based on the event. In one exemplary embodiment, the program further comprises a beat detector and a no-beat process, wherein the beat detector advises said no-beat process as to detected beats within the signal, the no-beat process suspending processing if no beats are detected within a given time interval.

In a third aspect of the invention, an improved method of processing blood pressure data is disclosed, comprising: obtaining a first plurality of data corresponding to a first state of operation; obtaining a second plurality of data corresponding to a second state of operation; evaluating the first and second data; and based on this evaluation, selectively adjusting the subsequent processing of blood pressure data. In one exemplary embodiment, obtaining the first data comprises obtaining pressure data during a normal (non-event) state of operation, and obtaining the second data comprises obtaining pressure data during an event which results in at least partial degradation of the pressure data. When the degraded data is present, the system enters a "wait state" where further evaluation is conducted. At least one metric associated with each set of data is evaluated during the wait state, and the system either: (i) exits the wait state, or (ii) continues operating in the wait state for a period of time.

In a fourth aspect of the invention, improved apparatus adapted to generate a representation of the blood pressure the blood vessel of a living subject is disclosed. The representation is generated by tonometrically sensing pressure at a first location using at least one sensor and producing signals relating thereto; passively detecting a degradation of these signals; classifying the degradation based at least in part on the signals; and compensating for the effects of the degradation on the representation of blood pressure.

In a fifth aspect of the invention, improved hemodynamic data processing apparatus, is disclosed, generally comprising: a processor adapted to receive hemodynamic data and process same; a first data storage location adapted to receive at least a first portion of the hemodynamic data; a second data storage location adapted to receive at least a second portion of the hemodynamic data; and a computer program running on the processor, said program adapted to: segregate the data into the first and second portions for storing in the first and second locations, respectively; evaluate the first and second portions based on at least one metric; and control the segregation of subsequent hemodynamic data received by the processor based on the evaluation.

In a sixth aspect, a physiologic parameter measuring apparatus is disclosed. The apparatus is configured to mitigate effects of a first change in blood vessel dynamics. The apparatus includes a non-invasive parameter sensor configured to sense a parameter associated with a blood vessel at a first location on a body of a subject and generate a signal relating thereto, a processor operatively coupled to the sensor, and a computer program configured to be executed by the processor, the computer program comprising a plurality of instructions. When executed, the instructions are configured to: process the signal to produce a representation of the measured parameter, passively detect a second change within the signal resulting from the first change in the dynamics, and delay processing of the signal until the second change has substantially subsided.

In a seventh aspect, a method of mitigating an effect of an alteration within physiologic parameter data obtained from a sensor applied to a living subject is disclosed. The method includes analyzing the data, via a processor, to derive a substantially continuous representation of the physiologic parameter, detecting an event within the physiologic parameter within the signal, suspending the act of analyzing for a predetermined period based at least in part on the act of detecting the event, after expiration of the period, determining whether the event has terminated, and when the event has terminated, re-initiating the act of analyzing.

In an eighth aspect, a physiologic parameter measuring apparatus configured to mitigate an effect of an alteration is disclosed. The apparatus includes a sensor configured to sense a physiologic parameter at a first location on a body of a subject and generate a signal relating thereto, a processor operatively coupled to the sensor, and a computer program configured to be executed by the processor, the computer program comprising a plurality of instructions. The instructions are configured to when executed: analyze the signal to derive a continuous representation of the measured parameter, detect a change within the signal resulting from the alteration, based at least in part on the detected change, suspend the analysis for a predetermined period, determine whether the event has terminated upon expiration of the period, and when the event has terminated, re-initiate the analysis.

These and other features of the invention will become apparent from the following description of the invention, taken in conjunction with the accompanying drawings.

BRIEF DESCRIPTION OF THE DRAWINGS

FIG. 2b is a graph of tonometric pressure versus time for the optimal arterial compression (applanation) of the patient of FIG. 2a.

FIG. 2c is a graph of tonometric pressure versus time for both optimal and non-optimal applanation level applied to the patient of FIG. 2a.

DETAILED DESCRIPTION OF THE INVENTION

Figure 1:
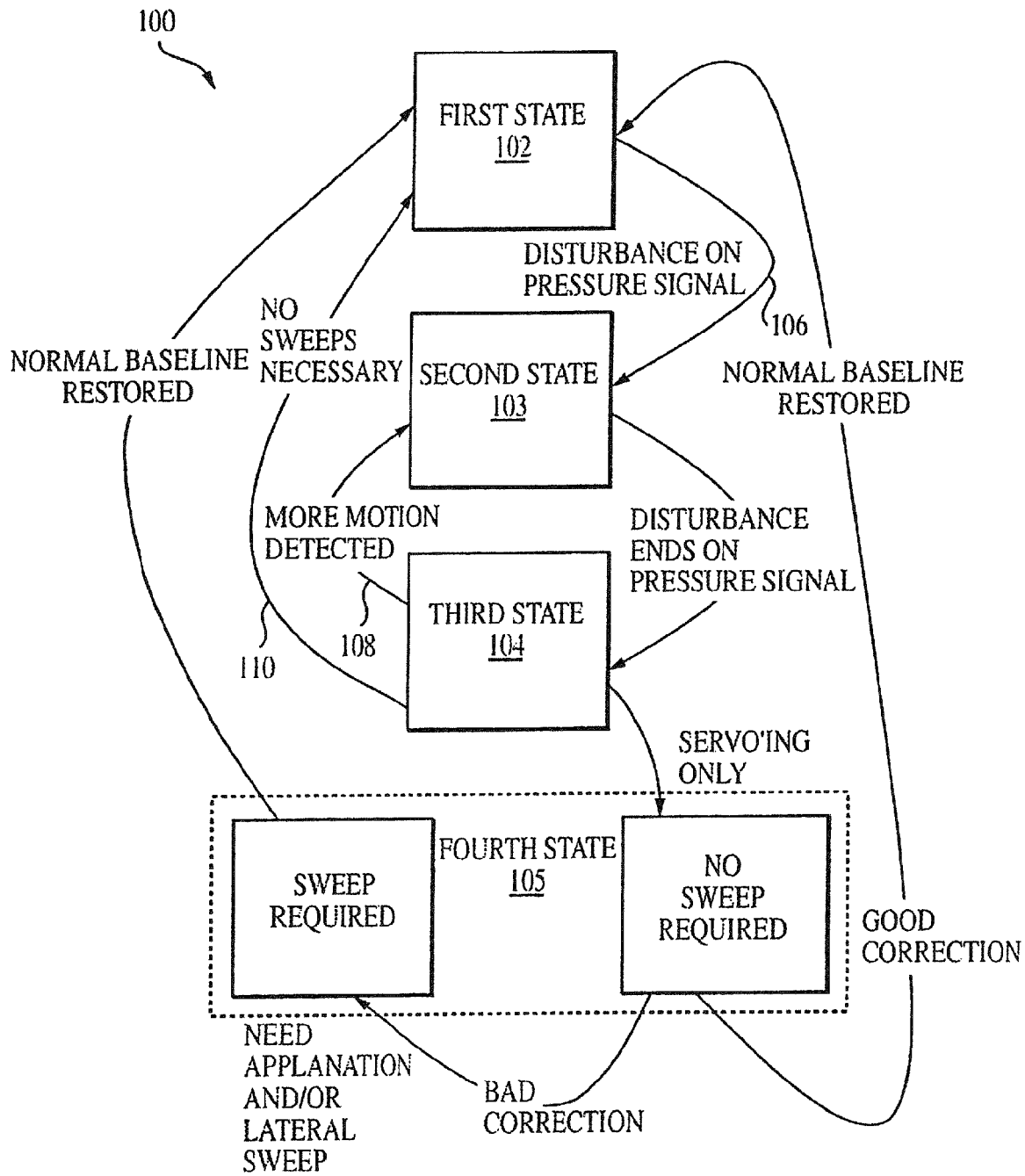
FIG. 1 is a state diagram illustrating the relationship of the four states associated with a first exemplary embodiment of the first process of the present invention.

Reference is now made to the drawings wherein like numerals refer to like parts throughout.

It is noted that while the invention is described herein primarily in terms of a method and apparatus for the control of non-invasive measurements of hemodynamic parameters such as blood pressure obtained via the radial artery (i.e., wrist) of a human subject, the invention may also be readily embodied or adapted to monitor such parameters at other blood vessels and locations on the human body, as well as monitoring these parameters on other warm-blooded species. Similarly, the techniques of the present invention can be applied to other similar fluidic systems which have similar properties to those of the circulatory system of a living being. All such adaptations and alternate embodiments are readily implemented by those of ordinary skill in the relevant arts, and are considered to fall within the scope of the claims appended hereto.

As used herein, the term "hemodynamic parameter" is meant to include parameters associated with the circulatory system of the subject, including for example pressure (e.g., diastolic, systolic, pulse, or mean pressure), derivatives or combinations thereof, arterial flow, arterial wall diameter (and its derivatives), cross sectional area of the artery, and arterial compliance.

Additionally, it is noted that the terms "tonometric," "tonometer," and "tonometery" as used herein are intended to broadly refer to non-invasive surface measurement of one or more hemodynamic parameters, such as by placing a sensor in communication with the surface of the skin, although contact with the skin need not be direct, and can be indirect (e.g., such as through a coupling medium or other interface).

The terms "applanate" and "applanation" as used herein refer to the compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other faults, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"; or (vi) a deterministic profile. All such forms are considered to be encompassed by the term.

As used herein, the term "epoch" refers to any increment of time, ranging in duration from the smallest measurable fraction of a second to more than one second.

As used herein, the terms "spatial" and "position", although described in terms of a substantially Cartesian coordinate system having applanation (i.e., Z-axis), lateral (X-axis) and (Proximal refers to closer to the heart) longitudinal or (proximal-distal) (Y-axis) components, shall refer to any spatial coordinate system including, without limitation, cylindrical, spherical, and polar. Such use of alternate coordinate systems may clearly be independent of any particular hardware configuration or geometry (e.g., by performing simple mathematical translations between a Cartesian-based apparatus and the non-Cartesian coordinate system), or alternatively make advantageous use of such geometries. The present invention is therefore in no way limited to certain coordinate systems of apparatus configurations. As one example, it will be recognized that the methods and apparatus of the present invention may be embodied using a cylindrical coordinate system modeled around the radial artery, such that a particular point in space for the tonometric sensor(s) can be specified by the Z, r, and $\theta$ parameters. This approach may have advantages since the forearm/wrist area of the human being very roughly comprises a cylindrical form.

Lastly, the term "digital processor" is meant to include any integrated circuit or other electronic device (or collection of devices) capable of performing an operation on at least one instruction including, without limitation, reduced instruction set core (RISC) processors such as those manufactured by ARM Limited of Cambridge, UK, CISC microprocessors, microcontroller units (MCUs), CISC-based central processing units (CPUs), and digital signal processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Overview

In one fundamental aspect, the present invention comprises methods and apparatus for controlling an applanation or other positioning mechanism used in non-invasive hemodynamic parameter measurements in order to, inter alia, maintain optimal coupling between a parameter sensor and the blood vessel of interest Techniques for determining the optimal applanation level, position, and coupling are described in detail in, e.g., co-pending U.S. patent application Ser. No. 10/072,508 entitled "Method And Apparatus For Non-Invasively Measuring Hemodynamic Parameters Using Parametrics" filed Feb. 5, 2002, which is assigned to the Assignee hereof and incorporated by reference herein in its entirety.

While the techniques described in the aforementioned co-pending patent application have been determined by Assignee to be highly effective, their robustness and utility in practical (e.g., clinical) settings is enhanced through the addition of one or more of the various aspects of the present invention. Such additional robustness is highly desirable, since it effectively removes many operational restrictions on a clinician, caregiver, or user (hereinafter "operator") when measuring hemodynamic parameters such as blood pressure. Specifically, the operator is substantially relieved of having to monitor the signal derived from the measurement apparatus to detect anomalies, motion artifact, and under certain circumstances will even identify to the operator when error conditions which cannot be corrected have in fact occurred.

After the applanation and lateral (and proximal, if desired) positions that provide the optimal mechanical coupling between the system sensor and the underlying blood vessel have been determined, the invention of the present disclosure is used to control and adjust the level of applanation and/or the lateral/proximal positions to maintain the optimal coupling under potentially adverse environmental conditions such as might be encountered in the average clinical setting. Due to the nature of the clinical setting and all of its variables, not every environmental condition or influence can always be compensated for, and hence the present invention has as another function the ability to identify conditions where changes in mechanical coupling have impacted the accuracy or reliability of hemodynamic measurements in a meaningful manner.

Three separate but substantially interactive processes are used in the present invention to provide the aforementioned control and identification functionalities: (i) a first process adapted to identify sudden changes in the mechanical coupling, as indicated for example by changes in the measured parameter (such as tonometrically measured pressure or pressure velocity) that exceed expected norms, and reacquire either/both the optimal applanation level or lateral/proximal positions where appropriate; (ii) a second process adapted to continuously identify time varying changes in compression coupling, and controllably adjust the applanation position accordingly ("servoing"); and (iii) a third process adapted to operate interactively with the first state and provide warning and protection against loss of optimal coupling in one or more domains, as well as performing a new determination(s) of optimal position in an optimized fashion.

The techniques and apparatus of the present invention may be used with a single sensor (or array of sensors) as described in detail herein and the aforementioned and incorporated co-pending application, or in conjunction with literally any type of other apparatus adapted for hemodynamic parameter measurement, including for example the devices described in co-pending U.S. patent application Ser. No. 09/815,982 entitled "Method and Apparatus for the Noninvasive Assessment of Hemodynamic Parameters Including Blood Vessel Location" filed Mar. 22, 2001, and Ser. No. 09/815,080 entitled "Method and Apparatus for Assessing Hemodynamic Parameters within the Circulatory System of a Living Subject" also filed Mar. 22, 2001, both of which are assigned to the assignee hereof and incorporated herein by reference in their entirety. For example, ultrasound measurements of blood pressure via blood flow kinetic energy or velocity can be used as a confirmatory technique for a fundamentally tonometric pressure-based approach. As another example, lateral positioning based on analysis of the acoustic signals relating to vessel wall detection may be used in addition to (or in place of) the pressure-based techniques described in the originally cited co-pending patent application. Hence, the various aspects of the present invention are advantageously compatible with a number of different hemodynamic assessment techniques. It will also be recognized that the techniques and apparatus described herein are in no way limited to tonometric applications; rather, these features may be implemented even in occlusive cuff or pellot-based systems.

Since signals under measurement (e.g. pressure) are time variant, iteration and optimization are substantially used by the methodology of the present invention to account for this variation. Specifically, the pressure signal associated with a blood vessel is time variant over the short period of the cardiac cycle, over the longer period of the respiratory cycle, and potentially over the even longer or shorter period of hemodynamic changes resulting from varying drug concentrations and volume changes. Accordingly, the three processes referenced above utilize the aforementioned applanation and lateral/proximal positioning mechanisms to continually find and maintain the optimal position and level of applanation, thereby maintaining an environment conducive for accurate, continuous, and non-invasive parametric measurement. In those very limited circumstances where such optimal position and level cannot be reasonably or reliably maintained (such as an abrupt and jarring dislocation of the apparatus from the subject's anatomy), the present invention identifies such conditions accordingly, and optionally alerts the operator or provides other notification.

Table 1 below summarizes the functionality and features of one exemplary embodiment of the invention incorporating the three aforementioned processes.

TABLE 1

| Feature | First Process | Second Process | Third Process |
|---|---|---|---|
| Detection Time Frequency of Changes | >5 Hz | All Frequencies | >20 Seconds |
| Recovery Method | Applanation Sweep | Continuous Adjustment | Applanation Sweep |
| Time to Recover | 10-20 seconds (Largely Uncorrelated to Magnitude of error) | 20-120 seconds (Correlated to Magnitude of error) | 10-20 seconds (Largely Uncorrleated to Magnitude of error) |
| Lateral/Proximal Search | Posssible | No | No |
| Pressure Display Continuous | No: Recovery Sweeps | Yes | No: Recovery Sweeps |

Description of First Process

Figure 1A:
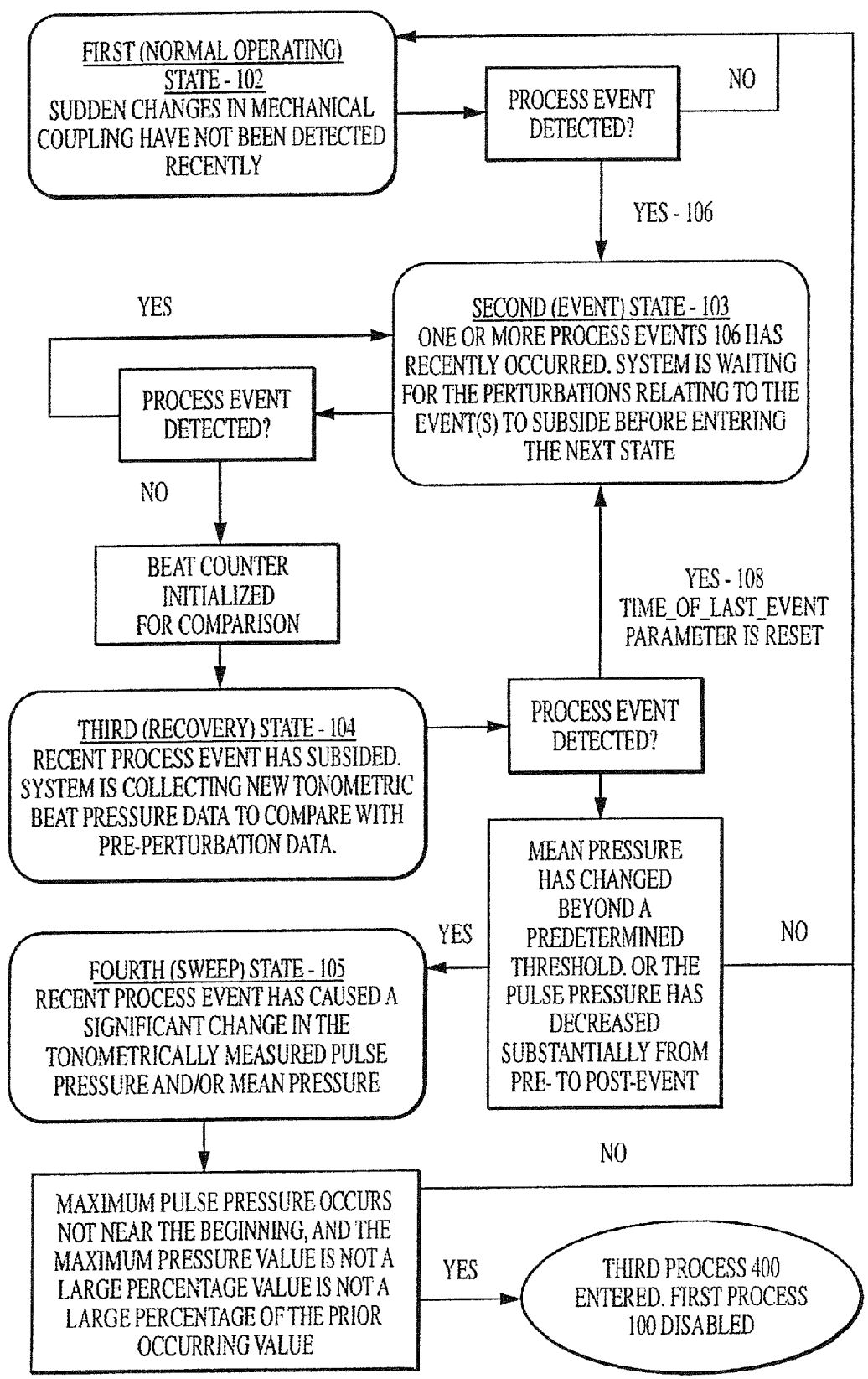
FIG. 1a is logical flow diagram illustrating the operation of the exemplary embodiment of the first process of FIG. 1.

Referring now to FIG. 1-1a, a first exemplary embodiment of the method of identifying sudden changes in the mechanical coupling and reacquisition of either/both the optimal applanation level or lateral/proximal positions according to the invention is described in detail. A detailed discussion of the electronic and signal processing apparatus used to support the operation of the processes described herein is provided with respect to FIG. 5a-5d below. It will be appreciated that while portions of the following discussion are cast in terms of applanation (and lateral/proximal positioning) motors of the stepper-type, the techniques of the present invention may be utilized in conjunction with other types of applanation and positioning apparatus, and accordingly are in no way limited to the specific embodiments of apparatus described herein.

It will also be recognized that while the first process is described subsequently herein with respect to a tonometric pressure transducer, the methodology of the invention can be applied more generally to other signal domains. For example, sudden changes in the mechanical coupling of an ultrasonic transducer to a subject's tissue can be identified using, inter alia, parameters which exceed physiological norms as indicia thereof or measureable distortion in the measurement process. Sudden changes in mechanical coupling will alter the measurement of many parameters, both physiological in nature and otherwise.

Furthermore, it will be appreciated that while described in the context of the aforementioned apparatus (i.e., a tonometric pressure sensor which also acts to provide varying levels of compression of the underlying tissue and blood vessel(s)), the methodology of the present invention may be practiced using apparatus having separate components which provide these functions. For example, the control of the pressure sensor may be partly or completely decoupled from the applanation control system, such that the level of applanation can be varied independently from the coupling of the active surface(s) of the sensor.

The first process of the present embodiment continuously checks for (sudden) changes in the mechanical coupling between a tonometric pressure sensor and the underlying vessel/tissue. Sudden changes in mechanical coupling can be identified by corresponding sudden changes in tonometrically derived pressure $P_T$ (first or second derivative of pressure) that exceed physiologic norms. A velocity parameter, Vp[k], is calculated as in Eqn. 1:

$$P_T[k] - P_T[k-3]$$ (Eqn. 1)

where k represents the current sample, k–3 represents three samples in the past where the sample rate is 160 Hz. Tonometrically measured acceleration, Ap[k], is calculated as in Eqn. 2:

$$Vp[k]-Vp[k-1]=P_T[k]+P_T[k-4]-(P_T[k-1]+P_T[k-3]) \quad \text{(Eqn. 2)}$$

For each sample the pressure, velocity and acceleration are compared with fixed (or deterministic) thresholds. If any one of these parameters exceeds their respective thresholds, then a process "event" is triggered. Note that the pressure, velocity, and acceleration are typically greater during the systolic pressure upstroke than during the diastolic pressure downstroke, hence the thresholds of the present embodiment are set accordingly, providing effectively a "buffer" between physiologic norms and process event triggers. This buffer enhances system robustness, in that trigger events occurring at physiologic norms are avoided.

For example, the ranges of velocity and acceleration of a patient's blood pressure should fall within some limits around zero (generally not symmetric). Changes in mechanical coupling could also be observed as changes (velocity or acceleration) in tonometrically observed pressure. The first process 100 focuses on those changes in mechanical coupling that are both comparatively large and rapid, thus producing velocity or acceleration values that are not realizable from the patient's arterial pressure alone. The buffer of the present embodiment comprises that "cushion" between the range of measurable velocity and acceleration that is naturally occurring (from patient's arterial pressure) and the trigger threshold for the first process 100. It will be recognized, however, that such buffer or cushion may be at least partly obviated through use of one or more sensors that specifically measure changes in mechanical coupling, such as for example a pad sensor, which would allow the system to identify and possibly respond to smaller changes and/or lower frequency changes in mechanical coupling.

When sudden changes in mechanical coupling are detected, tonometric pressure data are compared for periods occurring before and after the process event. For instance, if the pulse pressure (defined for the present discussion as the difference between systolic and diastolic pressures) decreases from the maximum, or the mean pressure changes significantly, then a limited scope pressure sweep is implemented to achieve the optimal applanation. If, despite this pressure sweep, a comparable pulse pressure is not achieved, then a reacquisition state (described in greater detail below) must be entered.

Note that in the present embodiment, the first process is active except in conditions where the system initialization, initial lateral search and applanation sweeps are being performed or when operating in the aforementioned reacquisition state. The second process is also active at the same time as the first process, except in conditions where the first process is performing the limited scope pressure sweep as previously described. It will also be noted that during the limited scope pressure sweep, the current value of $P_T$ is not displayed. Excessive periods, where the current $P_T$ is not available limits the clinical utility of the device, as previously described herein with respect to the prior art. Thus, the present invention minimizes the need for the limited scope pressure sweeps invoked by a process event, thereby improving the overall performance and continuity of the technique over prior art solutions.

The first process 100 of the present embodiment consists of 4 discrete but related states 102, 103, 104, 105 as illustrated in FIG. 1; (i) first state ("normal operation") 102; (ii) second state ("event") 103; (iii) third state ("recovery") 104; and (iv) fourth state ("sweep") 105. The impact of a process event on the servo control system (described in greater detail below with respect to FIGS. 2 and 5), depends largely on the then-exiting state. Each of these four process states 102-105 are now described in detail.

First (Normal Operation) State—The first state 102 is the initial and default operating state. This state is entered when a sweep completes, or following the detection of a sudden change in mechanical coupling little change was observed between pre- and post-pressure data. If a process event occurs, then the most recent median filtered tonometric mean and pulse pressures are stored for future comparisons. A temporal parameter (e.g., Time_of_Last_Event) is set to zero (units in seconds), and the process state is set to the second state (event). If no process event is detected, the first state (normal operation) is maintained. Note that in the present embodiment, the second process 200 (i.e., servoing, discussed below with respect to FIGS. 2-2i) is active during this first normal operating state 102.

(ii) Second (Event) State—The second or event state 104 indicates that one or more process events 106 has recently occurred, and the system is waiting for the perturbations relating to the event(s) to subside before entering the next state. If a process event occurs then, the temporal parameter (e.g., Time_of_Last_Event) is reset. However, if a sufficient time (i.e., 2 seconds) has elapsed since the last event (as determined by the existing value Time_of_Last_Event), then the beat counter (Beat_Counter) value is initialized for comparisons, and the process is set to the third (recovery) state. The prescribed time delay of the present embodiment advantageously minimizes the risk of corrupted pressure data from being incorporated in the post-process event pressure data. As in the first state described above, the second process (servoing) is active during the second state 103.

(iii) Third (Recovery) State—Entry into this third state 104 indicates that the recent process event has subsided, and the system is collecting new tonometric beat pressure data to compare with pre-perturbation data. Upon exit from the third state 104 and before entering the next state, if a process event occurs, then the Time_of_Last_Event parameter is reset, and the process state is set to the second (event) state 103 per step 108. Otherwise, if a new tonometric beat has been identified then, the system beat counter parameter (e.g., Beat_Counter) is incremented for comparisons, and new mean and pulse pressures are written to the storage device (FIGS. 5a-5d) for subsequent comparisons.

Note that if the beat counter has reached a predetermined threshold value, then a comparison of the tonometric pulse and mean pressures stored both before and after the triggering process event is performed. If, upon performing this comparison, the mean pressure has changed beyond a predetermined threshold, or the pulse pressure has decreased substantially from pre- to post-event, then the state of the process 100 is set to the fourth (i.e., sweep) state 105, the sweep initialization parameter (e.g., Initialize_Sweep) is set to "true", and the second process (servoing) is disabled. The motor position parameter (e.g., Motor_Position) is accordingly set to a target motor position value. Target motor position in the illustrated exemplary embodiment is set to either 0 (fully retracted) or –50000 (fully extend out toward the radial artery) where units are motor steps. Target motor position is set to 0 if the post-event mean pressure is greater than the pre-event mean pressure. Target motor position is set to –50000 if the post-event mean pressure is less than the pre-event mean pressure. If the mean pressure has not increased beyond the threshold (and the pulse pressure has not decreased substantially between pre- and post-event), the state of the first process 100 is set to the normal operating (first) state 102 per step 110 of FIG. 1.

If the beat counter has not reached its predetermined threshold, the first process 100 remains in the third (recovery) state 104. As with the first and second states 102, 103 described above, the second (servoing) process 200 remains, in the illustrated embodiment, active during the recovery state 104.

(iv) Fourth (Sweep) State—Entry into this fourth state 105 indicates that the recent process event has caused a significant change in the tonometrically measured pulse pressure and/or mean pressure. In response, the system performs a limited scope pressure sweep to reset the optimal applanation level. Specifically, if the sweep initialization variable (Initialize_Sweep) is set true, the initial search direction as determined for target motor position in (iii) above, and the applanation motor(s) are moved in the proper direction (ramp continuously in the present embodiment, although other profiles may be used). Additionally, the sweep pressure memory is initialized, and the "first pass" parameter flag (e.g., FirstPass_Flag) is set to "true."

If a new beat has been identified, then the process appends the tonometric pressure data associated with the new beat to that existing in the memory array and the Beat_Counter value is incremented for comparisons. Specifically the data for each beat includes average applanation position, mean tonometrically measured pressure, systolic tonometric pressure, diastolic tonometric pressure, and tonometric pulse pressure (i.e., systolic minus diastolic), which are stored in parameter-specific one dimensional arrays within memory.

If the measured mean pressure has reached its minimum goal and current pulse pressure values (median filtered) are significantly less than maximum pulse pressures (median filtered) observed during the sweep, then additional analysis is performed. Specifically, if the maximum pulse occurred close to beginning of the applanation sweep, and the first pass flag (FirstPass_Flag) equals "true" then the FirstPass_Flag is set to "false", and the applanation motor(s) are moved, e.g., to ramp continuously, in the direction opposite from the prior direction of travel. If the maximum pulse pressure did not occur near the beginning of the sweep, and if the maximum pulse pressure (median filtered) is a large percentage (e.g., 80% or greater in the present embodiment) of that occurring prior to the triggering event then the state of the process 100 is set to the first state 102, and servoing at the maximum pulse pressure is initialized. In the context of the present embodiment, the measured mean pressure reaching its "minimum goal" comprises the median filtered mean pressure at least reaching and searching beyond the pre event trigger mean pressure. Note that this requirement can be dependent on the direction of the search (i.e., whether extending or retracting the sensor); specifically, the median filtered mean pressure is greater than the pre-event trigger mean pressure for the sensor extension case, or less than the pre-event trigger mean pressure for the retraction case.

Figure 4:
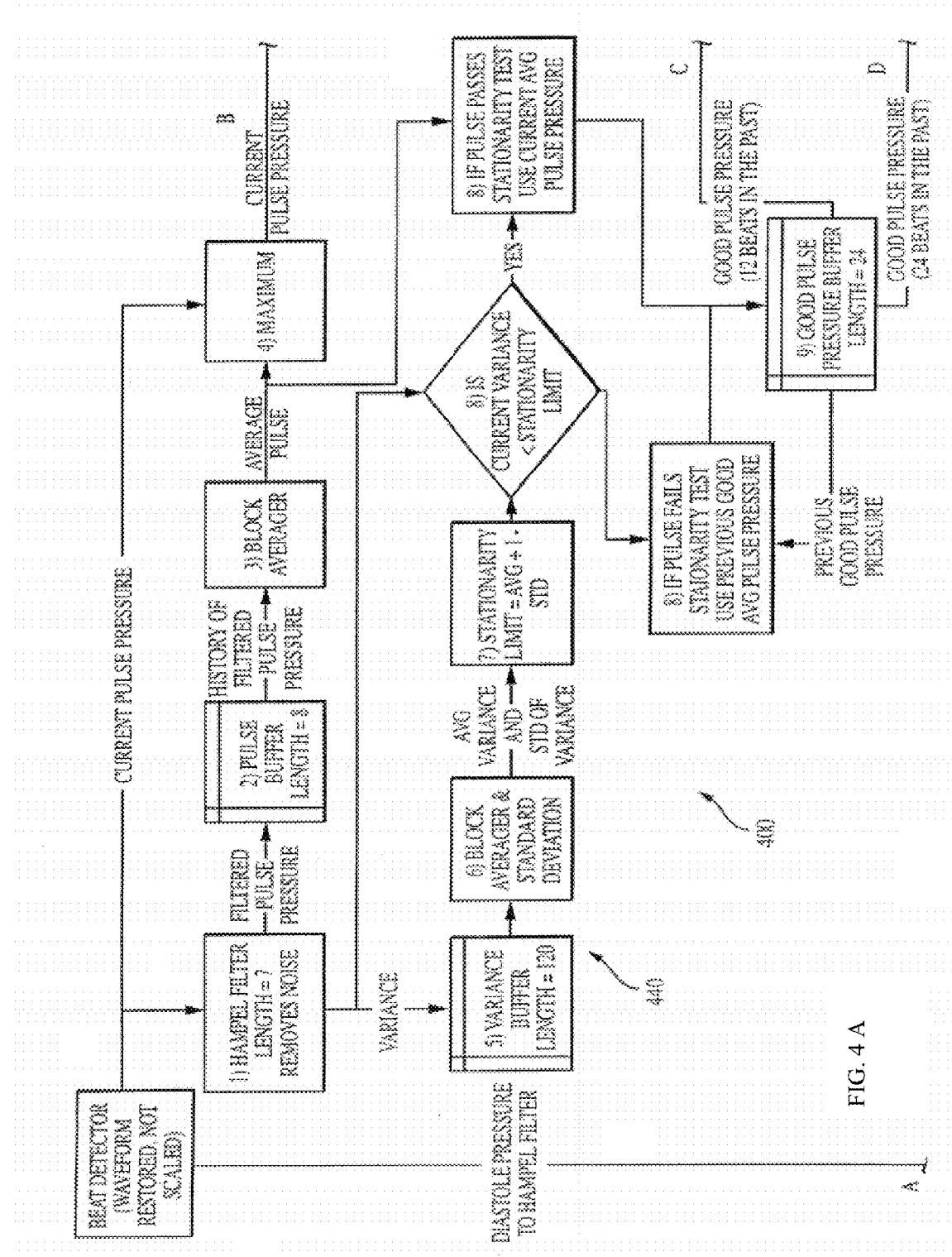
FIG. 4a is a logical flow diagram illustrating the operation of one exemplary embodiment of the third process (e.g., reacquisition) according to the invention.
FIG. 4b is a logical flow diagram illustrating the operation of one exemplary embodiment of the third process (e.g., reacquisition) according to the invention.
FIG. 4c is logical flow diagram illustrating the operation of one exemplary embodiment of the third process (e.g., reacquisition) according to the invention.
FIG. 4d is a graphical illustration of an exemplary embodiment of the fourth ("sweep") state entry criteria associated with the third process of the invention.

However, if the maximum pulse pressure occurs not near the beginning, and the maximum pressure value is not a large percentage of the prior occurring value, then the reacquisition process (the third process 400 discussed below with respect to FIGS. 4a, 4b, 4c) is entered, and the first process 100 is disabled.

It is also noted that second process 200 (FIG. 2) is not active during the fourth state 105 of the first process 100.

FIG. 1a provides a detailed flow chart representation of the exemplary first process 100 of FIG. 1.

It will further be recognized that the first process 100 may be applied to blood pressure measurements irrespective of the mechanism used to originally attain optimal applanation position. In this scenario, the first process operates effectively as if a large transient event had occurred, and uses the foregoing method (in conjunction with the third or reacquisition process 400 described below with respect to FIG. 4a-4c) to settle onto optimal positions for these parameters.

It will be recognized that as referenced above, the first process of the present invention need not operate using a "physiologic" parameter. One exemplary alternative approach of the present invention is to apply and accelerometer or force transducer of the type well known in the art on or contiguous with the sensor surface; i.e., not necessarily over the blood vessel of interest itself. Similarly, such accelerometer or transducer may be located on the apparatus coupling the sensor to the patient (e.g., wrist brace or strap), or alternatively on the shaft (not shown) between the actuating mechanism and the sensor/pad (or within the actuating mechanism itself). Since the first process of the present invention fundamentally detects rapid motion corresponding to potential mechanical coupling disruptions, literally any physical configuration and/or parameter which provides information relating to such motion and disruptions may be used consistent with the invention. As yet another alternative embodiment, an optical sensor of the type well known in the electronic arts may be positioned near the skin and accordingly used as the mechanism to detect sudden changes in sensor/patient relative position.

It can be appreciated that the use of the tonometric pressure sensor as the basis for measurement of the physical parameter (as described in detail above with respect to the exemplary embodiment) provides the benefits of both simplicity and reduced cost by eliminating the need for an added sensor or added complexity of the actuating mechanisms. However, certain benefits relating to the decoupling of the parameter signal from the arterial pressure signal (as compared to the use of the tonometric pressure signal as described above) may be realized through use of one of the alternate embodiments set forth above. For example, use of a non-hemodynamic parameter allows for the separation of mechanical coupling changes from the physiologic signal, since no (or at least minimal) physiologic content exists in the measurements obtained in this fashion. Furthermore, the use of non-physiologic parameter (e.g., pad force or pressure as measured by the force on the applanation motor shaft as described above) allows the use of a much smaller buffer zone, since there is effectively no overlap in the frequency and amplitude of the pressure signal as measured by the pad relative to the pressure changes induced by disruptions in mechanical coupling.

Description of Second Process

Figure 2:
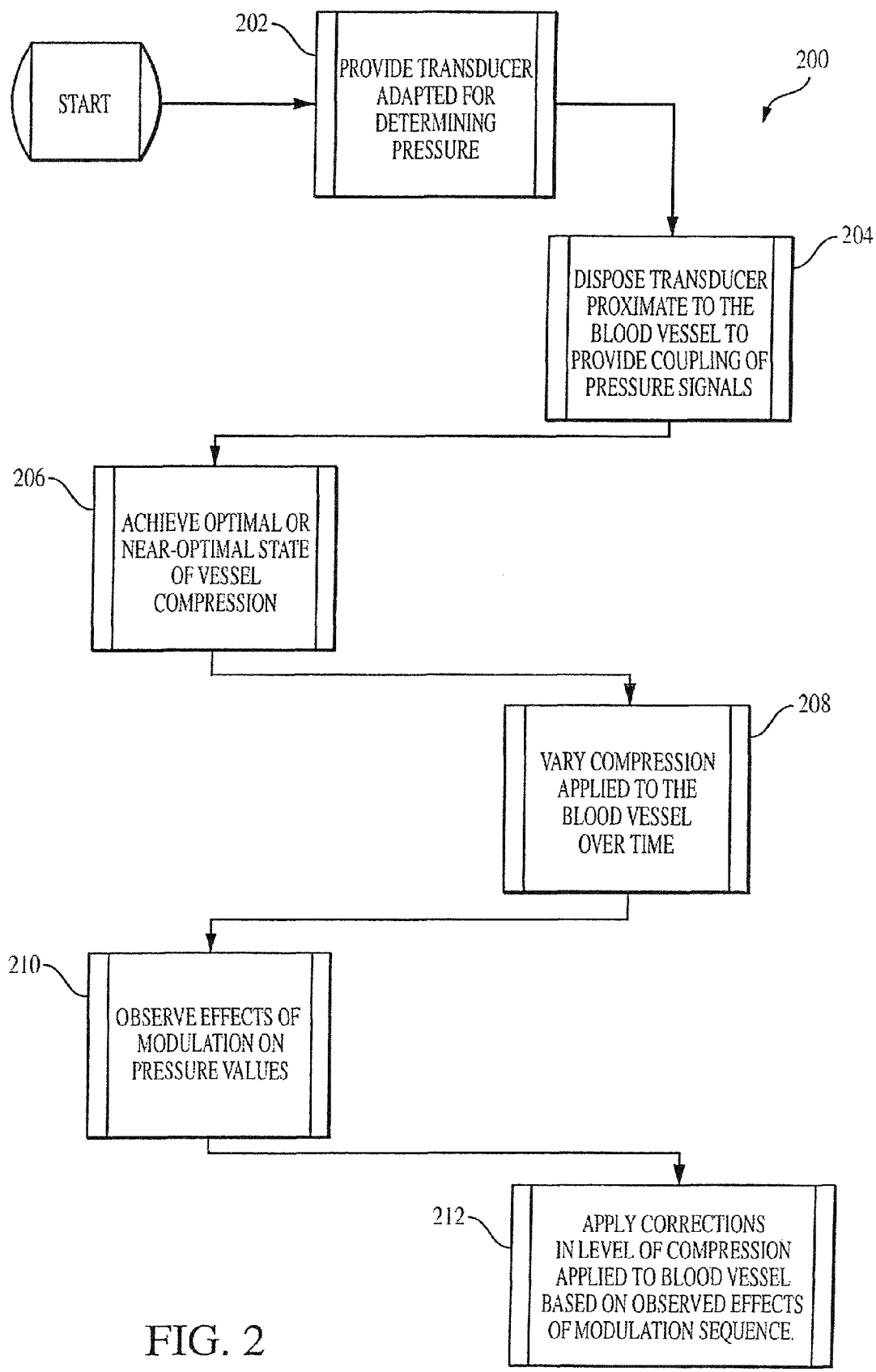
FIG. 2 is logical flow diagram illustrating the operation of one exemplary embodiment of the second process (e.g., servoing or maintaining optimal applanation level) according to the invention.
Figure 2A:
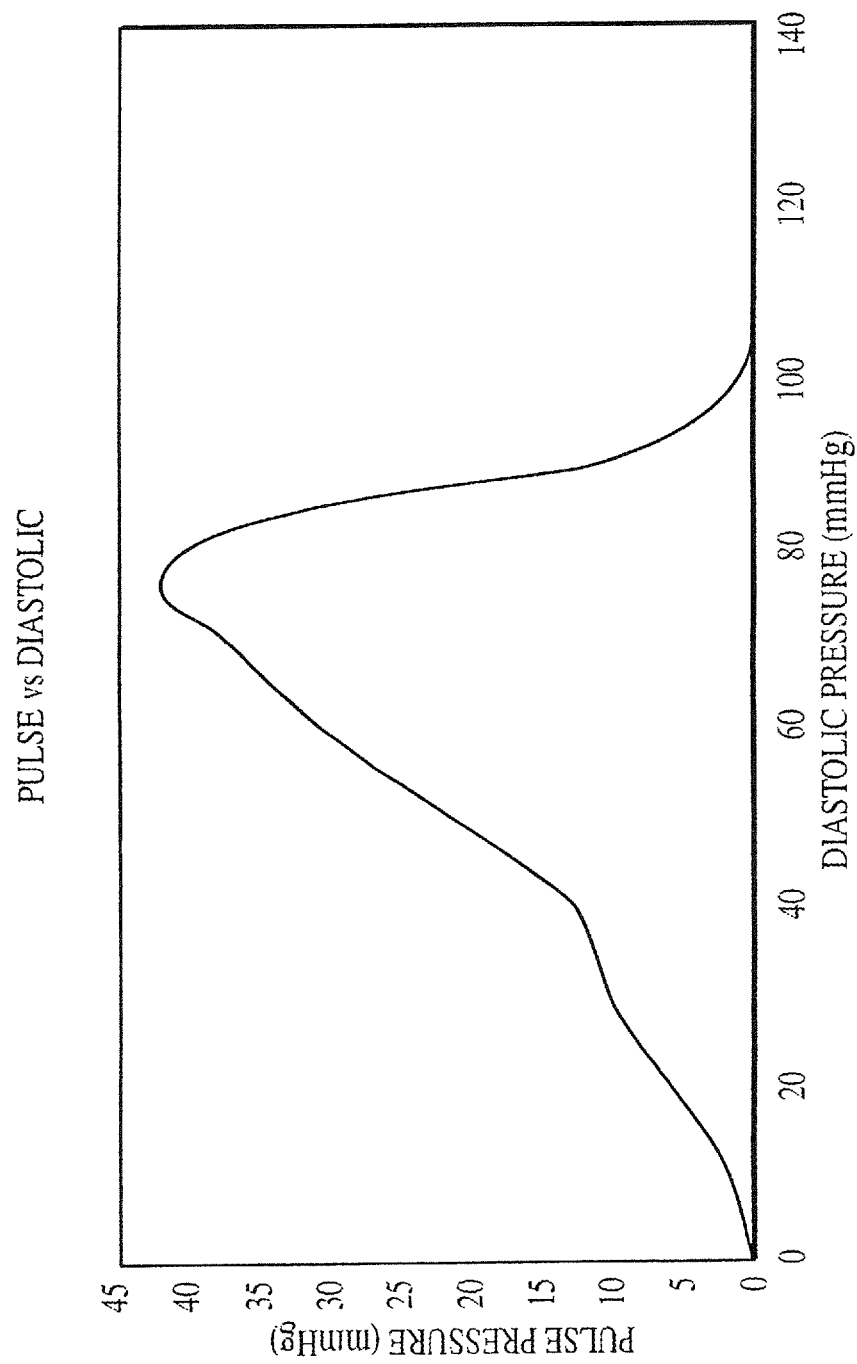
FIG. 2a is a graph of pulse pressure versus diastolic pressure for an exemplary patient.
Figure 2B:
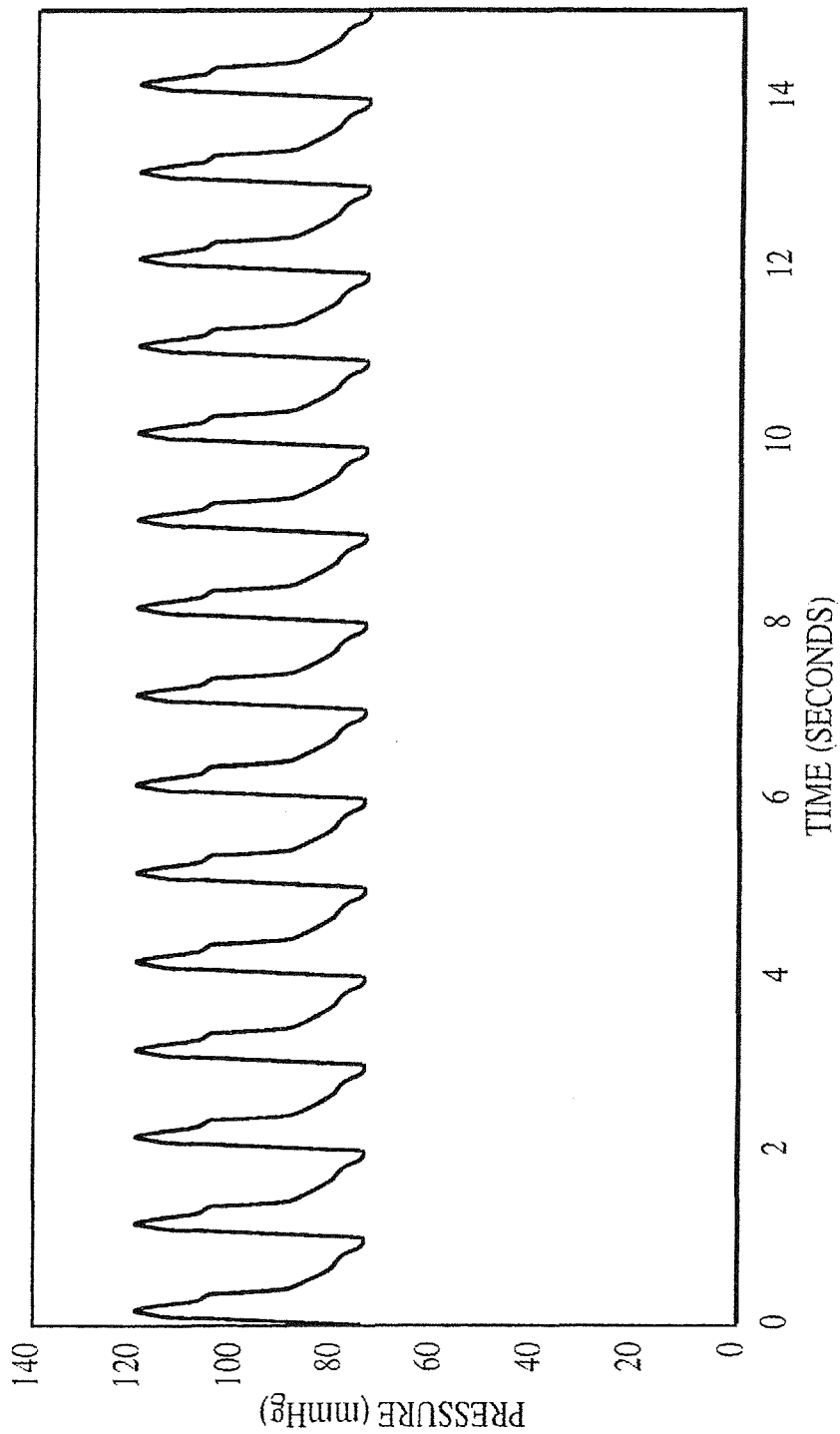
Figure 2C:
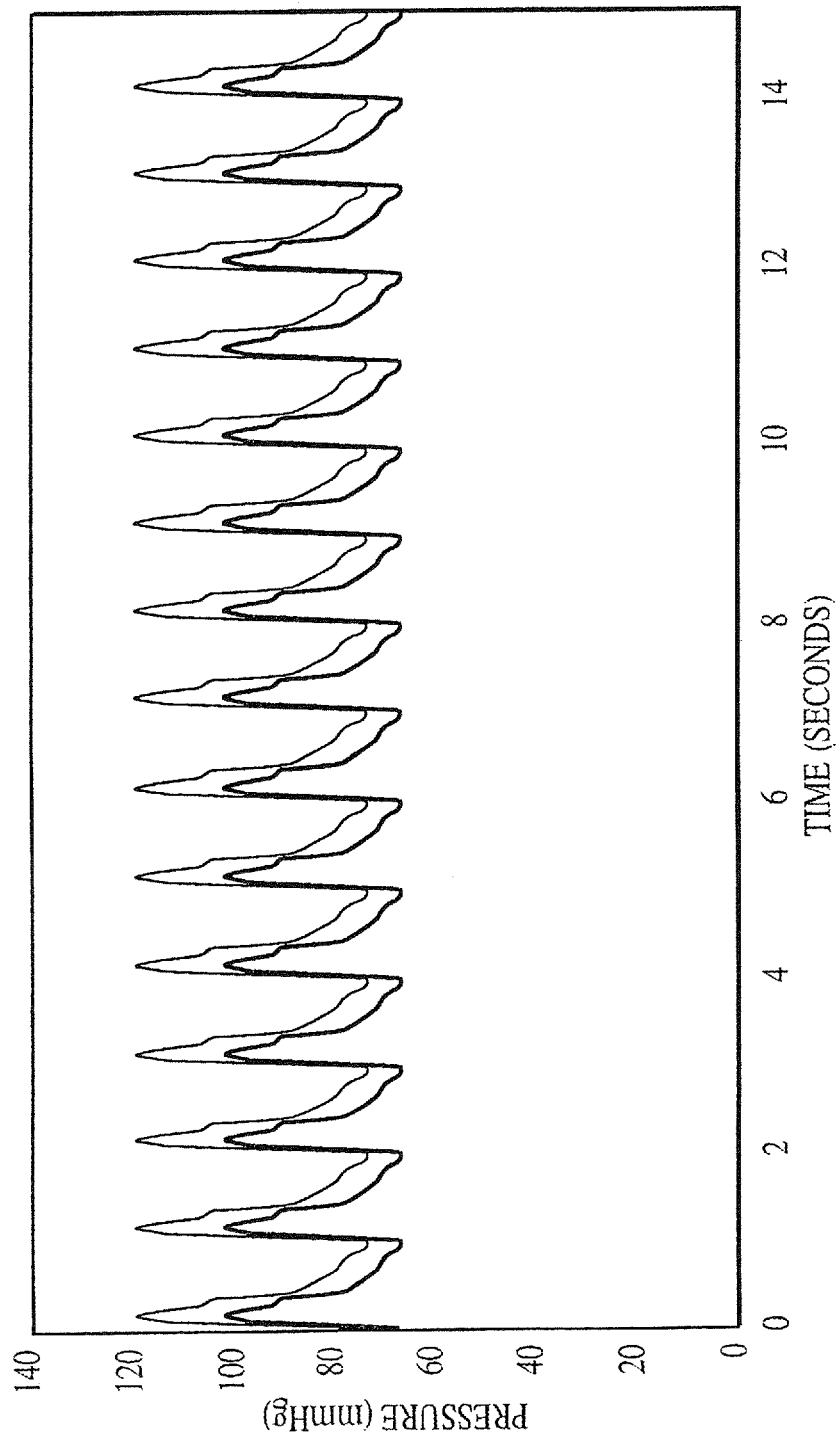
Figure 2D:
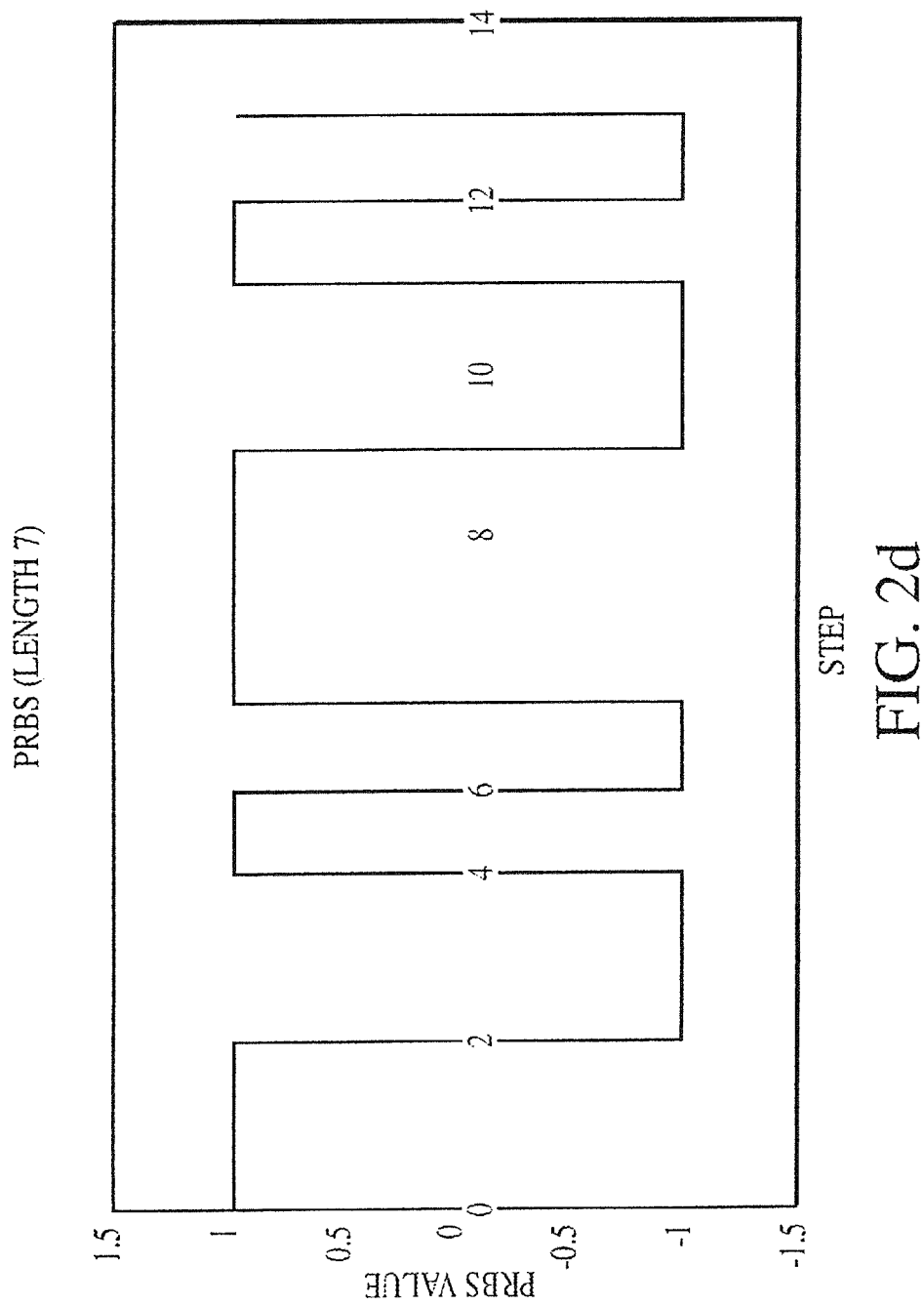
FIG. 2d is a graph of an exemplary embodiment of the modulation scheme according to the present invention, illustrating the PRBS modulation value versus applanation motor step number.
Figure 2E:
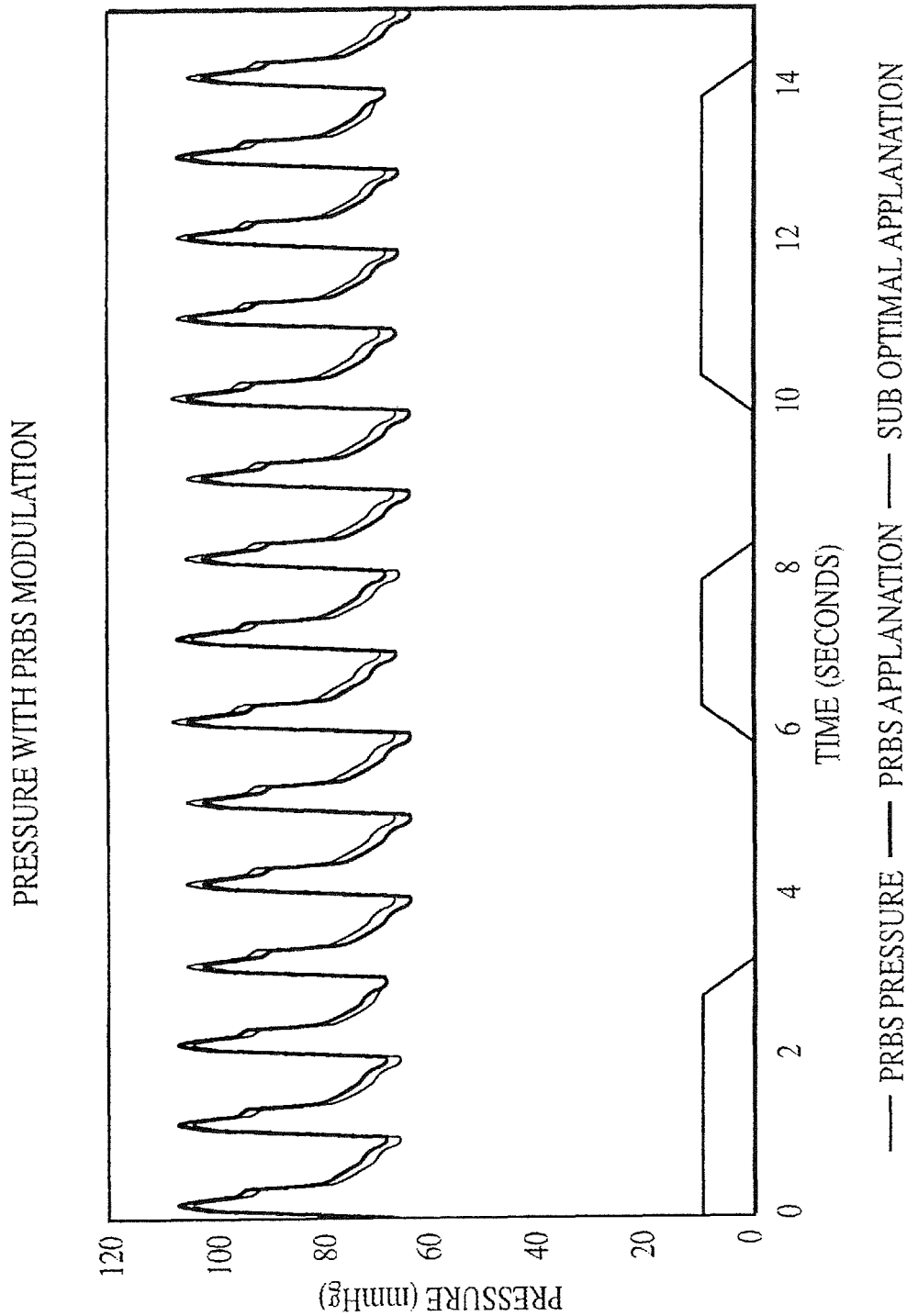
FIG. 2e is a graph of the tonometric pressure obtained from the patient of FIG. 2a with and without PRBS modulation applied to non-optimal applanation, illustrating the effects of PRBS modulation.
Figure 2F:
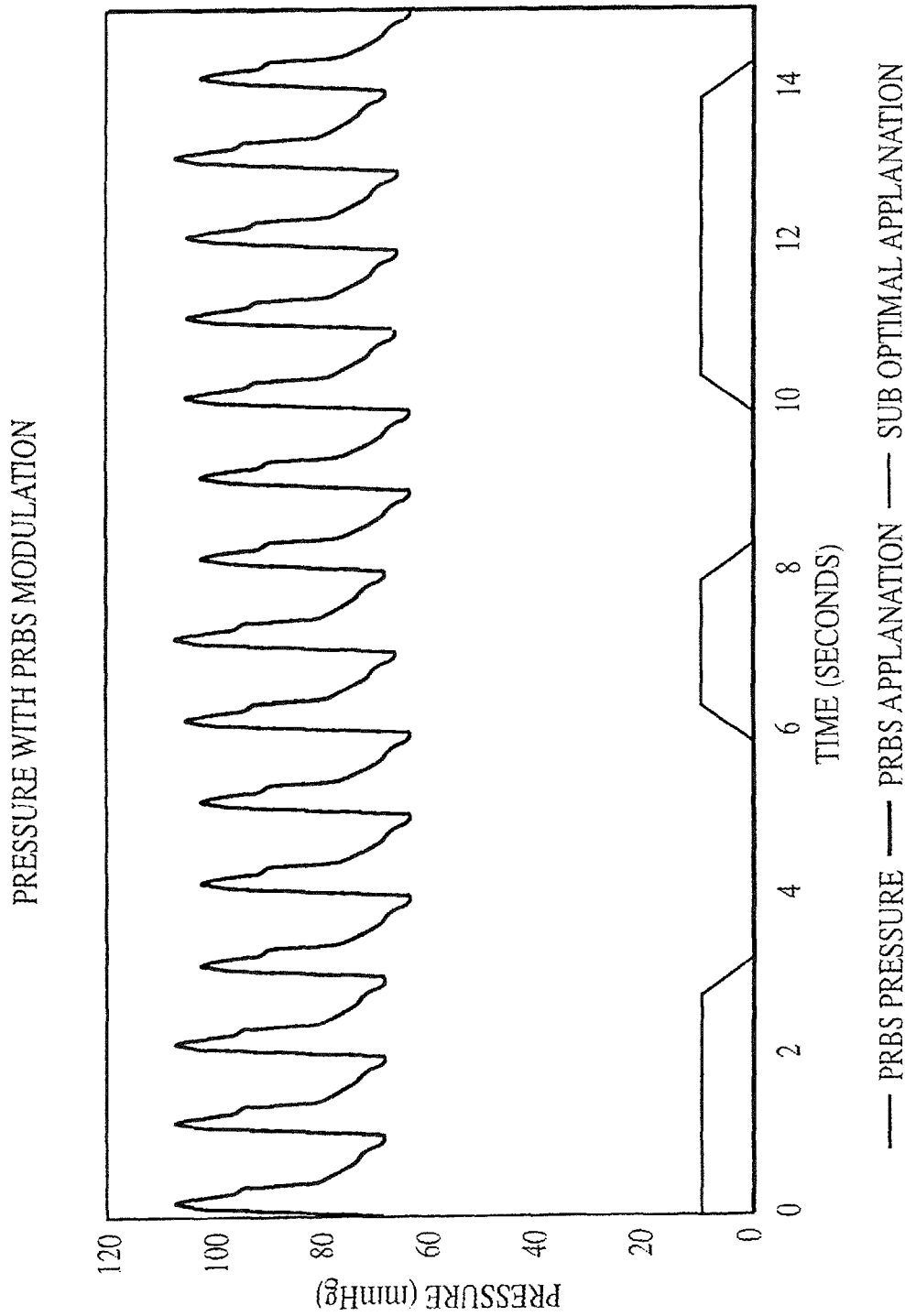
FIG. 2f is a graph of the corrected or restored tonometric pressure waveform after application of PRBS modulation to the non-optimal applanation profile.
Figure 2G:
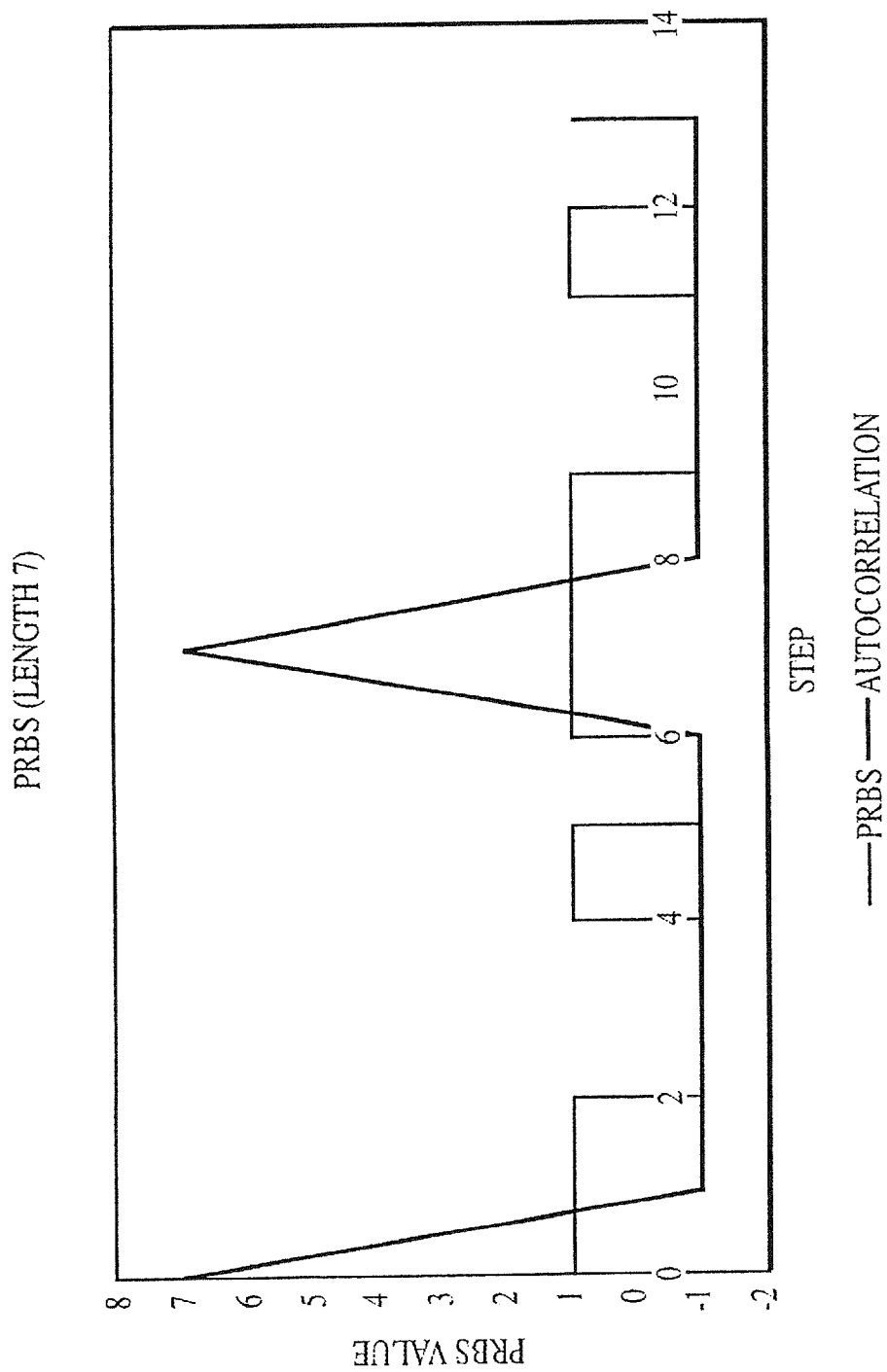
FIG. 2g is a graph of an exemplary embodiment of the PRBS modulation of the invention (PRBS length=7), illustrating the correlation between modulation and corrected pulse pressure.
Figure 2H:
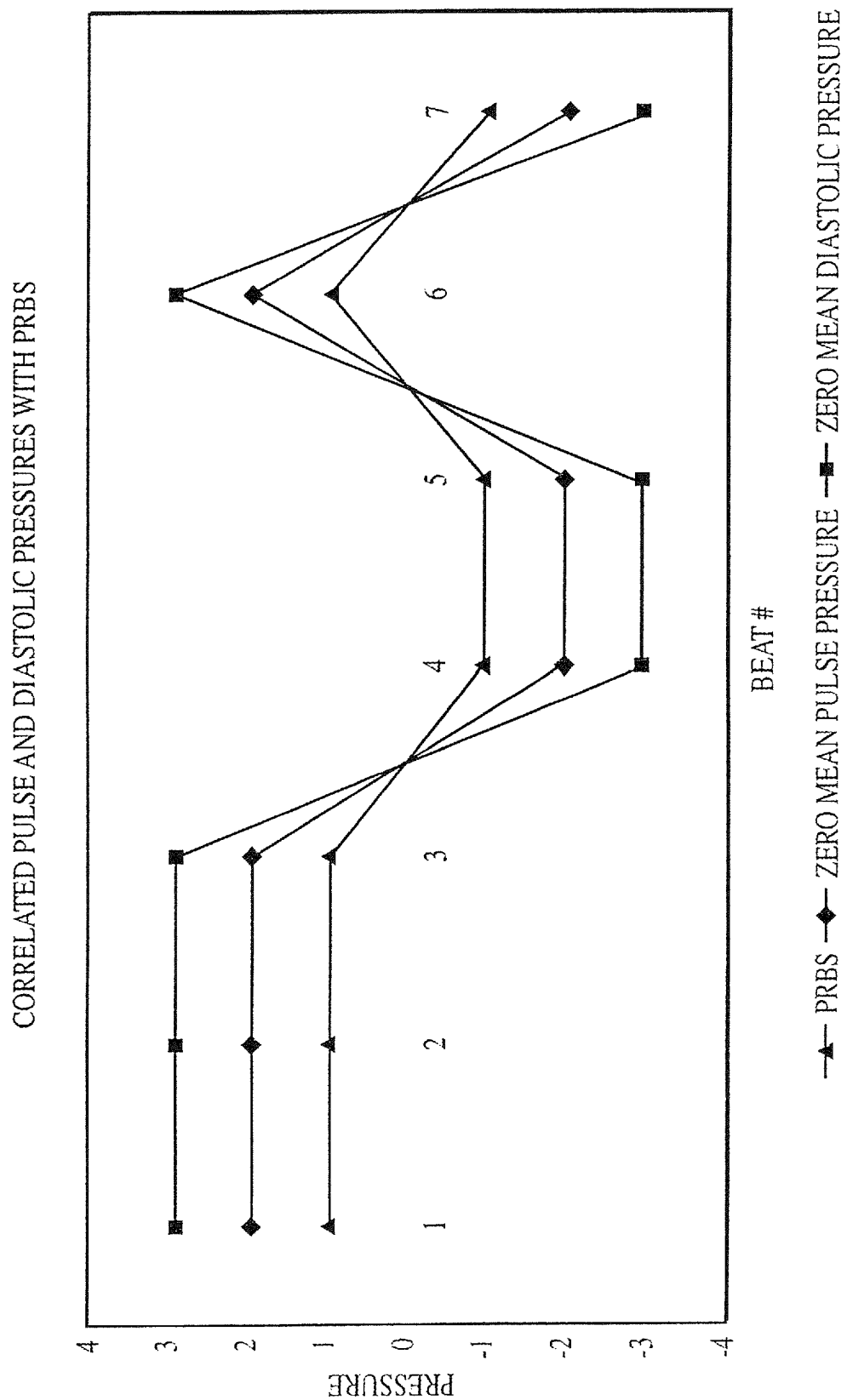
FIG. 2h is a graph of pressure versus beat number illustrating the correlation between the weighted zero mean values for exemplary pulse pressure and diastolic pressure, and PRBS modulation.
Figure 2I:
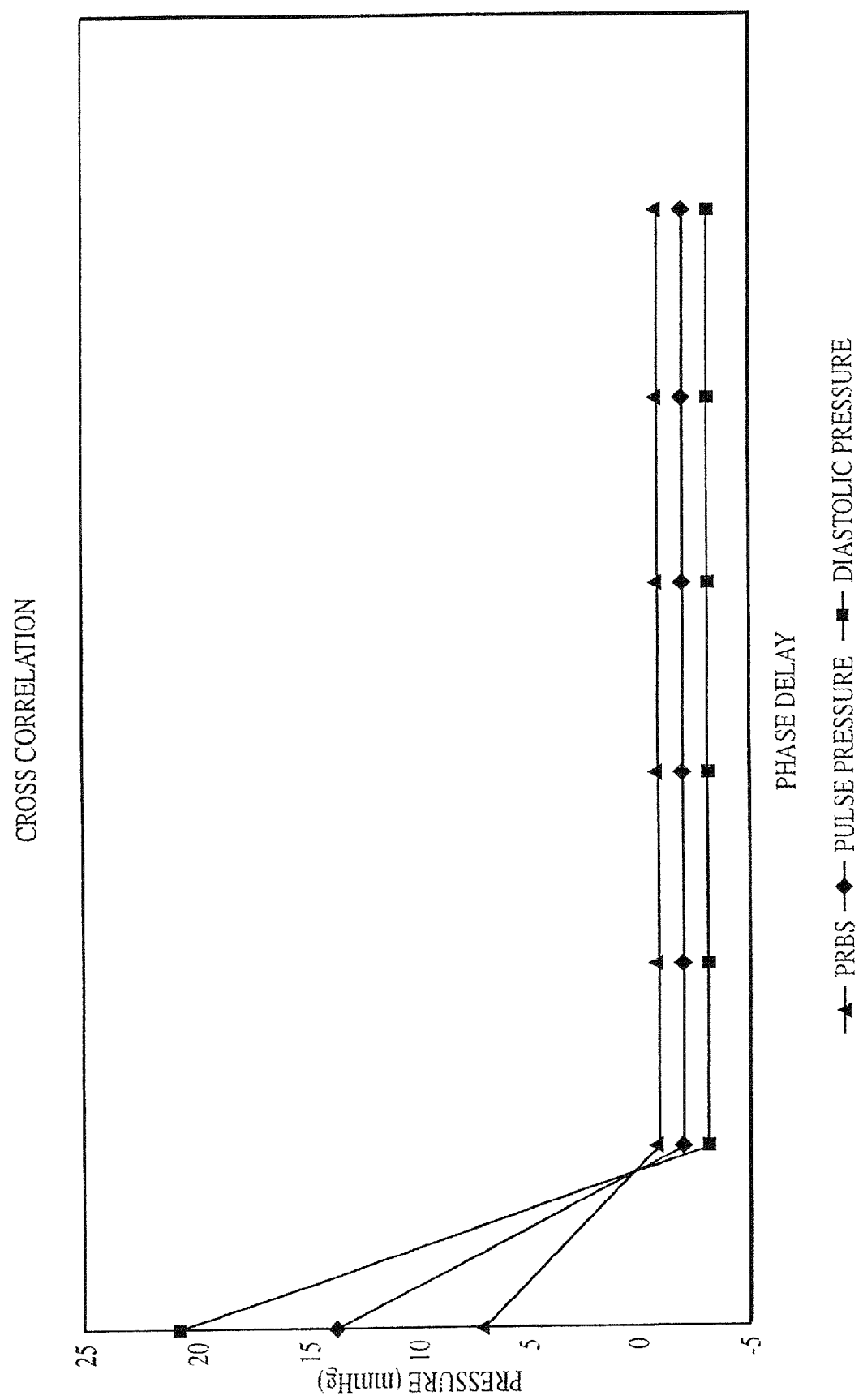
FIG. 2i is a graph of pressure versus phase delay for pulse pressure, diastolic pressure, and PRBS modulation according to one embodiment of the invention.

Referring now to FIGS. 2-2i, one exemplary embodiment of the method of identifying changes in the compression coupling and readjustment of the applanation level back to optimal (i.e., "second process") according to the invention is described in detail. It will be appreciated that while the following discussion of the exemplary embodiment is cast primarily in terms of the adjustment of the tonometric applanation level (i.e., level of compression), the techniques of the present aspect of the invention may be equally applied to the other spatial domains associated with the tonometric measurement environment; e.g., lateral position and proximal position. Such applications may be coupled to that associated with the applanation domain, or alternatively be entirely independent.

It will also be appreciated that while the following discussion is cast in terms of an exemplary embodiment utilizing Pseudo Random Binary Sequences (PRBS) generally complying with a structured sequence of the form $(2^n-1)$, other white noise, random/pseudo-random, or pseudo-noise (PN) processes may be substituted with success, and hence the following discussion is merely illustrative of the broader principles of the invention. For example, as one alternative, a pseudo-random generation algorithm of the type well known in the communications arts (such as that used for example in generating FHSS hop or CDMA pn "long code" sequences) is seeded with a given initial seed value and generates a pseudo-random sequence, the latter used to modulate the applanation level in the present invention. Other perturbations or sequences (any movement surrounding the optimal applanation position including for example sinusoidal perturbations) may also be substituted consistent with the present invention; however, the methods described with respect to the exemplary embodiment above have inherently good signal-to-noise ratio (SNR) across the frequency band of interest.

FIG. 2 shows a logical flow diagram of the exemplary embodiment of the second process 200. The process 200 generally comprises first providing a transducer adapted for determining pressure (step 202). The transducer is disposed proximate to the blood vessel of interest (step 204), in order to provide coupling of pressure signals from the blood vessel wall through the tissue and to the active surface(s) of the sensor. Note that an intermediary coupling agent (such as a gel) may be used if desired. Next, an optimal or near-optimal state of vessel compression is achieved per step 206. It will be recognized that such compression may be applied via the pressure transducer itself, or alternatively via another mechanism (such as a contact pad). The optimized level of compression can be determined using, inter alia, the methods of the aforementioned co-pending U.S. patent application Ser. No. 10/072,508 filed Feb. 5, 2002. The level of compression applied to the blood vessel is next varied over time (step 208). In the illustrated embodiment, the act of varying the level of compression per step 208 comprises modulating the level of compression in comparatively small magnitude "perturbations" according to a modulation sequence having particular desirable properties, although other schemes (e.g., non-sequential) may be used. The effects of the modulation on the observed pressure values (e.g., pulse pressure, diastolic, etc.) are then observed per step 210, and corrections in the level of compression applied to the blood vessel made per step 212 based on the observed effects of the modulation sequence.

It will be appreciated that the second process 200 (and associated apparatus) need not measure the applied pressure or compression, such as via a force sensor or the pressure transducer). Rather, the present embodiment is largely effects-based in that applanation level (compression) can be adjusted based simply on the observed effects of the modulation. Hence, the applanation mechanism can advantageously be made "dumb", thereby simplifying the mechanism as well as other aspects of the system. However, if explicit monitoring of the applied force or compression is desired, such intelligence can be utilized in conjunction with the invention as well.

As previously discussed, one clinical objective of the second process 200 is to maintain the tonometrically observed mean pressure within a given value (e.g., +/−10 mmHg) of the optimum tonometric pressure, which produces maximum pulse pressure. During the second process 200, both the patient's arterial pressure and the mechanical coupling between the tonometric transducer and the underlying artery can change. Either type of change introduces a variation in the tonometrically observed pressure. Hence, the present invention seeks to differentiate between physiologically-induced changes (e.g., those stemming from the patient's physiology, such as for example due to the introduction of pharmacological agents), and mechanical coupling changes in the tonometrically observed pressure. It also seeks to constantly correct for the second type of change (i.e., change in the mechanical coupling).

Sudden changes in the mechanical coupling between the tonometric pressure transducer and the artery (i.e. acceleration or "bumping" of the transducer or the wrist) can be detected by several techniques, as previously described herein with respect to FIG. 1, as well as that of FIGS. 4a-4d described below. Slower changes in the mechanical coupling must be detected and corrected by other means.

One method of detecting and correcting slower changes in mechanical coupling involves perturbing the system by modulating the compression of the artery and observing the resultant changes in tonometrically measured pulse pressure. The method and degree of perturbation should be optimized in accordance with the overall clinical objectives.

Accordingly, the Assignee hereof has developed exemplary clinical objectives for use in accordance with the exemplary process 200 described herein. It will be recognized that these objectives are merely illustrative, and may be adapted and modified as needed to particular clinical environments or desired levels of performance and accuracy.

(i) Display disruption—First, the disruption of the system pressure display by the induced perturbation should be minimized. Noticeable discontinuities in the pressure display and delays in transfer of the pressure signal to the patient monitor (e.g., based on a predetermined criterion such as delays of 0.1 seconds or greater) are unacceptable.

(ii) Responsiveness—The tonometrically observed pressure from 20 mmHg of optimum T-Line pressure to within 10 mmHg occurs in accordance with a given period of time (e.g., 1 minute). From a clinical perspective, excursions beyond roughly 10-15 mmHg in mean tonometrically measured pressure from the actual intra-vascular pressure (such as A-Line pressure) for extended periods, e.g., longer than 1-2 minutes, are often clinically undesirable. Although measurement error can occur, as reflected by prevailing FDA requirements for cuff accuracy (+/−5 mmHg mean error with a standard deviation of 8 mmHg), more frequent and longer duration divergences between tonometrically sensed pressure and true intravascular pressure reduce the clinical desirability of a device. Thus, a clinically useful system should operate such that it responds with reasonable speed and accuracy to changes in mechanical coupling.

(iii) Device Limitations—Limitations exist relating to the motion of the applanation motor of the system. These limitations include for example limits in the applied electrical power and resulting output (mechanical) power and torque, the control of wear over time (i.e., motor longevity), and limits in the motor velocity and acceleration which preclude instantaneous (i.e. step) changes in applanation. From bench data obtained by Assignee, diastolic pressure in representative patients changes on average 7 mmHg per 1000 motor steps (within the range of 4-10 mmHg per 1000 motor steps) at an applanation level near optimum. Furthermore, pulse pressure changes for the same individuals an average of 8 mmHg per 1000 motor steps (ranging from 4-14 mmHg per 1000 motor steps). One exemplary actuator and motor scheme utilized by the Assignee hereof suggests a maximum rate of about 1000 motor steps per second. Changes in actuator design to alleviate some of these limitations are not considered. Hence, it can be inferred that maximum rates of diastolic and pulse pressure change of about 7 mmHg/sec and 8 mmHg/sec, respectively, can be achieved with the aforementioned exemplary apparatus.

(iv) Variations in Pulse Pressure—The patient's pulse pressure is time variant. As is well documented in the literature, arrhythmias can produce cyclical changes in pulse pressure (i.e. pulsus alternans, wherein a succession of high and low pulses exist in such a manner that a low pulse follows regularly a high pulse, and this low pulse is separated from the following high pulse by a shorter pause than that between it and the preceding high pulse.) See, e.g., "*Apparent Bigeminy and Pulsus Alterans in Intermittent Left Bundle-Branch Block*", Laszlo Littmann, M.D., and Jeffrey R. Goldberg, M.D., Departments of Internal Medicine and Family Practice, Carolinas Medical Center, Charlotte, N.C., USA, which is incorporated by reference herein. It is well documented that patient respiration can produce sizeable changes in pulse pressure as well. Hence, a perturbation and servo-control system would ideally be largely if not completely insensitive to cyclical and random fluctuations in arterial pulse pressure.

In addition to the foregoing objectives and limitations, the properties of the tonometric measuring and control system must be determined. It is well known that the insertion of so-called "white noise" into a system is a useful means of identifying properties associated with that system. In the present context, the introduction of such white noise generates a pattern which effectively cannot be produced by the patient physiology. The inputs to the system include applanation motor position, and the "system" is the tonometrically obtained pulse pressure as a function of applanation level. Cross-correlating the changes in applanation position induced by the white noise with the resultant observed pulse pressure produces a relationship between the applanation motor position and pulse pressure. This relationship is advantageously quite robust in the presence of random or periodic fluctuations in pulse pressure, due largely to the insertion of the white noise.

However, several considerations exist with respect to the practical implementation of white noise modulation of applanation motor position in the present invention. First, true "white noise" assumes a normal or Gaussian distribution of motor position. Such normal distributions can contain very large excursions from the mean albeit with increasingly less frequency (theoretically not bounded), whereas in contrast the motor position in the physical implementation of the present invention is bounded.

Second, the time to travel from one position limit to the other (if such travel is needed) is significant, as previously discussed with respect to maximum motor rate. Instantaneous changes in applanation mechanism position are therefore not possible.

Third, white noise identification theoretically requires an infinite period time for convergence, even approximations of which are not practical in the clinical setting. Ideally, a useful clinical device would employ control systems which would converge in a very short period of time, thereby enhancing the continuity of the tonometric pressure measurement.

As is known in the mathematical arts, Pseudo Random Binary Sequences (PRBS) are a defined sequence of inputs (+/−1) that possess correlative properties similar to white noise, but converge in within a give time period. In addition, the inputs can be specified (and thereby optimized) to produce more effective signal-to-noise ratio (SNR) within the constraints of the system. One common type of PRBS sequence generator uses an n-bit shift register with a feedback structure containing modulo-2 adders (i.e. XOR gates) and connected to appropriate taps on the shift register. The generator generates a maximal length binary sequence according to Eqn. 3:

$$\text{maximal length binary sequence} = \text{length } (2^n - 1) \tag{Eqn. 3}$$

The maximal length (or "m-sequence") has nearly random properties that are particularly useful in the present invention, and is classed as a pseudo-noise (PN) sequence. Properties of m-sequences commonly include:

(a) "Balance" Property—For each period of the sequence, the number of '1's and '0's differ by at most one. For example in a 63 bit sequence, there are 32 '1's and 31 '0's.

(b) "Run Proportionality" Property—In the sequences of '1's and of '0's in each period, one half the runs of each kind are of length one, one quarter are of length two, one eighth are of length three, and so forth.

(c) "Shift and add" Property—The modulo-2 sum of an m-sequence and any cyclic shift of the same sequence results in a third cyclic shift of the same sequence.

(d) "Correlation" Property—When a full period of the sequence is compared in term-by-term fashion with any cyclic shift of itself, the number differences is equal to the number of similarities plus one (1).

(e) "Spectral" Properties—The m-sequence is periodic, and therefore the spectrum consists of a sequence of equally-spaced harmonics where the spacing is the reciprocal of the period. With the exception of the dc harmonic, the magnitude of the harmonics are equal. Aside from the spectral lines, the frequency spectrum of a maximum length sequence is similar to that of a random sequence.

Accordingly, detecting and correcting slower-rate changes in mechanical coupling as previously described can be accomplished by applying PRBS modulation of the applanation position, and observing the resultant changes in tonometrically observed pulse pressure. In one exemplary embodiment of the present invention, the physical implementation of such a system contains three interactive "components": (i) a modulator; (ii) a signal restoration entity; and (iii) an identification/servo control entity. It will be recognized by those of ordinary skill that the term "entity" as used herein relates to any number of a wide variety of implementations, ranging from a corporeal entity (e.g., electronics and associated integrated circuits) to a completely virtual or intangible one (e.g., one manifest in the form of algorithms, routines, or software objects or components resident across the various hardware environments of a system).

The following exemplary description illustrates the operation of the aforementioned multi-component system according to one embodiment of the invention.

Referring now to FIGS. 2*a*-2*c*, the characteristics and response of an exemplary patient are described. As shown in FIG. 2*a*, the patient exhibits a given pulse pressure versus diastolic pressure relationship 230. The maximum pulse pressure 232 (e.g., 42 mmHg in the illustrated example) occurs at a diastolic pressure of about 75 mmHg 234.

Furthermore, it is assumed for purposes of illustration that the applanation motor is held at a constant position (at the point of optimal compression corresponding to maximal pulse pressure), and that the patient has a time-invariant arterial pressure with a heart rate of 60 bpm with the shape 236 shown in FIG. 2*b*. If the patient's artery is not sufficiently compressed, a lower diastolic pressure 237 (e.g., diastolic pressure=67 mmHg in this example) will result, as indicated by the "sub-optimal" waveform 238 of FIG. 2*c*. Note that the pulse pressure (systolic minus diastolic) at a tonometrically measured diastolic pressure of 67 mmHg is only approximately 36 mmHg. Under this condition, the system must identify the fact that the artery is under-compressed and adjust the applanation level appropriately over time.

Referring now to FIGS. 2d-2e, the modulation entity of the servo process 200 of the invention is described in the context of the foregoing example. The modulator of the present embodiment introduces changes in artery compression (applanation position) over a limited range around the "optimal" operating point. These changes are in the present embodiment synchronized with the downward slope of the arterial pressure waveform, this downward slope being associated with diastolic relaxation of the heart. Other synchronizations (or even lack of synchronization) may be used if desired, however. The modulations induced by the modulation entity ramp the applanation mechanism position from one extreme to an equal and opposite extreme (e.g., 400 motor steps in the present embodiment) around the operating point over a brief period (e.g., 0.5 seconds), although other profiles (symmetric or non-symmetric) and durations may be substituted if desired. The decision to move from one extreme to another is controlled in this embodiment by a Pseudo Random Binary Sequence (PRBS) of the type previously described. This modulation scheme produces changes in pressure offset, and may produce highly correlated changes in pulse pressure.

In the illustrated embodiment, a PRBS sequence of length=7 is implemented (i.e., 1, 1, 1, −1, −1, 1, −1) to modulate the pressure waveform as shown in FIG. 2d. Note that for the clinical application, the respiratory period of the patient, and its corresponding cyclical fluctuations in pulse pressure, approximates the repetition period of the PRBS of length 7. Hence, clinical embodiments of the application incorporate a PRBS of appropriate length such as length=15 (i.e., 1, 1, −1, 1, −1, 1, 1, 1, 1, −1, −1, −1, 1, −1, −1) or length 31 (i.e., 1, 1, 1, 1, −1, 1, 1, −1, −1, 1, 1, 1, −1, −1, −1, −1, 1, 1, −1, 1, −1, 1, −1, −1, 1, −1, −1, −1, 1, −1, 1) Specifically, the PRBS sequence repeats every 7, 15, 31 beats if one does not allow for transition beats, and in the exemplary case 11, 22, or 47 beats respectively allowing for transition beats. Any noise source that repeats in the same time base (sinusoidal noise frequency) will have a greater impact on system performance than noise sources with other frequency content. Respiration period occurs in the range of 5-7 seconds; hence, during this period, anywhere from 4-14 heartbeats could be observed. Thus, a PRBS sequence of length 7 with an effective length 11 when transition beats are included falls directly within the respiration period. The longer sequences do not have that problem. Conversely, however, the noise rejection properties require a complete cycle of data for proper function. Hence, control using sequences that are excessively long are prone to sluggish control, thereby detracting from system performance.

FIG. 2e depicts the practical implementation of PRBS changes in applanation level. Practical mechanical considerations relating to the applanation motor preclude step changes in applanation level of sufficient magnitude to produce a significant change (e.g., 6 mmHg) in observed tonometric pressure. Thus, for the present embodiment, the applanation position is ramped over a period of time (e.g., 0.5 seconds), as shown in the PRBS portion 239 of FIG. 2e. Since no guarantee exists that the ramp will complete by the end of the beat, a variable delay in the PRBS, which is a function of heart rate and number of motor steps traveled, is included within each transition period without loss of the correlative properties. Typically this delay is 1 heart beat. but at high heart rates could extend to two and possibly more beats. It is noted that the PRBS portion 239 of FIG. 2e is dimensionless. In effect, two classes of beats are created in the present implementation; "measurement" beats and "transition" beats. When the motor is moved, transition beats are added (e.g., for a length=15 sequence, 7 or 8 transition beats are added).

Referring now to FIGS. 2e and 2f, the signal restoration entity of the invention is described in detail. As shown above, the modulation entity will introduce changes in the measured pressure waveform. These changes in the pressure waveform may be disruptive to the clinician under certain circumstances. Note that the PRBS-modulated pressure waveform 240 of FIG. 2e varies significantly around the tonometric pressure 242 that would otherwise be observed if the PRBS or other modulation was not active. Hence, the signal restoration entity must anticipate the changes in the observed tonometric pressure waveform introduced by the modulation entity, and (mathematically or otherwise) restore the modulated waveform to a shape that is clinically equivalent to the un-modulated tonometric waveform.

Specifically, by implementing a linear ramp during the period when the modulation is active, the original un-modulated waveform can be restored. This process assumes the amount of change that is observed by the modulation is not large (e.g., <roughly 6 mmHg in the illustrated embodiment) and is adaptively identified (i.e., the cross-correlation of the PRBS modulation sequence and diastolic pressure from which the average diastolic pressure has been removed can be used to provide an estimate of the expected change in pressure produced by the modulation).

Note that the foregoing process in essence adds or subtracts a pressure correction offset to the measured pressure. When the modulation entails extension of the sensor from the mechanism (in the exemplary embodiment), the pressure offset correction is subtracted from the measured pressure data, and vice-versa. The value (units in mmHg) of the offset correction can not be directly determined unless compared with a source of true intravascular pressure (e.g., A-Line, thus defeating the purpose of the tonometric sensor), but it can be estimated by evaluating the change in diastolic, systolic, mean, pulse, or similar pressure values correlated to the change in motor position. Thus, for example, the cross-correlation between the PRBS and the diastolic pressures (mean pressure removed) can be used to estimate the offset correction. This estimate can be updated with each new beat producing a continuous estimate of the offset correction. Note that during applanation motor ramping, the offset correction of the exemplary embodiment also ramps from one extreme to the other. Additionally, it will be recognized that the amount of modulation (e.g., number of motor steps in the illustrated embodiment) can be adjusted to produce the desired amount of pressure change. In the present embodiment, the modulation level is continuously adjusted to achieve 5 mmHg peak-to-peak excursion subject to a limit; i.e., provided that the peak-to-peak excursion is limited to between 50 and 800 motor steps. Other modulation schemes and limits can be used consistent with the invention, however.

Note that lead/lag relating to the assumed start of the motor movement (as opposed to the actual start of movement), and the introduced changes in pressure, can lead to small artifacts or "bumps" in the pressure waveform display; however, these are often imperceptible to the operator, and advantageously no points of discontinuity exist in the display, unlike prior art systems.

Errors between the actual and predicted pressure change (i.e., those predicted by the signal restoration entity relating to the applied modulation) are exhibited as small jitter synchronized with the PRBS in the diastolic pressure display. FIG. 2f depicts the "restored" waveform 242; i.e., the waveform(s) of FIG. 2e after correction by the restoration entity. Note that the error produced by the linear ramp approximation is small compared to both (i) the pulse pressure, and (ii) pixel resolution of the monitor. Thus, the process of restoring a clinically equivalent waveform is readily achieved using the techniques described herein.

Referring now to FIGS. 2g-2i, the identification/servo control (ISC) entity of the present embodiment is described.

As shown in FIG. 2f, the corrected ("restored") pulse pressure values associated with points on the restored waveform 242 fluctuate around corresponding ones of the nominal, non-modulated sub-optimal applanation waveform 238. Further, it will be recognized that these fluctuations, albeit comparatively small in magnitude, generally correlate with the modulation in applanation level, as illustrated by FIG. 2g.

The ISC entity of the present embodiment takes advantage of the correlative properties of white noise. As shown in FIG. 2g, an auto-correlation of the PRBS modulation is performed. The auto-correlation of the PRBS signal has a gain equal to the PRBS length (e.g., 7) for zero phase delay, and negative unity gain for other phase delays until the PRBS repeats. The PRBS modulation, time synchronized tonometrically measured pulse pressure, and un-corrected diastolic pressures for the preceding example are displayed in Table 2. Note that the PRBS values labeled "T" indicate transition beats where the applanation motors are still in the process of ramping from one position to the next. These beats are removed from the subsequent cross-correlation without loss of the correlative properties of the PRBS.

TABLE 2

| Beat | PRBS | Pulse Pressure | Un-Corrected Diastolic Pressure |
|---|---|---|---|
| 1 | 1 | 38 | 70 |
| 2 | 1 | 38 | 70 |
| 3 | 1 | 38 | 70 |
| 4 | T | 35 | 66 |
| 5 | −1 | 34 | 64 |
| 6 | −1 | 34 | 64 |
| 7 | T | 37 | 68 |
| 8 | 1 | 38 | 70 |
| 9 | T | 35 | 66 |
| 10 | −1 | 34 | 64 |
| 11 | T | 37 | 68 |
| 12 | 1 | 38 | 70 |
| 13 | 1 | 38 | 70 |

FIG. 2h illustrates the weighted zero-mean values for pulse pressure and diastolic pressure (after removing the "transition" (T) beats) for the first 7 beats, and synchronized to the PRBS modulation. It will be noted that the pulse pressure values 250 and diastolic pressure values 252 are well correlated with the PRBS modulation of applanation level 254.

Performing the cross-correlation between the PRBS modulation of applanation and the pulse and diastolic pressures produces a large signal at phase delay=0, as shown in FIG. 2i. For diastolic pressure, the change induced by the modulation equals 21 mmHg divided by the PRBS length=21/7=3 mmHg. This means that the modulation process (extending the sensor out from operating point "0" during the modulation) caused a 3 mmHg increase in diastolic pressure. The total excursion (from PRBS="−1" to PRBS="1" thus equals 6 mmHg (70 mmHg−64 mmHg) using the table above. Similarly, the modulation-induced change in pulse pressure as shown in FIG. 2i equals 14/7 or 2 mmHg. Thus, the system recognizes that increasing compression (applanation) will increase the observed pulse pressure. Subsequently, the control system can change the operating point (applanation motor position around which PRBS modulation operates) appropriately to maintain optimal coupling.

Using this approach, the control system can accurately track on a beat-by-beat basis the motor position corresponding to the applanation level that produces maximum pulse pressure.

A circular buffer arrangement is used in the exemplary embodiment of the apparatus implementing the foregoing technique; this advantageously allows the calculation to be updated once per beat. It will be recognized, however, that other arrangements may be used to implement the desired functionality.

It will also be recognized that the techniques described above with respect to the second process may be equally applied to the other domains of spatial variation; i.e., the lateral and/or proximal search algorithms with proper selection of random/pseudo-random sequence (e.g., PRBS) parameters, thereby providing continuous tracking in the selected direction(s) as well as in the application domain. Such application and selection are readily implemented by those of ordinary skill given the present disclosure, and accordingly are not described further herein.

Based on observations and testing performed by the Assignee hereof, the performance of the present invention may be further enhanced under certain circumstances by the inclusion of one or more optional control and signal processing features; use of these features can enable the system to respond more quickly to an event by, inter alia, mitigating control overshoot and/or eliminating unwanted noise and other artifacts from the processed signals(s). These features include: (i) Hampel filtering of pulse and diastolic pressures; (ii) the addition of a proportional component to the control (servo) loop; (iii) the adjustment of integral control of the servo loop through estimation of the SNR; (v) increasing the precision of the diastolic cross-correlation; (vi) control of the initial settings for the diastolic pressure cross-correlation arrays; (vii) adjusting the integral gain based on the average pulse pressure; and (viii) correcting for BMI or other scaling artifact. Each of the foregoing features are now described in detail.

(i) Hampel Filter for Pulse and Diastolic Pressures—Improperly detected beats, noise, and cardiac arrhythmias can introduce large one-time changes in pulse pressure measurements that are not reflective of the applanation state of the patient. In the context of the second process 200 described above, these beats can potentially disrupt the feedback control. One exemplary method of removing most of these beats comprises independently applying a Hampel filter of the type well known in the signal processing arts to each of the positive PRBS pulse pressure and negative PRBS pulse pressure values in the respective arrays. The Hampel filter is advantageously employed as opposed to other filtering techniques including low pass filters or median filters which increase the time lag in the servo control loop.

(ii) Addition of Proportional Component to Servo Loop Integral Control—The PRBS-based algorithm described above operates generally as a sophisticated block filter with a lag equal to ½ of the PRBS length. In the second process 200, transition beats (PRBS length/2) are added to the computation, thereby creating a lag (e.g., 11.25 beats in the above example) from a change in coupling to its full impact to its identification through the cross-correlation with the PRBS and subsequent servo control. This lag can produce an overshoot in the integral servo control system when recovering from a manually introduced step change in artery compression (such as may be experienced when the NIBP measurement apparatus is jarred), and the integral gain is set too large. Adding a proportional component to the servo control algorithm and retuning the integral control gain advantageously reduces the magnitude of this overshoot. Since the servo control system operates based on changes in the "target" applanation level, a proportional control component may take the form of Eqn. 4 below:

$$M_{TP}(t)=K_p*(X_{corr}[t]-X_{corr}[t-k])\qquad\text{(Eqn. 4)}$$

where $M_{TP}(t)$ is the new target applanation motor position, is the $X_{corr}$ is the $0^{th}$ delay of the cross-correlation of the PRBS and zero mean pulse pressures, t is the current pulse, and k is the number of beats past. In one exemplary embodiment, values of (k=3) and $K_p$=1×(integral gain) are utilized.

(iii) Integral Control of the Servo Loop by Estimating SNR—The non-zero terms of the aforementioned cross-correlation provide some indication of the noise potentially present in the pulse pressure estimates. Adding a "governor" to the servo control system which is triggered upon attaining one or more predetermined criteria; e.g., when the non-zero terms (average absolute or maximum absolute) are a percentage of the $0^{th}$ term, can decrease the sensitivity of the system to such noise. For example, a manually introduced step change in artery compression can introduce a large change in the operating state (see discussion of the first process 100 above), which can drive the initial recovery from the event in the wrong direction until the aforementioned identification lag is overcome. Meanwhile, the non-zero elements of the cross correlation also become large until the lag is also overcome. The governor mechanism described herein mitigates the effects of these non-zero elements during the lag period.

(iv) Improved Precision on Diastolic Cross-Correlation— As described above with respect the "nominal" embodiment of the present invention, cross-correlations are performed between the diastolic pressure and the PRBS component. The accuracy of these cross-correlation calculations may be increased by using the time varying signed modulation signal as the basis of the cross-correlation, rather than the PRBS as previously described. When the signed modulation signal is implemented, the cross-correlation value is divided by the average absolute modulation signal for the period under consideration; otherwise, the servo adjustment to subsequent modulation counts and operating applanation position may be adversely impacted.

(v) Control of Initial Settings for Diastolic Pressure Cross-Correlation Arrays—To provide an initially reactive system and to speed initial convergence, the nominal system is initialized to provide comparatively large modulations. On some patients, however, the modulation (measured in the present context in terms of "motor delta" which is defined as the estimated absolute change in applanation motor position in steps required to change end diastolic pressure by a predetermined quantity such as 2.5 mmHg) is initially excessive; e.g., up to 8 or 10 times the number of motor steps otherwise required. If motor delta is set too large, then the applanation motor will initially move much farther than necessary/desired during PRBS, and the patient's diastolic pressure will change much greater than anticipated. Waveform reconstruction will not sufficiently compensate for changes in diastolic pressure, thus shifts or oscillations in diastolic pressure will be noticeable on the pressure display, which is undesirable. Nonetheless, the large motor delta will aid in the rapid convergence to the applanation position corresponding to maximum pulse pressure. On the contrary, if the motor delta is set too small, then applanation will not sufficiently excite the system, thus slowing convergence to the applanation position corresponding to maximum pulse pressure. Meanwhile, the restoration process will overcompensate for the change in diastolic pressure with PRBS modulation, and produce noticeable shifting in the displayed pressure.

Figure 3:
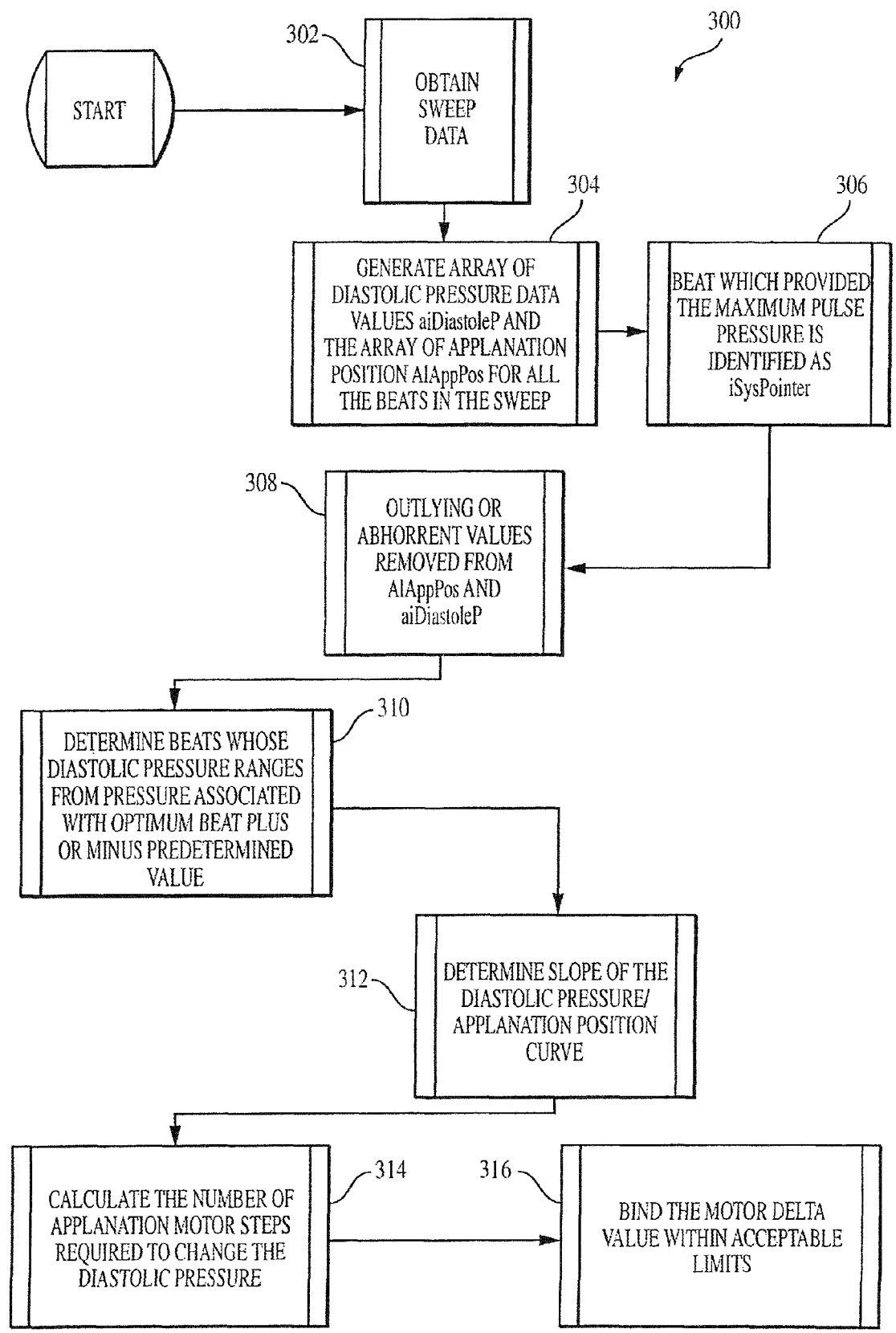
FIG. 3 is a logical flow diagram illustrating one exemplary embodiment of the method of determining the optimal initial modulation according to the present invention.
Figure 3A:
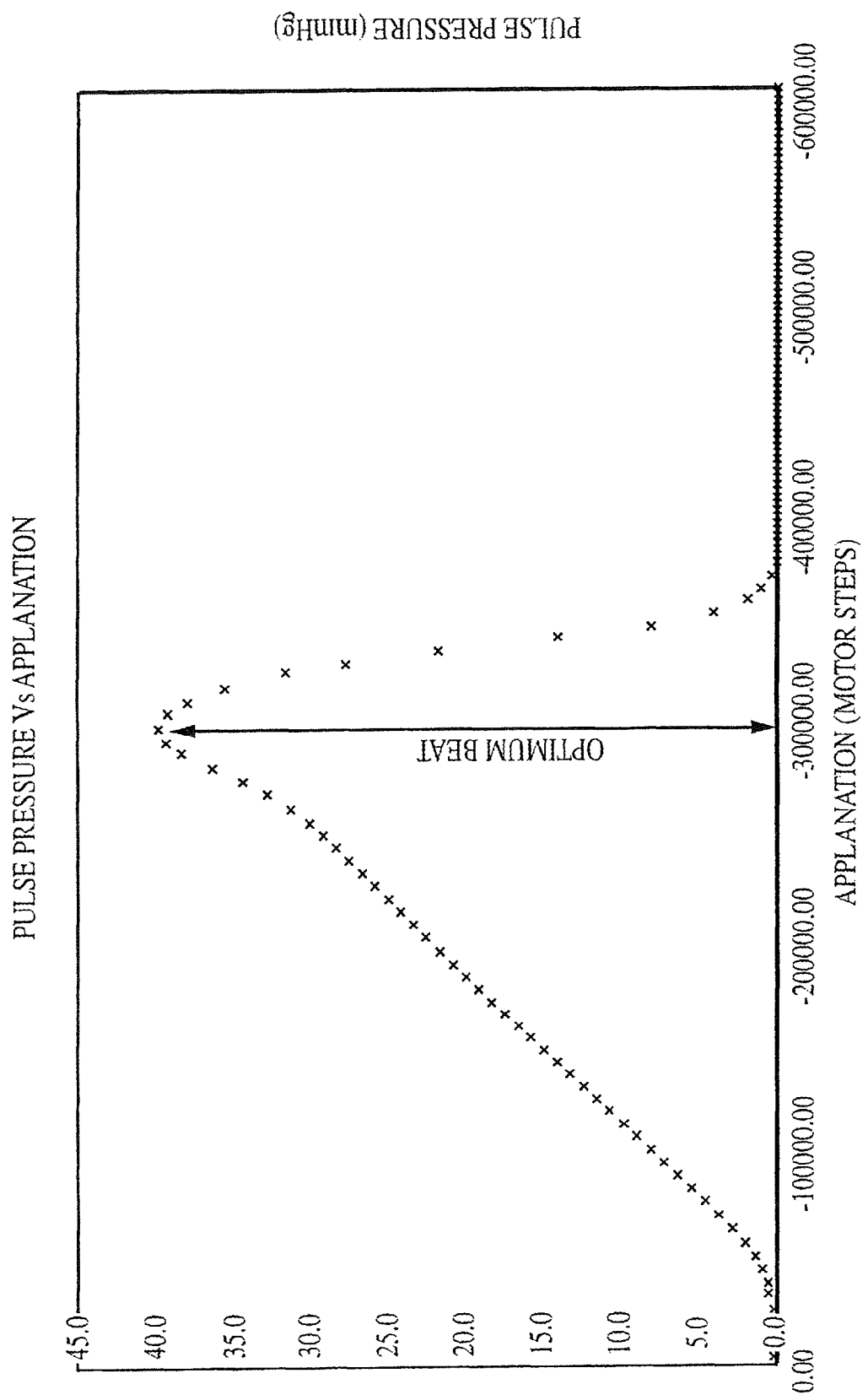
FIGS. 3a and 3b are graphs illustrating various aspects of the calculations supporting the methodology of FIG. 3.
Figure 3B:
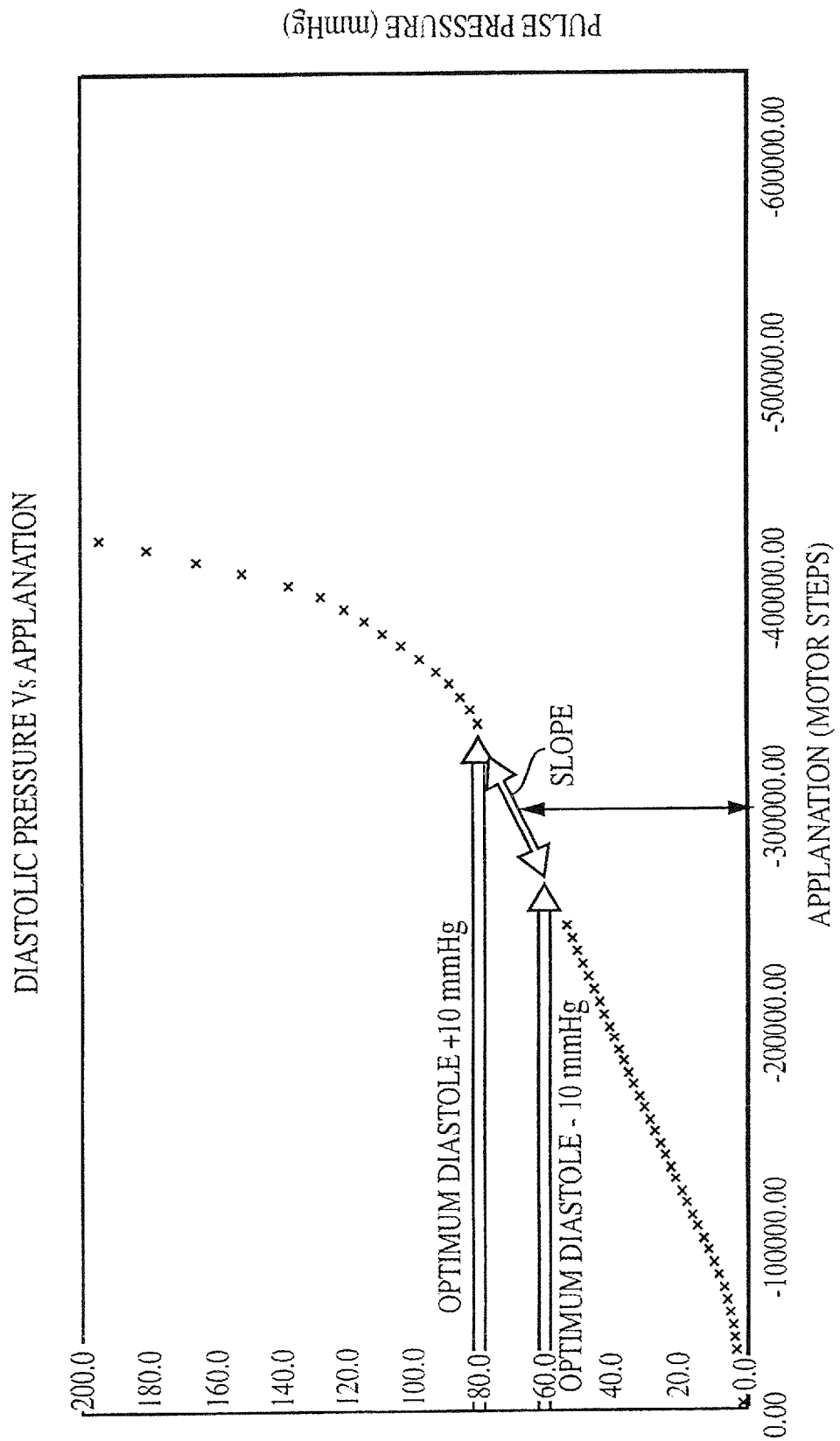

To address this issue, the initial modulation level can be controlled, such that a predetermined maximum number of steps (e.g., 150) are utilized, or alternatively by applying a more sophisticated technique of determining the optimal initial modulation as illustrated in FIGS. 3-3b. Specifically, the initial applanation pressure sweep provides sufficient data to estimate the necessary motor delta to change diastolic pressure by a predetermined amount (e.g., 2.5 mmHg). The sweep data is first obtained (step 302 of FIG. 3), and is used to generate the array of diastolic pressure data values, aiDiastoleP[ ], and the array of applanation position, alAppPos[ ], for all the beats in the sweep (step 304). At the end of the applanation sweep process, the beat which provided the maximum pulse pressure is identified as iSysPointer (step 306).

In one exemplary embodiment of the method 300, outlying or abhorrent values are first removed from alAppPos[ ] and aiDiastoleP[ ] via a Hampel filter of the type well known in the art, using for example a 3- or 4-standard deviations (σ) outlier test or comparable mechanism (step 308). Other filter types can also be substituted, as will be appreciated by those of ordinary skill.

Next, in step 310, those beats whose diastolic pressure ranges from that associated with the optimum beat minus a predetermined value (e.g., −10 mmHg) to that corresponding to optimum beat plus the predetermined value (+10 mmHg) is determined.

The slope of the diastolic pressure/applanation position curve (in units of mmHg per motor step in the present embodiment) over that region of interest is next determined in step 312. This provides in effect a sensitivity of diastolic pressure to motor position.

In step 314, the slope value(s) determined in step 312 are used to calculate the number of applanation motor steps required to change the diastolic pressure by a desired amount (e.g., motor delta=2.5/slope in the illustrated embodiment). In the illustrated embodiment, the PRBS process is simply a method of determining the slope around the nominal.

Lastly, in step 316, the motor delta value is bounded within acceptable limits which will reduce initial "overstepping" of the modulation as previously described. For example, in one embodiment, the allowed initial motor delta value is bounded on the low end by 40 motor steps, and on the high end by 400 motor steps.

It will also be recognized that a similar issue (i.e., "overstepping") may arise when initiating an applanation sweep subsequent to the first process 100 described above with respect to FIG. 1. Accordingly, the aforementioned methods of mitigating excessive modulations can be employed in this context as well.

(vii) Gain Adjustment Based on Average Pulse Pressure— Adjustments to integral gain (i.e., autocorrelation gain with zero phase delay) is in the above-described embodiment independent of the underlying average pulse pressure, as reflected in the following relationship:

$$M_{TP}(t)=(K_{pp}*K_{pp}[t]*K_n[t]*X_{corr}[t])+M_{TP}(t-1)\qquad\text{(Eqn. 5)}$$

where $M_{TP}(t)$ is the new target applanation motor position, $M_{TP}(t-1)$ is the previous target applanation motor position, $X_{corr}$ is the $0^{th}$ delay of the cross-correlation of the PRBS and zero mean pulse pressures, t is the current pulse, $K_i$ is the fixed integral gain, $K_{pp}[t]$ is the integral gain modifier that is inversely related to pulse pressure, and $K_n[t]$ is the integral gain modifier that is related to the signal-to-noise ratio.

Thus, as an example, a pulse pressure cross-correlation of magnitude 2 has the same control "impact" at an average pulse pressure of 60 mmHg as it does at 20 mmHg. Making the value of this gain quasi-inversely proportional to the underlying average pulse pressure makes the control system more responsive both for individuals with low pulse pressure, and for all individuals when the system is not situated close optimum. It will be recognized that the foregoing coupling between the integral gain and pressure may take on other forms as well. For example, the gain adjustment need not be proportional or quasi-proportional, but rather may be based on a limited number of continuous or non-continuous discrete pressure ranges if desired (e.g., 0-10 mmHg, >10-<25 mmHg, etc.), or made deterministic upon other measured or observed parameters. Furthermore, the gain adjustment may be coupled to underlying criteria other than pulse pressure; e.g., diastolic or systolic pressure, mean pressure, blood flow velocity or kinetic energy, vessel diameter, body mass index, etc.

(viii) Correction for Scaling on Observed Pressure Waveforms—Clinical observations made by the Assignee hereof indicate that under some circumstances, limited changes in the pressure displayed to the operator may be induced in part by the modulation occurring during the second process 200 described above. One cause of this behavior relates to the interaction of the pressure waveform restoration and scaling (e.g., BMI) algorithms with changing mean pressures. To address this behavior, an alternate scaling implementation may be used. Specifically, the high-pass filter (HPF) component of the pressure waveform ($2^{nd}$ order 0.25 Hz cutoff frequency) is scaled, and combining the HPF component multiplied by the scaling factor (e.g., BMI scale factor) with the raw pressure waveform to produce the scaled pressure waveform.

It will be recognized that the foregoing features (i)-(viii) are purely optional in nature, and may be selected by the system designer at time of apparatus design and manufacture based on the anticipated applications. Alternatively, production devices may incorporate the functionality for each enhancement (as well as others), with the end-user having the ability to select which features they wish to employ in particular applications (such as via a GUI configuration menu, API, or similar mechanism).

As yet another alternative, the production device may be configured to automatically or adaptively determine if particular performance enhancements should be utilized. For example, during start-up or monitoring, the device may be configured to institute or "turn on" a given feature or group of features, monitor the effects on the output data in light of prior data collected while the enhancement feature(s) were inoperative, and then decide which if any features should be utilized and under what conditions. As a simple example, consider where the Hampel filter (Item (i) above) is applied over time to the PBRS pulse pressure at times where sudden change in values are expected (i.e., start or re-entrance into the servo control system). The system may be programmed to disable the Hampel filter during these periods of servo control or during the period immediately following an ipsilateral oscillometric cuff deflation.

Hence, the present invention contemplates the use of innate "intelligence" within the device hardware and software adapted to selectively control the application of one or more enhancement features during device operation. Such innate control can be readily implemented by those of ordinary skill given the present disclosure, and accordingly are not described in greater detail herein.

Interaction of First and Second Processes

The first process 100 and second process 200 described above are in the exemplary embodiment adapted to operate in concert with each other. As discussed, the first process 100 responds to sudden changes in mechanical coupling between tonometric sensor and the underlying artery while the second process is designed to, inter alia, counteract lower frequency drifting in the mechanical coupling. Generally speaking, the more quickly that the second process 200 can respond to changes in mechanical coupling, the less restrictive the constraints that are placed on the performance of the first process 100. With the presence of the second process 200, the first process 100 need not be reactive to small mechanical coupling changes; the second process 200 can be used to provide recovery without the need to disable current pressure display for any period of time to perform the limited pressure search.

Accordingly, the following comprise exemplary values for various parameters used by the first and/or second processes of the invention, which are "tuned" so as to provide maximum efficiency and efficacy of the two processes when they are both present in a given system. It will be readily apparent that other values (and in fact parameters) may be substituted depending on the particular application(s) in which they are applied.

Tonometric Pressure Velocity and Acceleration Triggers used with first process 100:

POS_VEL_TRIGGER=45 mmHg:

(45 mmHg/3 samples)*(160 Sample/1 Second)=2400 mmHg/sec

NEG_VEL_TRIGGER=−20 mmHg:

(−20 mmHg/3 samples)*(160 Sample/1 Second)− 1067 mmHg/sec

POS_ACCL_TRIGGER=15 mmHg:

(15 mmHg/3 samples)*(160 Sample/1 $Second^2$)=800 $mmHg/sec^2$

NEG_ACCEL_TRIGGER=−12 mmHg:

(−12 mmHg/3 samples)*(160 Sample/1 $Second^2$)=640 $mmHg/sec^2$

MEAN_PRESSURE_CHANGE_TRIGGER=8 mmHg (ii) Event trigger comparison of tonometric mean and pulse pressures of first process 100:

PULSE_RANGE_PERCENT=10; a 10% decrease in decrease in tonometric pulse pressure triggers a limited pressure sweep (fourth state 105).

MEAN_RANGE_PERCENT=10; a 10% change in tonometric mean pressure and +/−8 mmHg change in mean pressure triggers a limited pressure sweep (fourth state 105).

Note that the second process 200 is in the exemplary embodiment made active when first process 100 is active in either the first state 102, second state 103, or third state 104 of the first process 100. The Assignee hereof has also determined that under certain circumstances, scrubbing or elimination of the beats immediately surrounding a first process event from use in the second process 200 may be helpful, since the measurement of mean pressure and pulse pressure for beats surrounding the process event are corrupted.

Additionally, the exemplary embodiment renders the second process 200 inactive when the first process 100 is active in its fourth state 105. The applanation motor position variable is set to the target position upon entry into this fourth state 105, and the second process 200 is reinitialized upon return of the first process 100 from its fourth state 105 to its first state 102.

The second process 200 can also be called from within the first process 100 using any one of a number of well known software call routines in response to each new heart beat, and in concert with the previously described first process states 102-105 and initializations.

Additionally, the tonometric pressure velocity and acceleration triggers (i.e., POS_VEL_TRIGGER, NEG_VEL_TRIGGER, POS_ACCL_TRIGGER, and NEG_ACCEL_TRIGGER) associated with the first process 100 can be increased to provide a larger buffer between normal physiologic changes in pressure and trigger levels, as follows: POS_VEL_TRIGGER=50 mmHg; NEG_VEL_TRIGGER=−25 mmHg; POS_ACCL_TRIGGER=20 mmHg; and NEG_ACCEL_TRIGGER=−15 mmHg.

Furthermore, the checks of beat-to-beat changes in mean pressure previously described with respect to the first process 100 may be eliminated when the two processes 100, 200 are used concurrently. These mean pressure checks are designed primarily for use as protection against slow changes in mechanical coupling (via periodic sweep-calibration) when the first process 100 is used in a stand-alone configuration (i.e., without the presence of the second process 200). The presence of the second process 200 obviates the need for this component, and thereby also possible false first process events caused by arrhythmias (i.e. pulsus alternans) and other physiologic events.

Concurrent use of the first and second processes 100, 200 also advantageously allows more frequent use of "tuning" comparisons between pre- and post-event values of tonometrically measured mean and pulse pressures associated with the first process 100. This feature reduces the frequency of periods where disabling or freezing of the display of current pressure is required to perform the limited applanation sweeps, by simply allowing the second process 200 to recover from these smaller changes in mechanical coupling. Exemplary values are as follows: PULSE_RANGE_PERCENT=20; and MEAN_RANGE_PERCENT=20.

It will also be recognized that while the foregoing exemplary embodiment of the second process 200 is interactive with the first process 100, the second process may operate independently of the first. For example, the second process may be used to adjust and/or maintain the desired applanation level (or position in the case of lateral and proximal cases) irrespective of the methodology used to initially determine the optimal applanation/position. In effect, the second process 200 of the invention used without the first process 100 will hunt and eventually converge on the optimal position itself. This approach, however, has been found by the Assignee hereof to be less temporally efficient than the approach previously described (i.e., determining optimal using the initial sweep process), but may none-the-less be desirable in certain circumstances where hardware/software simplicity can be traded for longer acquisition and settling times. Hence, the present invention should in no way be considered to be restricted to embodiments wherein both first and second processes 100, 200 are employed.

Third Process

Referring now to FIGS. 4a-4d, the third process of the exemplary embodiment of the present invention is described.

During patient monitoring mode, the second process 200 previously described is capable of controlling the applanation of the sensor/pad against the subject artery and overlying tissue, thereby compensating for slow changes (drifts) in the mechanical coupling between the sensor/pad and the underlying tissue. Furthermore, the second process 200 can be most effective over applanation ranges where the pulse pressure is strong (higher signal-to-noise ratio), which exist near the optimal applanation position. However, for large shifts in the mechanical coupling between sensor/pad and the tissue (i.e. flexing of the wrist), the second process 200 may require several minutes to applanate to the proper level to maximize tonometric pulse pressure. Thus, an opportunity exists to improve the performance of the system as a whole by detecting shifts in mechanical coupling that would incur an extended recovery period, and implement a more direct recovery process. The exemplary embodiment of the third process 400 shown in FIG. 4a-4c therefore takes a recovery "shortcut" as it were in those limited circumstances where recovery via the second process 200 would require an undesirably long time.

Thus, an important goal of the third process 400 of the present invention is to detect rapid shifts in mechanical coupling that induce sizeable error in pulse pressure and/or diastolic pressure, and implement an optimal recovery approach.

In a first exemplary embodiment, the third process 400 is operated in conjunction with the first process 100 previously described. Specifically, the third process 400 operates during the first state 102 of the first process 100 (see FIG. 1), and triggers the fourth state 105 when an appreciable shift in the mechanical coupling is detected. Advantageously, the approach to detecting rapid shifts in coupling described herein does not require any significant mechanical or electrical changes to the system. The approach is based on identifying changes in tonometric pressure over a comparatively short period of time that jointly are of the nature and degree to not likely occur physiologically. Such changes also indicate that the second process 200 might require significant time to properly recover. For example, when a patient's diastolic pressure increases, pulse pressure typically remains constant (or increases). Thus, detecting changes in pressure where diastolic pressure increases and pulse pressure decreases significantly over a short time period can be used to detect rapid shifts in mechanical coupling. Furthermore, episodes where the pulse pressure either remains constant or increases are not problematic regardless of the change in diastolic pressure. Since the pulse pressure remains very strong, the probability that the second process 200 can adjust the applanation level (if necessary) within a reasonable period of time remains high.

Figure 4B:
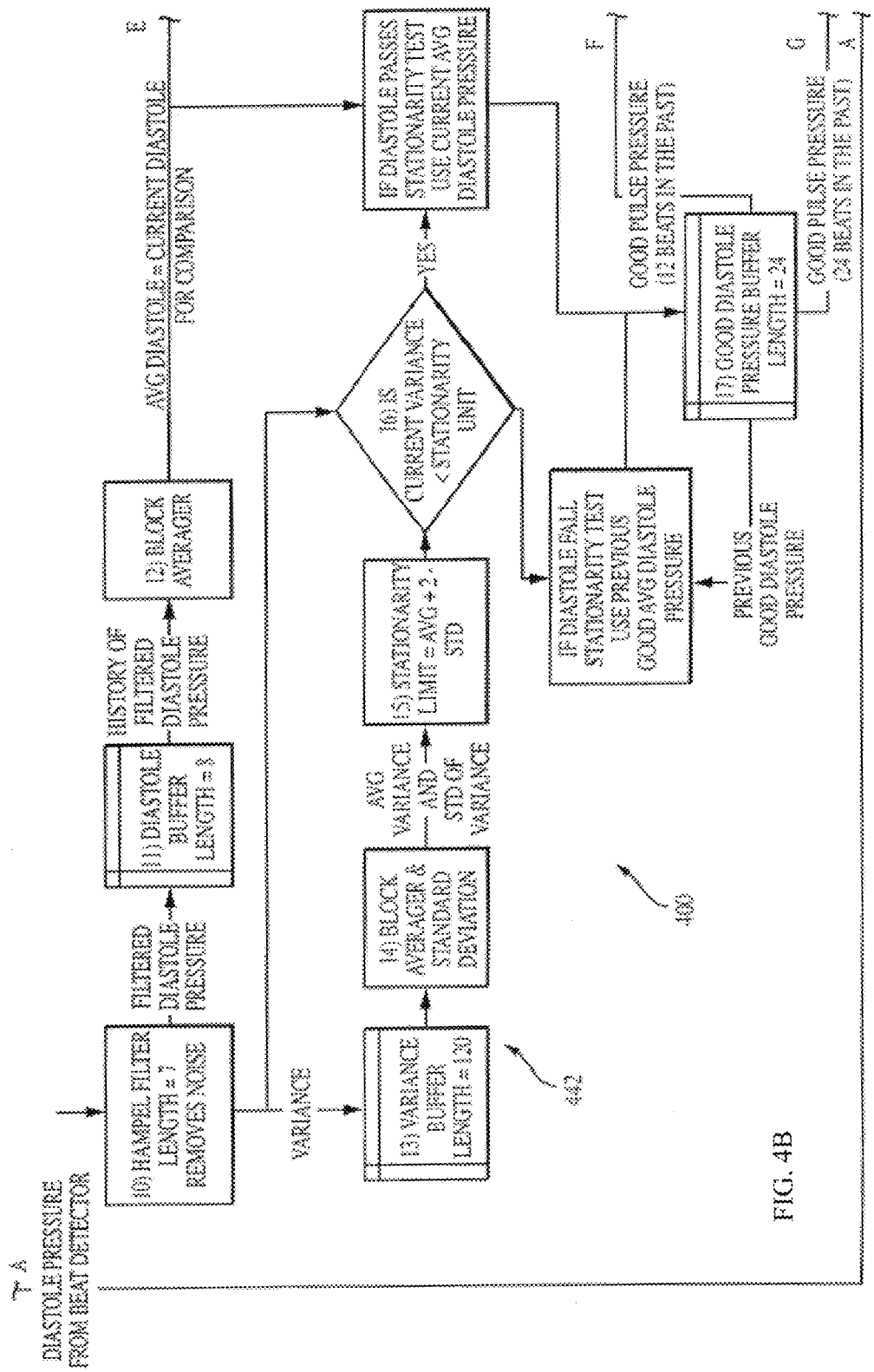
Figure 4C:
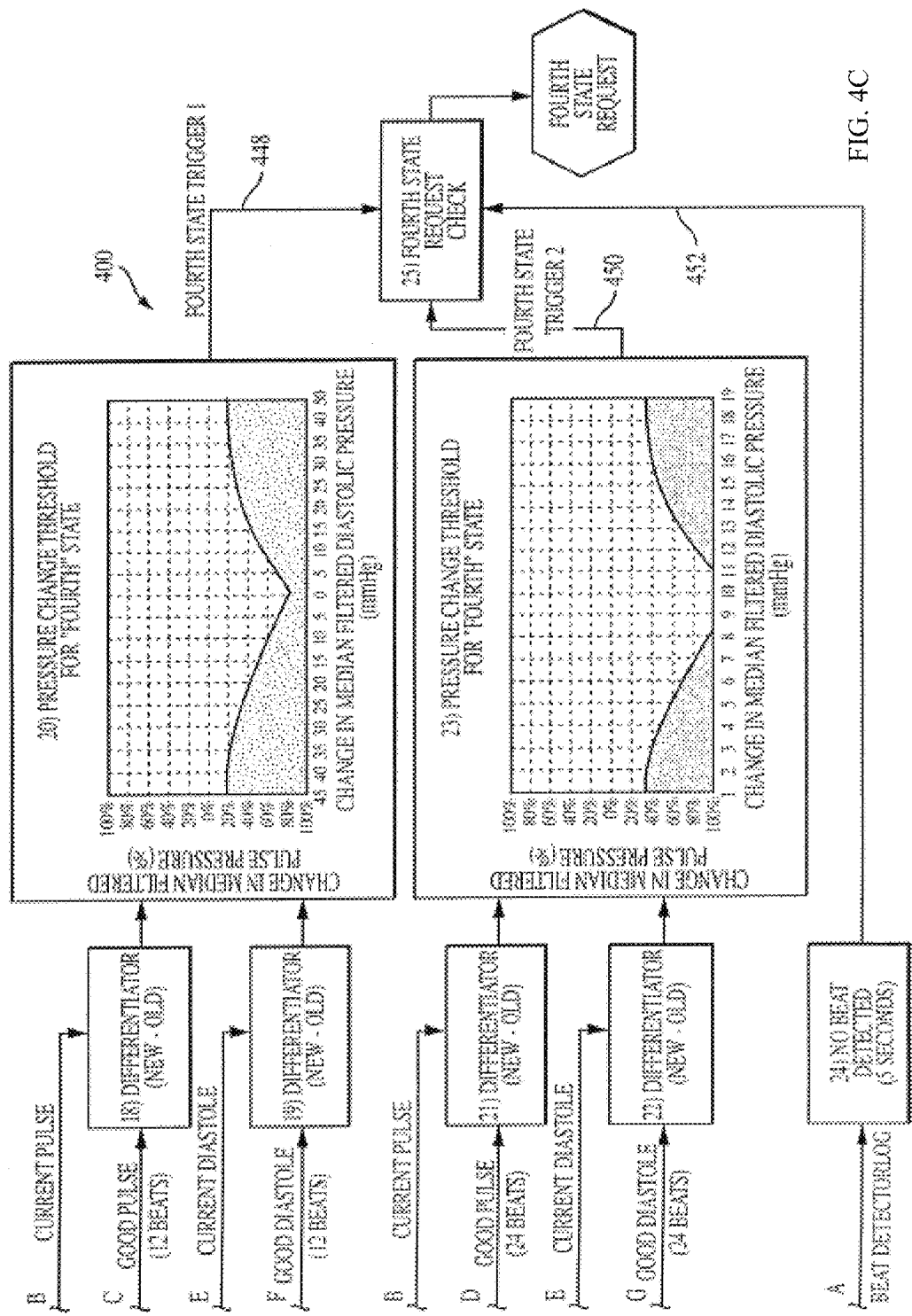

In the exemplary embodiment of FIG. 4a-4c, the process for detecting rapid shifts in mechanical coupling (third process 400) employs one or more metrics for detecting joint shifts in parameters. In the illustrated embodiment, diastolic pressure and pulse pressure are used as the referenced parameters, although it will be appreciated that other parameters (physiologic or otherwise) may be substituted consistent with the invention.

Figure 4D:
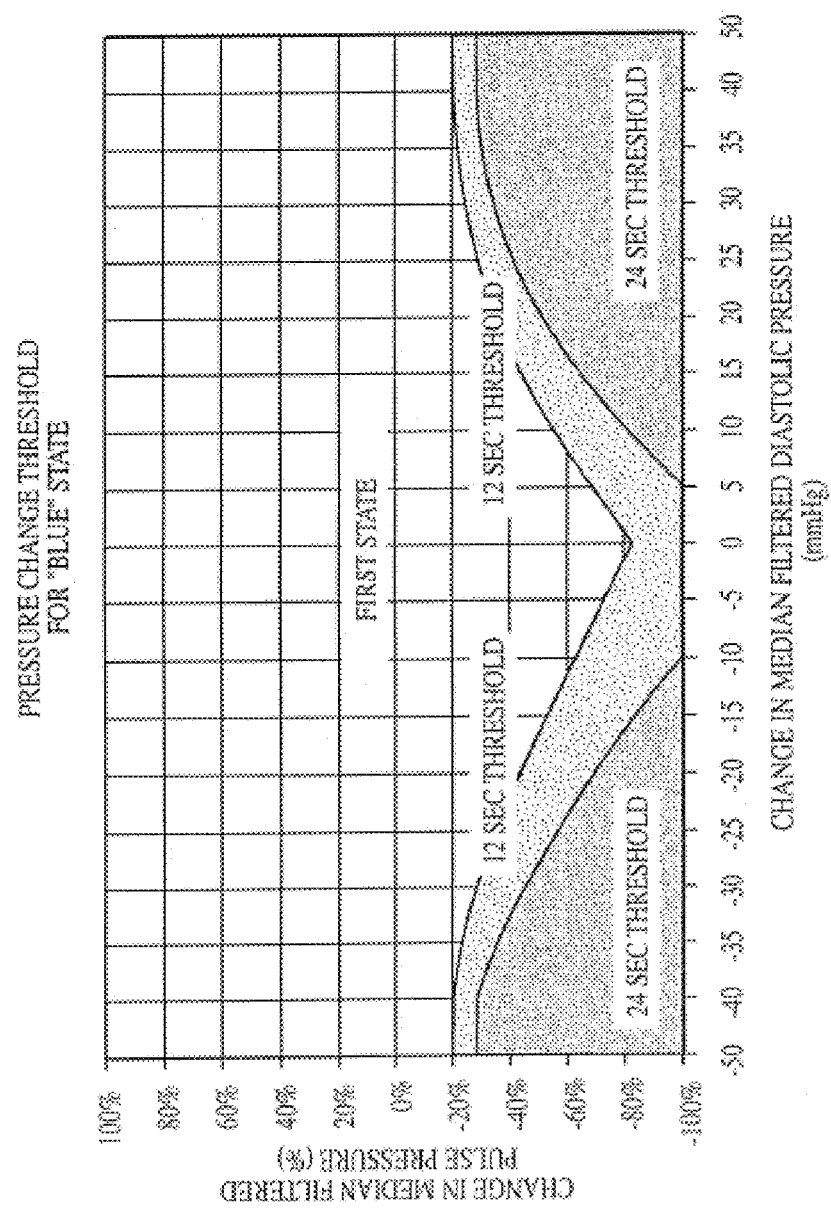

On exemplary scheme for detecting rapid shifts in mechanical coupling is depicted in FIG. 4d. The process 400 investigates changes in the current block averaged pulse and diastolic pressures from "qualified" block averaged pulse and diastolic pressures from moving windows (e.g., both 12 beats and 24 beats in the past in the illustrated embodiment). If the pulse pressure decreases and diastolic pressure deviates from the previous diastolic pressures (12 or 24 beats past), then fourth state 105 of the first process 100 is triggered.

Note that FIG. 4d depicts a percentage change in pulse pressure (the selected parameter). Calculations may also be performed based upon change in absolute blood pressure (mmHg), where for example 40 mmHg is equivalent to 100% and should trigger the fourth state 105 if either the percent change or absolute change in pulse pressure in conjunction with the change in diastolic pressure exceeds the prescribed thresholds. It will be recognized, however, that other triggering criteria and schemes may be utilized if desired. Such alternate criteria and schemes may even be made specific to individual patients or groups of patients, based for example on historical or anecdotal data or other indicia.

The operation of the exemplary embodiment of the rapid shift detection algorithm according to the present invention is now described in detail. As shown in FIGS. 4a-4c, the algorithm of this embodiment is based upon the waveform-restored but unsealed beat pressure diastolic and pulse pressure algorithms. The pulse pressure and diastolic beat pressure data are in this embodiment processed through similar (yet not identical) parallel sub-processes to calculate current and past pressure data for use in the aforementioned threshold determinations of the third process 400. A primary difference between these two sub-processes is that in the first sub-process 440, drops in pulse pressure are of most concern, whereas in the second sub-process 442 changes in diastolic pressure are considered. Exemplary embodiments of these sub-processes 440, 442 are now described in greater detail, although it will be appreciated that other parameters (e.g., besides pulse pressure and diastolic pressure) may be used as the basis for rapid shift detection, and/or other specific configurations of these sub-processes may be substituted.

Furthermore, while the exemplary algorithms and functionality are described in terms of first-in-first-out (FIFO) buffers, other buffering arrangements may be utilized depending on the desired functionality for a given application. For example, under certain circumstances, it may be desirable to replace portions of data in a LIFO (last-in-first-out) manner. Alternatively, "intelligent" (e.g., algorithmically driven) queuing and de-queuing of data may be incorporated.

All such alternate approaches are readily implemented by those of ordinary skill in the data processing arts, and accordingly not described further herein.

i) Pulse Pressure Sub process (Pre-filtering and Averaging)—The following pre-filtering and averaging features are employed in the exemplary embodiment of the first sub-process 440 used in analyzing pulse pressure:

a. Hampel Filter—A Hampel filter (length 7) of the type previously described is used to remove abhorrent pulse pressure values from subsequent calculations, as shown in Eqn. 6 below. Note that a by-product of the exemplary Hampel Filter is the calculation of variance among the pulse pressures over the last 7 beats. This information is used subsequently to determine if the current pulse pressure should be included in the "acceptable" pulse pressure circular buffer.

$$PP_h(k) = \text{Hampel Filter}(PP(k), PP(k-1), PP(k-2), \ldots PP(k-6)) \quad \text{(Eqn. 6)}$$

where k represents the current beat number, $PP_h(k)$ is the Hampel filtered pulse pressure, and $PP(k)$ is the current unfiltered pulse pressure.

Furthermore, the Hampel filter of the present embodiment also calculates the variance of the data. The variance is a measure of distribution around the mean. It is computed as the average squared deviation of each number from its mean, as illustrated in Eqn. 7:

$$PP_{var}(k) = ((PP(k)-u)^2 + (PP(k-1)-u)^2 + ((PP(k-6)-u)^2)/7, \quad \text{(Eqn. 7)}$$

where k represents the current beat number, $PP_{var}(k)$ is the variance of the pulse pressure over the last 7 beats, and u is the average unfiltered pulse pressure for the last 7 beats.

b. Pulse Buffer—A pulse buffer (length=8 in the exemplary embodiment) is a circular buffer containing the Hampel-filtered pulse pressure values. With each beat, the oldest beat is replaced with the most recent Hampel-filtered data.

c. Block Averager—A block averaging routine calculates the mean of the Hampel-filtered pulse pressure data stored in the aforementioned pulse buffer, as illustrated by Eqn. 8 below.

$$\underline{PP}_h(k) = [PP_h(k) + PP_h(k-1) + \ldots + PP_h(k-7)]/8 \quad \text{(Eqn. 8)}$$

where $\underline{PP}_h(k)$ is the block averaged Hampel filtered pulse pressure data.

ii) Pulse Pressure Sub-process (Determining Current Pulse Pressure)—The following features are utilized in the present embodiment of the pulse pressure sub-process 440 for determining the current pulse pressure:

a. Maximum—This feature of the algorithm determines the maximum difference between the current pulse pressure and the block averaged Hampel-filtered pulse pressure data, as shown below in Eqn. 9. This maximum is used in subsequent analysis as the Current Pulse Pressure variable.

If $(\underline{PP}_h(k) PP_{max}[k] = \underline{PP}_h(k)$

Else $PP_{max}[k] PP_h(k)$ \quad (Eqn. 9)

where $PP_{max}[k]$ is used in subsequent comparisons to detect shifts in mechanical coupling. Note that the trigger for the fourth state 105 of the first process 100 is, in the illustrated embodiment, dependant on a significant decrease in pulse pressure. Thus, under conditions where the average pulse pressure is small, the system should not trigger if the pulse pressure from the last beat is large.

iii) Pulse Pressure Sub process (Determining Past Qualified Pulse Pressures)—The following features are used in the present embodiment for determining past (e.g., 12 & 24 beat) qualified pulse pressure values.

a. Variance Buffer—In the exemplary embodiment, a variance buffer (e.g., length=120) comprises a circular buffer containing the variance in the pulse pressure for the last "x" (e.g. 7) beats, as calculated within Hampel filter operation. With each beat, the data of the oldest beat is replaced with the most recent variance.

b. Block Averager and Standard Deviation—These features calculate the mean pressure for the variance in the Hampel filtered pulse pressure data stored in the buffer, as illustrated in Eqns. 10 and 11 below, respectively. With the buffer length set at a comparatively large value (e.g., 120), these calculations provide a statistical benchmark for typical average and range of variance observed for the blocks of pulse pressure data. Output of these algorithms is both block average and standard deviation (or alternatively an equivalent measure that will enable detection of pulse pressures that are not within normal limits of the average mean pressure for the last number of beats n, where n=120 in the present embodiment).

$$\underline{PP}_{var}(k) = [PP_{var}(k) + PP_{var}(k-1) + \ldots + PP_{var}(k-119)]/120 \quad \text{(Eqn. 10)}$$

where $\underline{PP}_{var}(k)$ is the block averaged Hampel filtered pulse pressure data.

$$SD_{PPvar}(k) = (((PP_{var}(k) - \underline{PP}_{var}(k))^2 (PP_{var}(k-1) - \underline{PP}_{var}(k))^2 + \ldots + ((PP_{var}(k-119) - \underline{PP}_{var}(k))^2)/120)^{1/2} \quad \text{(Eqn. 11)}$$

where $SD_{PPvar}(k)$ is the standard deviation in the Pulse Pressure Variance data.

c. Stationarity Limit—The stationary limit feature calculates an upper limit of the pulse pressure variance or standard deviation that permits the current block (e.g., 7 beats) average pulse pressure to be included in the history of "qualified" pulse pressure values for future comparisons. One exemplary approach comprises comparing the variance of the current pulse pressure block with the value (average pulse pressure+1 standard deviation of the variances observed over the last 120 beats), which constitutes the upper limit of acceptable pulse pressures variance, as shown in Eqn. 12 below:

$$StationarityLimit_{PP}(k)=\underline{PP}_{var}(k)+SD_{PPvar}(k) \quad (Eqn. 12)$$

Note, however, that other methods of determining an upper limit for the observed variance may readily be substituted or used in conjunction with the foregoing. For example, analysis of the current variance (e.g., current variance <$40^{th}$ largest out of 120 beats) may be utilized. It will be recognized that the aforementioned median filter can be easily modified to recursively determine this value. Other configurations may also be employed consistent with the invention, such configurations being readily determined by those of ordinary skill.

d. Identification of Pulse Pressure value to be included in Pulse Pressure History Buffer—The exemplary embodiment of the invention further includes functionality which determines whether the current average pulse pressure value or most recent acceptable pulse pressure value should be added to the circular buffer containing a history of average pulse pressures, as shown in Eqn. 13 below. This is accomplished using the stationarity limit calculated previously.

$$If(PP_{var}(k)>\\ \underline{PP}_{var}(k)SD_{PPvar}(k))PPhistory(k)=PPhistory(k-1)$$

$$Else\ PPhistory(k)=\underline{PP}_h(k) \quad (Eqn. 13)$$

where PPhistory(k) is the history of "acceptable" Pulse Pressures e. Update Pulse Pressure History Buffer—In the exemplary embodiment, a pulse pressure history FIFO buffer (e.g., length=24) is employed. The history buffer comprises a circular buffer containing the history of past "acceptable" average pulse pressure values. With each beat, the data associated with oldest beat is replaced with that of the most recent. Values which are a prescribed number of beats in the past (e.g., 12 and 24 beats) from this array are used in subsequent calculations to determine the change in pulse pressure over this period.

iv) Diastolic Pressure Sub process (Pre-filtering and Averaging)—The following pre-filtering and averaging features are employed in the exemplary embodiment of the first sub-process 440 used in analyzing pulse pressure:

a. Hampel Filter—The exemplary embodiment of the diastolic sub-process 442 uses a Hampel filter (e.g., length 7) to remove abhorrent diastolic pressure values from subsequent calculations, similar to the pulse pressure sub-process 440 (see Eqn. 14 below). A by-product of the Hampel Filter is the calculation of the variance of diastolic pressure over the previous number (e.g., 7) of beats. This information is used subsequently to determine if the current diastolic pressure should be included in the "acceptable" diastolic pressure circular buffer.

$$D_h(k)=Hampel\ Filter\{D(k),D(k-1),D(k-2),\ldots,\\ D(k-6)\} \quad (Eqn. 14)$$

where k represents the current beat number, $D_h(k)$ is the Hampel filtered diastolic pressure, and D(k) is the current unfiltered diastolic pressure. Furthermore, the Hampel filter also calculates the variance of the data, as shown in Eqn. 15:

$$D_{var}(k)=((D(k)-u)^2+(D(k-1)-u)^2+\ldots+((D(k-6)-\\ u)^2)/7, \quad (Eqn. 15)$$

where k represents the current beat number, $D_{var}(k)$ is the variance of the diastolic pressure over the last 7 beats, and u is the average diastolic pressure over the last 7 beats.

b. Pulse Buffer—A FIFO pulse buffer of a determinate length (e.g., length=8) is used in the present embodiment; this buffer comprises a circular buffer containing the Hampel filtered diastolic pressure values. With each successive beat, the data for the oldest beat is replaced with the most recent Hampel filtered data.

c. Block Averager—A block averaging routine is used to calculate the mean for the Hampel filtered diastolic pressure data stored in the buffer, as shown in Eqn. 16 below:

$$\underline{D}_h(k)=[D_h(k)+D_h(k-1)+\ldots+D_h(k-7)]/8 \quad (Eqn. 16)$$

where $\underline{D}_h(k)$ is the block averaged Hampel filtered Diastolic pressure data.

v) Diastolic Pressure Sub process (Current Value Determination)—The diastolic sub-process 442 determines the current value of the diastolic pressure using a straightforward methodology. Specifically, the current diastolic pressure is simply the most recent block averaged Hamper-filtered diastolic pressure value. Note that the trigger for the fourth state 105 of the first process 100 is dependant on a significant change in diastolic pressure.

vi) Diastolic Pressure Sub process (Determining Past Qualified DiastolicPressures)—The sub-process 442 also contains mechanisms for determining past qualified diastolic pressures (e.g., those of 12 and 24 beats past), as follows:

a. Variance Buffer—A FIFO variance buffer of determinate length (e.g., length=120) comprising a circular buffer containing the variance in the diastolic pressure for the last 7 beats (as calculated within Hampel filter operation) is used in the present embodiment of the diastolic sub-process 442. With each beat, the variance of the oldest beat is replaced with the most recent variance.

b. Block Averager and Standard Deviation—These functions calculate the mean for the variance in the Hampel-filtered diastolic pressure data stored in the variance buffer. With the buffer length set at a comparatively large value, these calculations provide a statistical benchmark for the typical average and the range of variance observed for the blocks of pulse pressure. Output from these processes is both block average and standard deviation (or an equivalent measure) that will enable detection of pulse pressures that are not within normal limits of the average mean pressure for the last "n" beats), as shown in Eqns. 17 and 18 below (for n=120):

$$\underline{D}_{var}(k)=[D_{var}(k)+D_{var}(k-1)+\ldots+D_{var}(k-119)]/120 \quad (Eqn. 17)$$

$$SD_{Dvar}(k)=(((D_{var}(k)-D_{var}(k))^2+(D_{var}(k-1)-D_{var}(k))^2+\ldots+((D_{var}(k-119)-\underline{D}_{var}(k))^2)/119)^{1/2} \quad (Eqn. 18)$$

where $\underline{D}_{var}(k)$ is the block averaged Hampel filtered diastolic pressure data.

c. Stationarity Limit—The stationary limit function of the diastolic sub-process 442 calculates an upper limit of the diastolic pressure variance (or standard deviation) that permits the average diastolic pressure of the current block of data (e.g., 7 beats-worth) to be included in the history of diastolic pressure values for use in future comparisons, as shown in Eqn. 19: (Eqn. 19)

$$StationarityLimit_D(k)=\underline{D}_{var}(k)+/-SD_{Dvar}(k) \quad (Eqn. 19)$$

d. Identify Diastolic Pressure value to be included in Diastolic Pressure History Buffer—Using the stationarity limit previously calculated, this feature of the diastolic sub-process 442 determines whether the current average diastolic pressure value or most recent "acceptable" diastolic pressure value should be added to the circular buffer containing a history of average pulse pressures. If the new Diastolic Pressure is within limits of the stationarity limit described above, then it is included in the diastolic pressure history, else the most recent diastolic pressure history value is duplicated.

e. Update Diastolic Pressure History Buffer—In the exemplary embodiment, the diastolic subprocess 442 includes a circular FIFO buffer of determinate length (e.g., length=24) containing the history of past "acceptable" average diastolic pressures. With each beat, the data associated with the oldest beat is replaced with that of the most recent. Values derived from one or more past beats (e.g., 12 and 24 beats in the past from the current array) are used in subsequent calculations to determine the change in pulse pressure over the period of interest, as shown in Eqn. 20 below:

If$(D_{var}(k) > \underline{D}_{var}(k) SD_{Dvar}(k))D$history$(k) = D$history$(k-1)$ Else $D$history$(k) = \overline{D}_h(k)$  (Eqn. 20)

vii) Analysis for Detection of Shifts in Mechanical Coupling a. Threshold detection—In order to detect rapid shifts in mechanical coupling, the third process 400 of the invention performs threshold detection over the prior first number (e.g., 12) of beats in the exemplary embodiment as follows:

1) Pulse Pressure Difference—The third process 400 calculates the difference between the current pulse pressure (Current Pulse Pressure variable referenced with respect to Item ii.a. of the pulse pressure sub-process 440 above) and the first number (e.g., 12) of qualified pulse pressure beats in the past (stored in the circular history buffer by the pulse pressure sub-process 440 as previously described in iii.d. above). This calculation is shown in Eqn. 21 below:

PulsePressureDifference12=PP$_{max}$[k]-PPhistory(12)  (Eqn. 21)

2) Diastolic Difference—The third process 400 calculates the difference between the current diastolic pressure (output from the diastolic sub-process block averager as described above) and the qualified diastolic pressure for, e.g., 12 beats in the past (stored in the circular history buffer by the diastolic sub-process as described in Item vi.d. above), as shown in Eqn. 22:

DiastolicPressureDifference12=$\underline{D}_h(k)$-Dhistory(12)  (Eqn. 22)

3) Detector—In accordance with the temporal threshold shown in FIG. 4d, if the pulse pressure difference (Item vii.a.1) above) is sufficiently negative, and the diastolic pressure difference (Item vii.a.2) above) is sufficiently different from zero, then a "Trigger 1" value 448 associated with the fourth state 105 of the first process 100 is set to TRUE.

b. Additionally, the third process 400 of the invention performs threshold detection over the prior second number (e.g., 24) of beats in the exemplary embodiment as follows:

1) Pulse Pressure Difference—The third process 400 calculates the difference between the current pulse pressure (Current Pulse Pressure variable referenced above) and the qualified second number (e.g., 24) of pulse pressure beats in the past (stored in the circular history buffer by the pulse pressure sub-process 440 as previously described), as shown in Eqn 23 below:

PulsePressureDifference24=PP$_{max}$[k]-PPhistory(24)  (Eqn. 23)

2) Diastolic Difference: Calculates the difference between the current diastolic pressure (as previously described) and the qualified diastolic pressure 24 beats in the past, as illustrated by Eqn. 24 below:

DiastolicPressureDifference24=$\underline{D}_h(k)$-Dhistory(24)  (Eqn. 24)

3) Detector—In accordance with the temporal (e.g., 24 second) threshold shown in FIG. 4d, i the pulse pressure difference (Item vii.b.1) above) is sufficiently negative, and the diastolic pressure difference (Item viii.b.2) above) is suf-ficiently different from zero, then the "Trigger 2" value 450 for the fourth state 105 of the second process is set TRUE.

c. Beat Evaluation over Most Recent Period—Additionally, the third process 400 of the present invention is optionally configured to evaluate beats detected within a prior interval (e.g., prior five seconds), as follows:

1) No beat detected during interval—If a beat of acceptable quality has not been detected over the interval and "noise" on the pressure signal has not caused the lack of a good beat, then the "Trigger 3" value 452 for the fourth state 105 is set TRUE.

d. Fourth State Request Check—The third process 400 performs a logic check based on the presence of a Trigger 1, Trigger 2, or Trigger 3 value 448, 450, 452 set to TRUE. If any of the aforementioned Triggers are set TRUE, and the first process 100 is in the first state 102, then the first process 100 should enter the fourth state 105 (i.e., accelerated recovery). All fourth state Triggers 448, 450, 452 are then reset to FALSE.

Note that if the first process 100 is in either the second state 103 or third state 104, the proper new state option is subsequently determined. Alternatively, if the first process is currently in the fourth state 105, then the aforementioned request to enter the fourth state 105 is ignored.

It will be recognized that while the foregoing embodiment of the third process methodology addresses the problem of identifying rapid shifts in mechanical coupling based on a substantially probabilistic approach (which is tailored using an understanding of common changes in a patient's arterial pressure during the course of various physiologic events), this approach does not measure directly (or even indirectly) changes in the mechanical coupling between the tonometric pressure sensor and its associated contact pad and the underlying tissue. Accordingly, the exemplary implementation of the third process 400 is not immune to error. The second process 200 of the present invention, however, advantageously insulates the system against failure of the third process 400 to detect rapid changes in coupling, since the second process will converge on the optimal level of applanation irrespective of the third process (albeit over a period of several minutes) as previously described. Furthermore, false triggering by the third process 400 (i.e., indication that a rapid coupling change has been experienced when in fact it has not) will induce an applanation sweep, and possibly a lateral/proximal position sweep, which enables the system to recover as well. Hence, any errors associated with the probabilistic implementation of the third process 400 do not adversely affect the accuracy of the system, but rather merely the speed with which it converges on the proper applanation level and/or lateral or proximal position. The exemplary embodiment of the present invention will therefore not generate "bad" data, but rather simply not update data until optimal applanation/position is achieved.

It will also be noted that examination of a patient's data history as described above with respect to the pulse pressure and diastolic sub-processes 440, 442 may encompass examinations of selected segments of the data history for that patient as well as the examination and comparison of segments of data for that patient against comparable data for other patients. Furthermore, the analysis described above may be applied in both historical and/or predictive fashion; for instance, one or more historical data segments may be analyzed via an algorithm which predicts future ranges or values for one or more parameters. If the subsequent measurement of the parameter(s) is not within the prediction, instigation of the applanation/position sweep(s) can then be conducted and the optimal position reacquired. For example, wherein an analysis of the historical data for a patient relating to diastolic pressure indicates that a future measurement within a given time epoch outside the range of 50-80 mmHg would correspond to an unphysical situation or event, any diastolic pressure reading outside that range occurring within r could trigger reacquisition.

It will further be recognized that numerous combinations of analyzed parameters (e.g., systolic, diastolic, pulse, or mean pressure, and combinations or derivations thereof), time periods (historical, historical/predictive, or purely predictive), and acceptance/rejection criteria (e.g., parameter range at a discrete epoch, continuity or variation over time, statistics, etc.) may be utilized either alone or in combination consistent with the present invention to effectuate the goal of maintaining optimal position of the sensor under all operating environments and conditions. All such methods and approaches are readily implemented within the framework of the present invention by those of ordinary skill in the programming and mathematical arts, and accordingly are not described further herein.

System Apparatus for Hemodynamic Assessment

Referring now to FIGS. 5a-5d, an apparatus for measuring hemodynamic properties within the blood vessel of a living subject is now described, In the illustrated embodiment, the apparatus is adapted for the measurement of blood pressure within the radial artery of a human being, although it will be recognized that other hemodynamic parameters, monitoring sites, and even types of living organism may be utilized in conjunction with the invention in its broadest sense.

The exemplary apparatus 500 of FIGS. 5a-5d fundamentally comprises an applanation assembly (including one or more pressure transducers 522) for measuring blood pressure from the radial artery tonometrically; a digital processor 508 operatively connected to the pressure transducer(s) 522 (and a number of intermediary components) for (i) analyzing the signals generated by the transducer(s); (ii) generating control signals for the stepper motor 506 (via a microcontroller 511a operatively coupled to the stepper motor control circuits); and (iii) storing measured and analyzed data. The motor controllers 511, processor 508, auxiliary board 523, and other components may be housed either locally to the applanator 502, or alternatively in a separate stand-alone housing configuration if desired. The pressure transducer 522 and its associated storage device 552 are optionally made removable from the applanator 502.

The pressure transducer 522 is, in the present embodiment, a strain beam transducer element which generates an electrical signal in functional relationship (e.g., proportional) to the pressure applied to its sensing surface 521, although other technologies may be used. The analog pressure signals generated by the pressure transducer 522 are converted into a digital form (using, e.g., an ADC 509) after being optionally low-pass filtered 513 and sent to the signal processor 508 for analysis. Depending on the type of analysis employed, the signal processor 508 utilizes its program either embedded or stored in an external storage device to analyze the pressure signals and other related data (e.g., stepper motor position as determined by the position encoder 577, scaling data contained in the transducer's EEPROM 552 via I2C1 signal, need for reacquisition per FIGS. 4a-4c, etc.).

As shown in FIGS. 5a-5d, the apparatus 500 is also optionally equipped with a second stepper motor 545 and associated controller 511b, the second motor 545 being adapted to move the applanator assembly 502 laterally across the blood vessel (e.g., radial artery) of the subject as described above. A third stepper motor (not shown) and associated controls may also be implemented if desired to control the proximal positioning of the applanation element 502. Operation of the lateral positioning motor 545 and its controller 511b is substantially analogous to that of the applanation motor 506, consistent with the methodologies previously described herein.

As previously discussed, continuous accurate non-invasive measurements of hemodynamic parameters (e.g., blood pressure) are highly desirable. To this end, the apparatus 500 is designed to (i) identify the proper level of applanation of the subject blood vessel and associated tissue; (ii) continuously "servo" on this condition to maintain the blood vessel/tissue properly biased for the best possible tonometric measurement; optionally (iii) scale the tonometric measurement as needed to provide an accurate representation of intravascular pressure to the user/operator; and (iv) identify conditions where transient or "unphysical" events have occurred, and correct the system accordingly to regain the optimal applanation level and lateral/proximal positions.

During an applantion "sweep", the controller 511a controls the applanation motor 506 to applanate the artery (and interposed tissue) according to a predetermined profile. Similarly, the extension and retraction of the applanation element 502 during the later states of the algorithm (i.e., when the applanation motor 506 is disposed at the optimal applanation position, and subsequent servoing around this point) are controlled using the controller 511a and processor 508. Such "servo" control schemes may also be employed with respect to the lateral and proximal motor drive assemblies if desired, or alternatively a more static approach (i.e., position to an optimal initial position, and then reposition only upon the occurrence of an event causing significant misalignment). In this regard, it will be recognized that the control schemes for the applanation motor and the lateral/proximal positioning motor(s) may be coupled to any degree desired consistent with the invention.

The apparatus 500 is also configured to apply the methodologies of the first, second, and third processes 100, 200, 400 previously discussed with respect to FIGS. 1-4, as well as the initial sweep and scaling methodologies described in the aforementioned co-pending patent application Ser. No. 10/072,508 previously incorporated by reference herein. Details of the implementation of these latter methodologies are provided in the co-pending application, and accordingly are not described further herein.

The physical apparatus 500 of FIGS. 5a-5d comprises, in the illustrated embodiment, a substantially self-contained unit having, inter alia, a combined pressure transducer 522 and applanation device 500, motor controllers 511, RISC digital processor 508 with associated synchronous DRAM (SDRAM) memory 517 and instruction set (including scaling lookup tables), display LEDs 519, front panel input device 521, and power supply 523. In this embodiment, the controllers 511 is used to control the operation of the combined pressure transducer/applanation device, with the control and scaling algorithms are implemented on a continuing basis, based on initial operator/user inputs.

For example, in one embodiment, the user input interface comprises a plurality (e.g., two) buttons disposed on the face of the apparatus housing (not shown) and coupled to the LCD display 579. The processor programming and LCD driver are configured to display interactive prompts via the display 579 to the user upon depression of each of the two buttons.

Furthermore, a patient monitor (PM) interface circuit 591 shown in FIGS. 5a-5d may be used to interface the apparatus 500 to an external or third-party patient monitoring system. Exemplary configurations for such interfaces 591 are described in detail in co-pending U.S. patent application Ser. No. 10/060,646 entitled "Apparatus and Method for Interfacing Time-Variant Signals" filed Jan. 30, 2002, and assigned to the Assignee hereof, which is incorporated by reference herein in its entirety, although other approaches and circuits may be used. The referenced interface circuit has the distinct advantage of automatically interfacing with literally any type of patient monitor system regardless of its configuration. In this fashion, the apparatus 500 of the present invention coupled to the aforementioned interface circuit allows clinicians and other health care professionals to plug the apparatus into in situ monitoring equipment already on hand at their facility, thereby obviating the need (and cost) associated with a dedicated monitoring system just for blood pressure measurement.

Figure 5A:
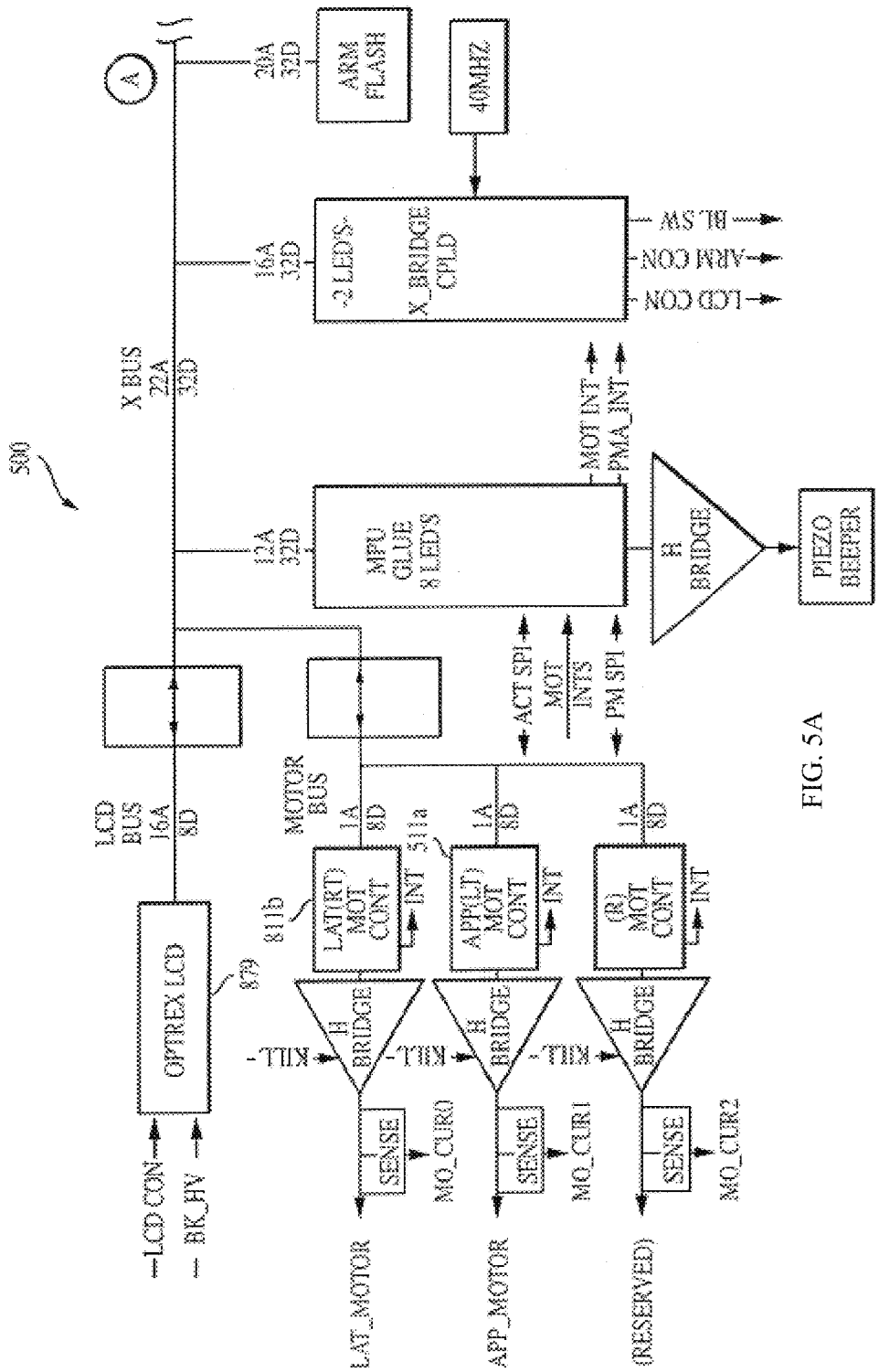
FIG. 5a is a block diagram of one exemplary embodiment of the apparatus for measuring hemodynamic parameters within the blood vessel of a living subject according to the invention.
Figure 5B:
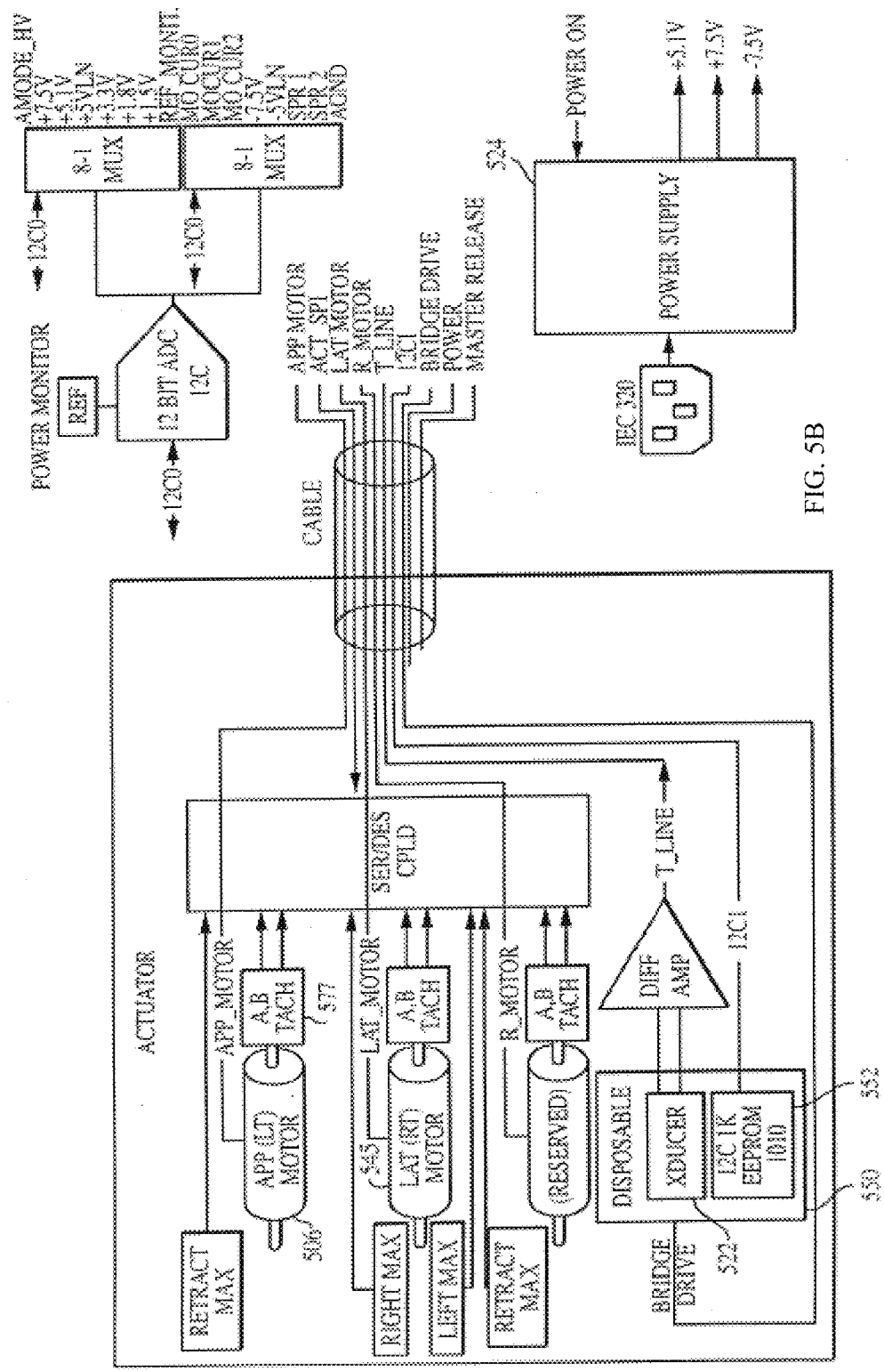
FIG. 5b is a block diagram of one exemplary embodiment of the apparatus for measuring hemodynamic parameters within the blood vessel of a living subject according to the invention.
Figure 5C:
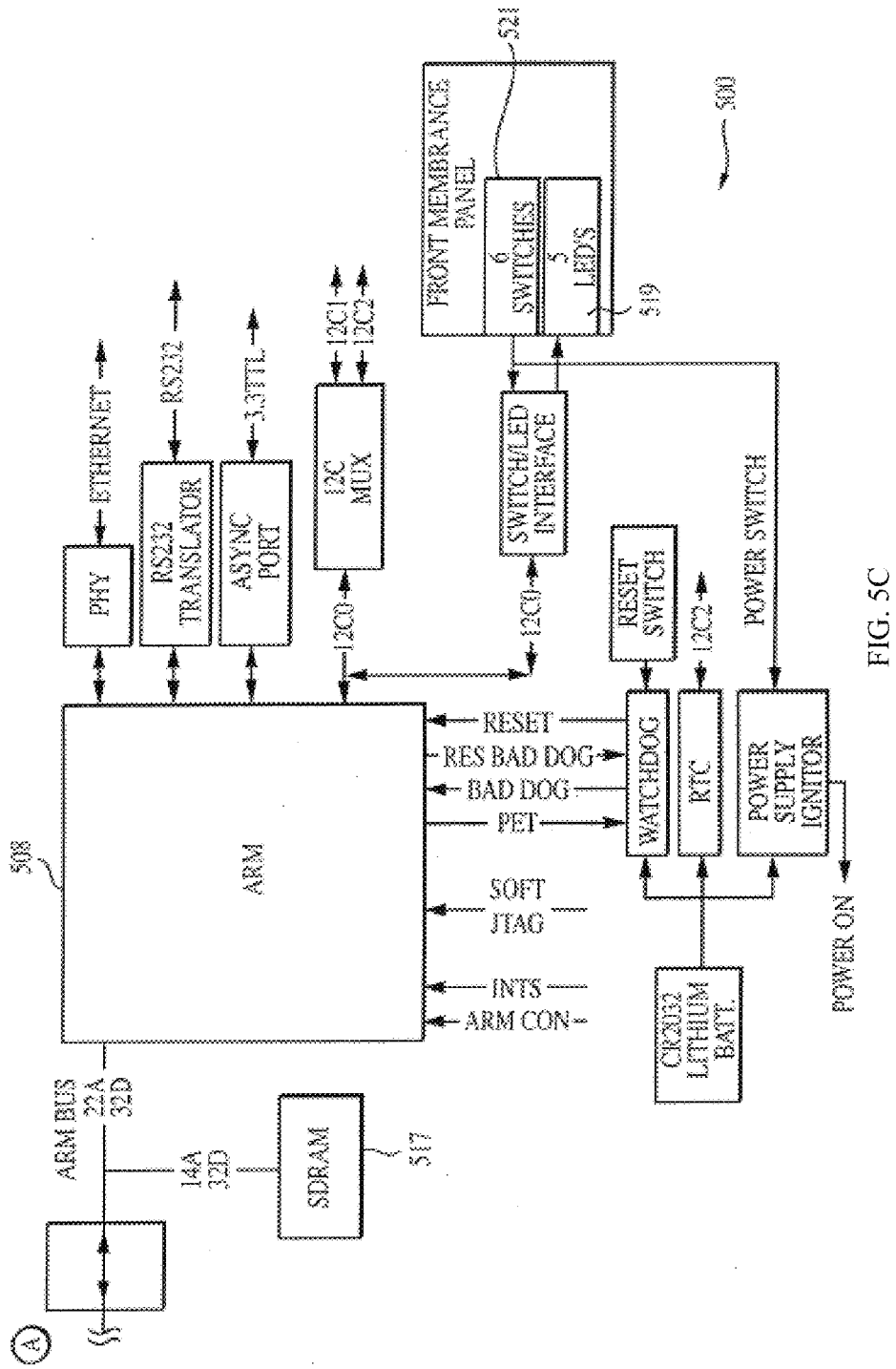
FIG. 5c is a block diagram of one exemplary embodiment of the apparatus for measuring hemodynamic parameters within the blood vessel of a living subject according to the invention.
Figure 5D:
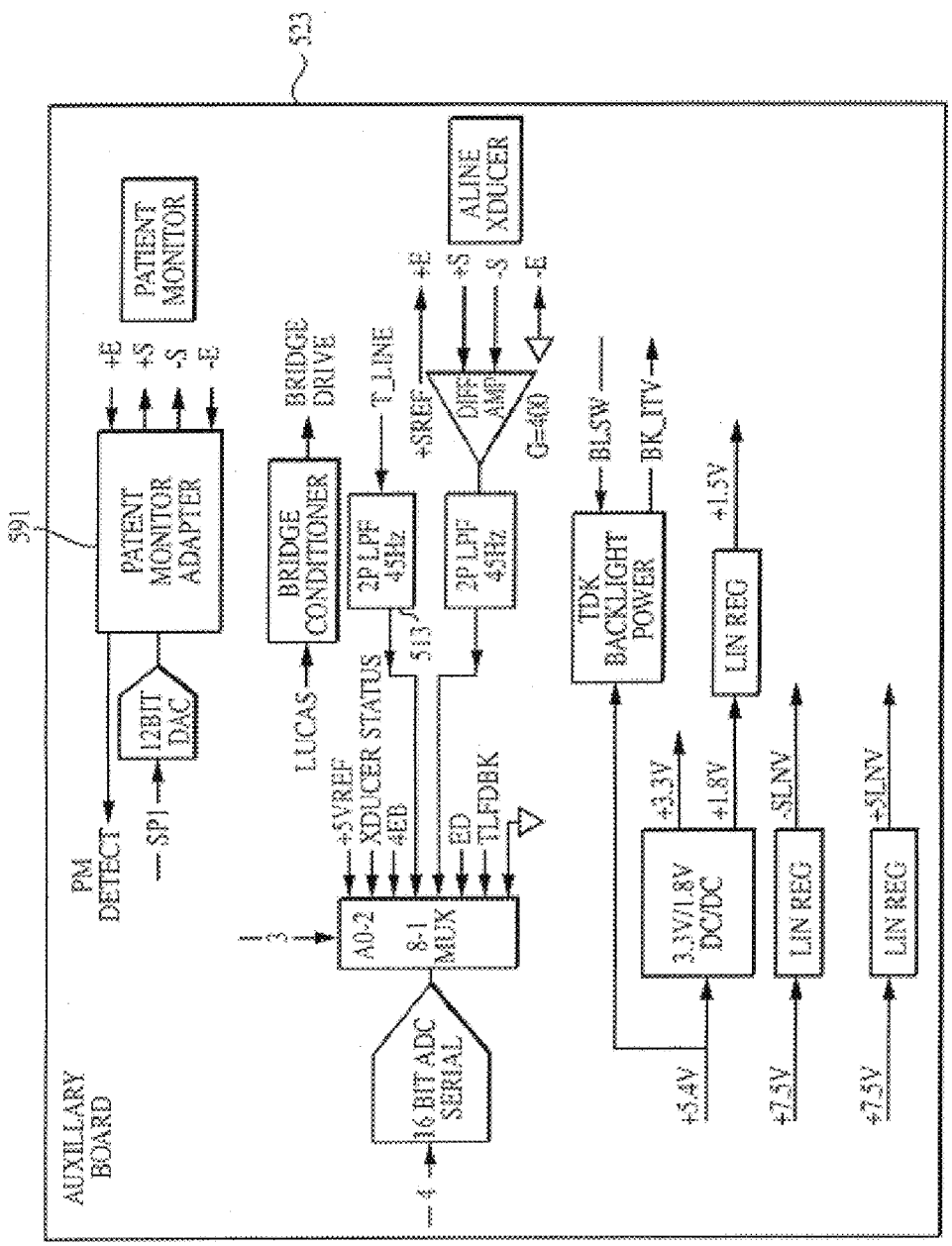
FIG. 5d is a block diagram of one exemplary embodiment of the apparatus for measuring hemodynamic parameters within the blood vessel of a living subject according to the invention.

Additionally, an EEPROM 552 is physically coupled to the pressure transducer 522 as shown in FIGS. 5a5d so as to form a unitary unit which is removable from the host apparatus 500. The details of the construction and operation of exemplary embodiments of such coupled assemblies are described in detail in co-pending U.S. application Ser. No. 09/652,626, entitled "Smart Physiologic Parameter Sensor and Method", filed Aug. 31, 2000, assigned to the Assignee hereof, and incorporated by reference herein in its entirety, although other configurations clearly may be substituted. By using such a coupled and removable arrangement, both the transducer 522 and EEPROM 552 may be readily removed and replaced within the system 500 by the operator.

It is also noted that the apparatus 500 described herein may be constructed in a variety of different configurations, and using a variety of different components other than those specifically described herein. For example, it will be recognized that while many of the foregoing components such as the processor 508, ADC 509, controller 511, and memory are described effectively as discrete integrated circuit components, these components and their functionality may be combined into one or more devices of higher integration level (e.g., so-called "system-on-chip" (SoC) devices). The construction and operation of such different apparatus configurations (given the disclosure provided herein) are readily within the possession of those of ordinary skill in the medical instrumentation and electronics field, and accordingly not described further herein.

The computer program(s) for implementing the aforementioned first, second, and third processes (as well as scaling) are also included in the apparatus 500. In one exemplary embodiment, the computer program comprises an object ("machine") code representation of a C$^{++}$ source code listing implementing the methodology of FIGS. 1-4, either individually or in combination thereof. While C$^{++}$ language is used for the present embodiment, it will be appreciated that other programming languages may be used, including for example VisualBasic™, Fortran, and C$^{+}$. The object code representation of the source code listing is compiled and may be disposed on a media storage device of the type well known in the computer arts. Such media storage devices can include, without limitation, optical discs, CD ROMs, magnetic floppy disks or "hard" drives, tape drives, or even magnetic bubble memory. These programs may also be embedded within the program memory of an embedded device if desired. The computer program may further comprise a graphical user interface (GUI) of the type well known in the programming arts, which is operatively coupled to the display and input device of the host computer or apparatus on which the program is run.

In terms of general structure, the program is comprised of a series of subroutines or algorithms for implementing the applanation and scaling methodologies described herein based on measured parametric data provided to the host apparatus 500. Specifically, the computer program comprises an assembly language/micro-coded instruction set disposed within the embedded storage device, i.e. program memory, of the digital processor or microprocessor associated with the hemodynamic measurement apparatus 500. This latter embodiment provides the advantage of compactness in that it obviates the need for a stand-alone PC or similar hardware to implement the program's functionality. Such compactness is highly desirable in the clinical and home settings, where space (and ease of operation) are at a premium.

Method of Providing Treatment

Figure 6A:
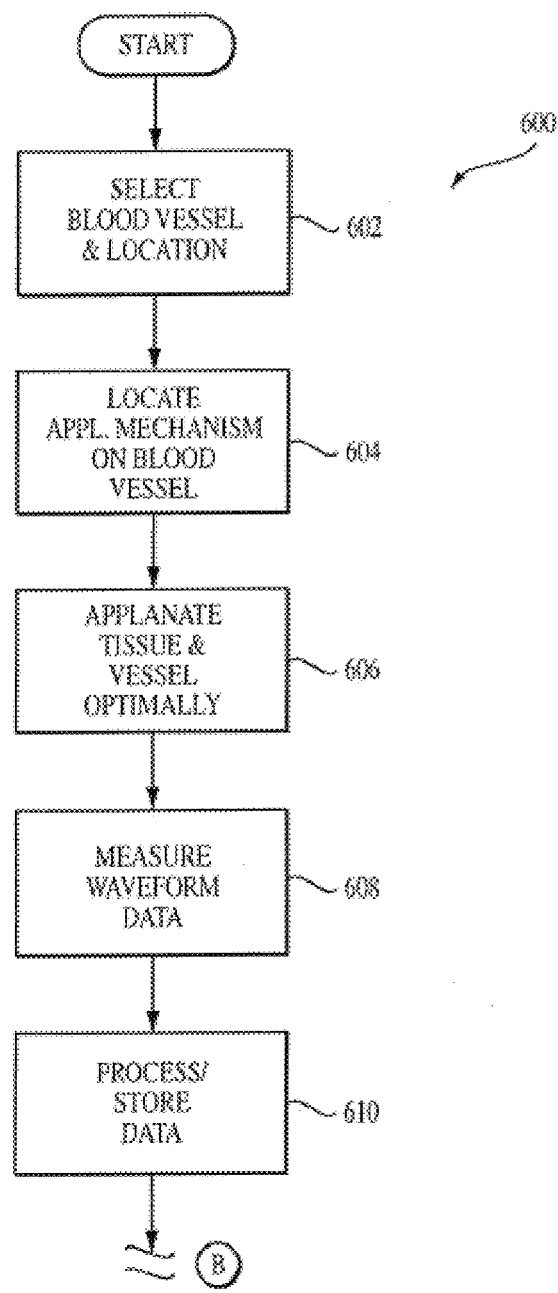
FIG. 6a is a logical flow diagram illustrating one exemplary embodiment of the method of providing treatment to a subject using the aforementioned methods.
Figure 6B:
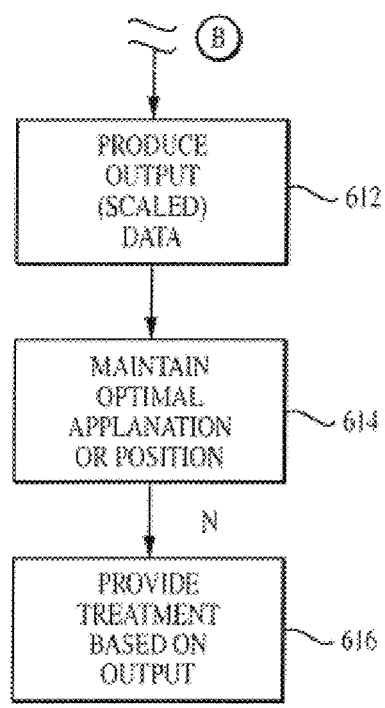
FIG. 6b is a logical flow diagram illustrating one exemplary embodiment of the method of providing treatment to a subject using the aforementioned methods.

Referring now to FIGS. 6a-6b, a method of providing treatment to a subject using the aforementioned methods is disclosed. As illustrated in FIGS. 6a and 6b, the first step 602 of the method 600 comprises selecting the blood vessel and location to be monitored. For most human subjects, this will comprise the radial artery (as monitored on the inner portion of the wrist), although other locations may be used in cases where the radial artery is compromised or otherwise not available.

Next, in step 604, the applanation mechanism 502 is placed in the proper location with respect to the subject's blood vessel. Such placement may be accomplished manually, i.e., by the caregiver or subject by visually aligning the transducer and device over the interior portion of the wrist, by the pressure/electronic/acoustic methods of positioning previously referenced, or by other means. Next, the first applanation element 502 is operated per step 606 so as to applanate the tissue surrounding the blood vessel to a desired level so as to identify an optimal position where the effects of transfer loss and other errors associated with the tonometric measurement are mitigated. Co-pending U.S. patent application Ser. No. 10/072,508 previously incorporated herein illustrates one exemplary method of finding this optimum applanation level.

Once the optimal level of applanation for the applanator element 502 is set, the pressure waveform is measured per step 608, and the relevant data processed and stored as required (step 610). Such processing may include, for example, calculation of the pulse pressure (systolic minus diastolic), calculation of mean pressures or mean values over finite time intervals, and optional scaling of the measured pressure waveform(s). One or more resulting outputs (e.g., systolic and diastolic pressures, pulse pressure, mean pressure, etc.) are then generated in step 612 based on the analyses performed in step 610. The relevant portions of the first, second, and third processes 100, 200, 400 of the present invention are then implemented as required to maintain the subject blood vessel and overlying tissue in a continuing state of optimal or near-optimal compression (as well as maintaining optimal lateral/proximal position if desired) per step 614 so as to provide continuous monitoring and evaluation of the subject's blood pressure. This is to be distinguished from the prior art techniques and apparatus, wherein only periodic representations and measurement of intra-arterial pressure are provided.

Lastly, in step 616, the "corrected" continuous measurement of the hemodynamic parameter (e.g., systolic and/or diastolic blood pressure) is used as the basis for providing treatment to the subject. For example, the corrected systolic and diastolic blood pressure values are continuously generated and displayed or otherwise provided to the health care provider in real time, such as during surgery. Alternatively, such measurements may be collected over an extended period of time and analyzed for long term trends in the condition or response of the circulatory system of the subject. Pharmacological agents or other courses of treatment may be prescribed based on the resulting blood pressure measurements, as is well known in the medical arts. Similarly, in that the present invention provides for continuous blood pressure measurement, the effects of such pharmacological agents on the subject's physiology can be monitored in real time.

Occlusion Mitigation

Referring now to FIGS. 7a-14, yet other aspects of the invention are described. Specifically, the present invention provides apparatus and techniques for detecting and mitigating the effects resulting from the use of an occlusive cuff or similar device in conjunction with the hemodynamic sensing apparatus previously described herein.

It will be recognized that while the following exemplary embodiments are described in the context of a tonometric pressure sensor apparatus of the type previously described and referenced herein, the following invention may be adapted for use with other types of apparatus and processes, and accordingly should in no way be considered to be limited to the aforementioned exemplary tonometric apparatus.

Several types of "events" can cause the cessation of a detectable pulse pressure when using the tonometric apparatus described above. These include:

1) Over-compression: Over-compression can be caused by either motion of the subject being monitored, or by servo control operation during the so-called "patient monitoring mode" (second process 200). Under this condition, tonometrically measured pressure will increase, generally above systolic pressure, and remain high until the sensor is retracted to an appropriate level. Hence, the system should respond quickly, taking the appropriate corrective action through the triggering of rapid shift detector motion recovery.

2) Severe under-compression: If the applanation pressure is insufficient (e.g., less than 20 mmHg in the exemplary embodiment), the pulses generated by the subject's heart may not sufficiently coupled through the blood vessel wall to the overlying tonometric pressure sensor. Severe under-compression can be caused by, inter alia, patient motion. It is highly unlikely; however, that servo control operation during patient monitoring mode can cause this problem. To virtually eliminate pulse pressure coupling to the pressure sensor, applanation pressure must be significantly below the patient's diastolic pressure, and will often require appropriate corrective action through the triggering of rapid shift detector motion recovery as previously described herein. Note that moderate under-compression of the blood vessel will not eliminate the transfer of pulse pressure to tonometric pressure sensor.

3) Patient "Crash"—With the heart stopped, the patient's arterial pressure will exponentially decay toward central venous pressure (on the order of 10-20 mmHg in the typical human). Tonometrically measured pressure should follow a similar profile.

4) Lateral Repositioning—If the transducer is moved a sufficient distance laterally from the blood vessel, the pulse pressure signal will not be transferred properly through the skin. The existing tonometric pressure may initially change, but not likely in an exponentially decaying manner. Secondly, such movement would likely be accompanied by a trigger of the first process 100. Under this condition, a lateral repositioning of the sensor over the artery would occur as previously described herein.

5) Cuff Inflation—As previously discussed, the volume of the upper limb increases during cuff occlusion, as arterial blood flows into the region while venous return is prohibited. As cuff pressure increases flow (and thereby pulse pressure) ceases and the arterial blood transfers from the arterial tree to the venous system in the limb. The resultant pressure curve should approximate an exponentially decaying function wherein the resultant pressure is below diastolic pressure but significantly above central venous pressure. Variations in the performance of the cuff and its associated inflation/deflation systems (as well as the patient's anatomy) can influence this decay. The tonometric measurement system should accurately reflect this exponentially decaying pressure signal.

If a beat is not detected for a predetermined period of time (e.g., 5 seconds) under the second process 200 described above (also known as patient monitoring mode), the system will enter a rapid shift detection motion recovery, which starts as one or more mini-applanation sweeps. Since the lower limb is typically occluded 10-20 seconds during cuff inflation, the system routinely enters rapid shift motion recovery. In addition, the mini-sweeps during motion recovery can occur, at least partially, while the cuff is still inflated, leading to possibly unpredictable events including, e.g., lateral searches and errors in determination of optimal applanation level.

Figure 7A:
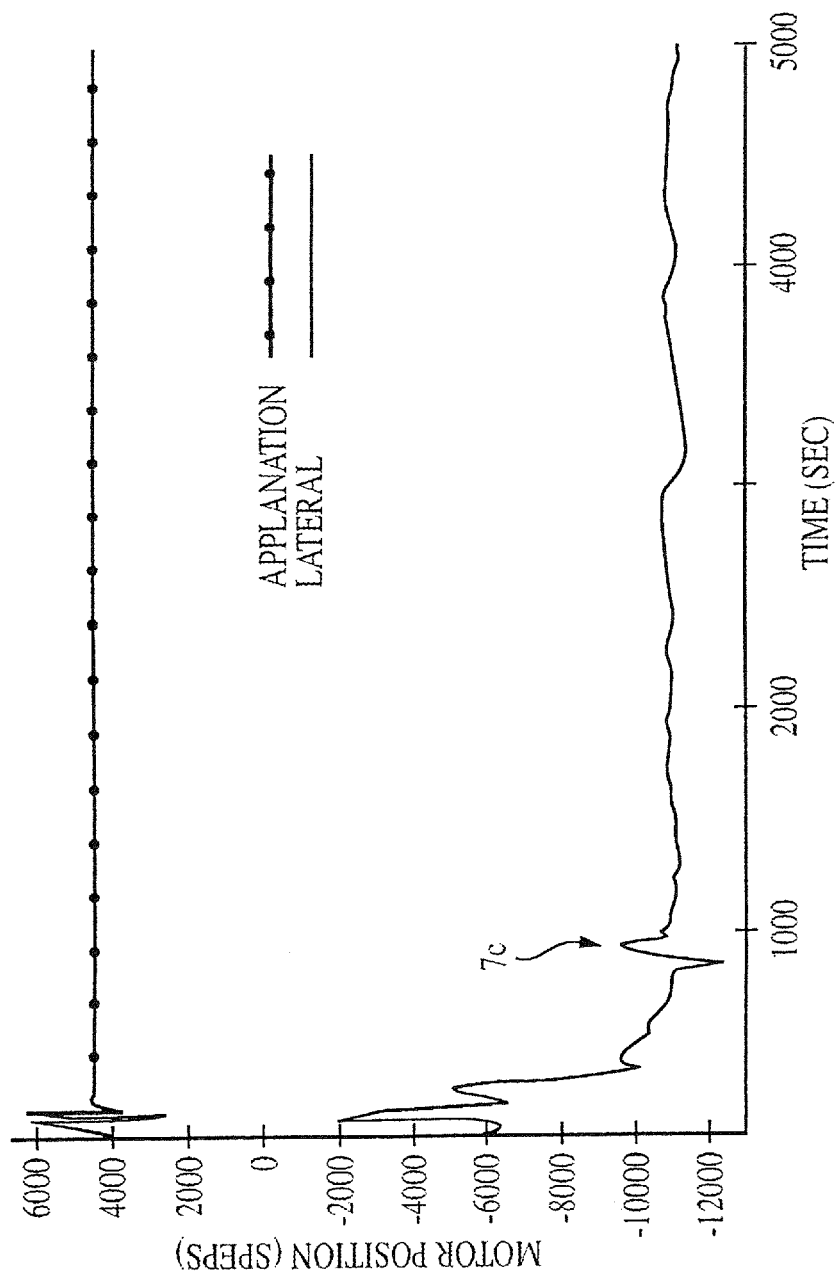
FIG. 7a-7c graphically illustrate the operation, including the effect on various parameters created by a loss-of-signal event, of an exemplary system without the "event compensation" capability of the present invention.
Figure 7B:
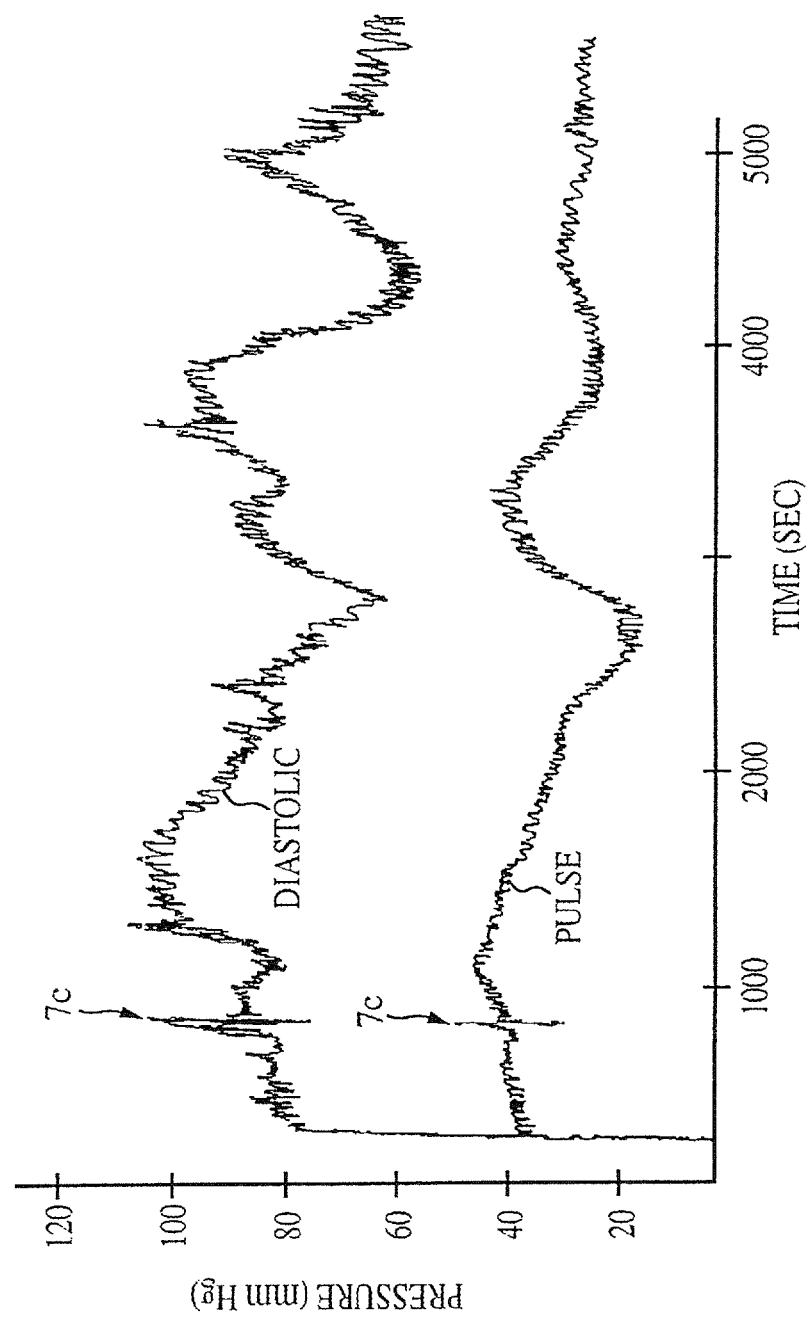
Figure 7C:
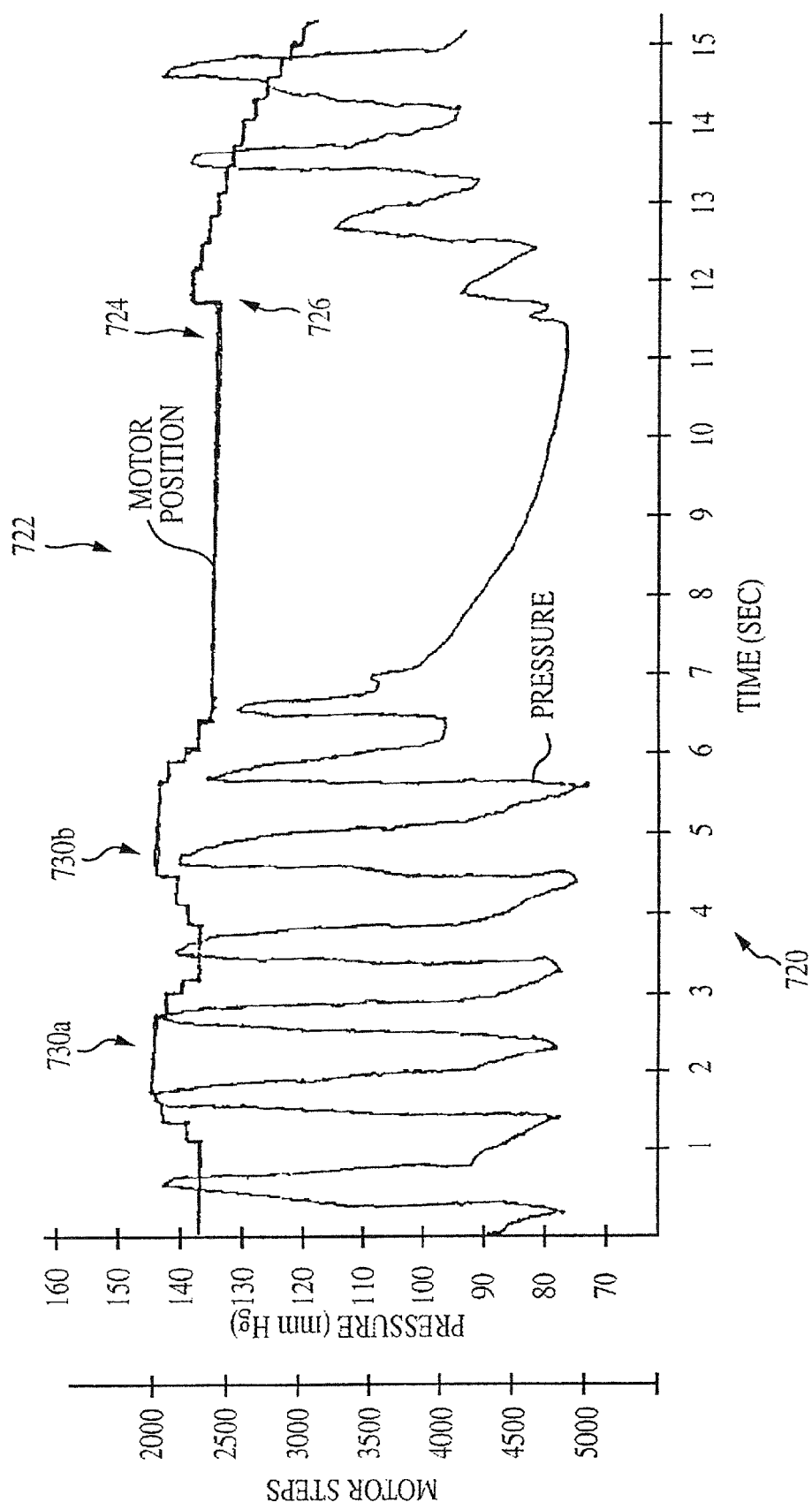

FIGS. 7a-7c graphically demonstrate the impact of cuff inflation on the tonometrically measured pressure signal. The exemplary data of FIGS. 7a-7c is extracted from a clinical study case performed by Assignee. FIG. 7a depicts the lateral and applanation motor position for the entire case. FIG. 7b depicts the diastolic and pulse pressures for the entire case. FIG. 7c illustrates (i) an extract or zoom view of a portion of the tonometric pressure data in FIG. 7a lasting 15 seconds; and (ii) applanation motor position as a function of time during the aforementioned 15-second period. Referring to FIG. 7c, it can be seen that at approximately the 4-second mark 720 a cuff was inflated on the arm ipsilateral to the tonometric sensor. During the next few beats, the diastolic pressure increased and the diastolic waveshape changed. After about 7 seconds the artery fully occluded, such occlusion lasting beyond the 11-second mark 724. During this period 722 the tonometric pressure decayed exponentially to a value slightly below diastolic pressure, and well above central venous pressure. Since the beat detector had not identified a "good" beat in the previous 5 second interval, the rapid shift detection process triggered a motion recovery mini-sweep to be performed beginning at the 12-second mark. 726. Note that applanation motor dither 730a, 730b occurs during the first five seconds. Without a new beat after the second dither event 730b, the dither process is suspended. After the 12-second mark 726, the mini-sweep ramping of the applanation motor begins.

Note that delaying the triggering of rapid shift detector-initiated motion recovery for even a few seconds would have changed the course of events significantly. The extra time afforded by the delay would have enabled the return of flow to the limb (with its associated subsequent measurable pressure pulses) to prevent the system from initiating the mini-applanation sweep. Thus, the operation of the system could be appreciably improved by selectively extending the duration of the "no-beat" trigger of the motion recovery process. By delaying the onset of triggering of the rapid shift detector motion recovery process, when a cuff is suspected, one or more mini-sweeps can be omitted, and the probability of initiating lateral sweeps for motion recovery virtually eliminated. Hence, in one aspect, the present invention is meant to utilize the foregoing delay period to obviate the aforementioned applanation mini-sweeps and lateral position sweeps.

Two fundamental approaches may be utilized by the system in dealing with the foregoing pressure/beat loss events. First, all such events can be treated similarly (irrespective of origin) with a more global or uniform response. Second, the system may attempt to discriminate between or classify two or more different types of events, the response to each different type of event which also may vary. These two approaches form the basis of the two exemplary embodiments of the invention described subsequently herein. It will be recognized, however, that while described effectively as discrete or separate approaches, the following techniques (and associated apparatus) may be used in conjunction with one another if desired. For example, in one aspect, one technique may be used with respect to a portion of the total population of "events", while the other approach used for the remainder. As yet another alternative, the outcomes of the two approaches may be evaluated in parallel, with that providing the most rapid and/or accurate system response and recovery being selected. Numerous other possibilities for combining the two approaches exist, such other combinations being readily identified and implemented by those of ordinary skill provided the present disclosure.

In a first exemplary embodiment of the invention, an improved method (and apparatus) for handling loss-of-pressure events such as those described above. As previously indicated, this first method makes no distinction between the different types or origins of the event.

Figure 8A:
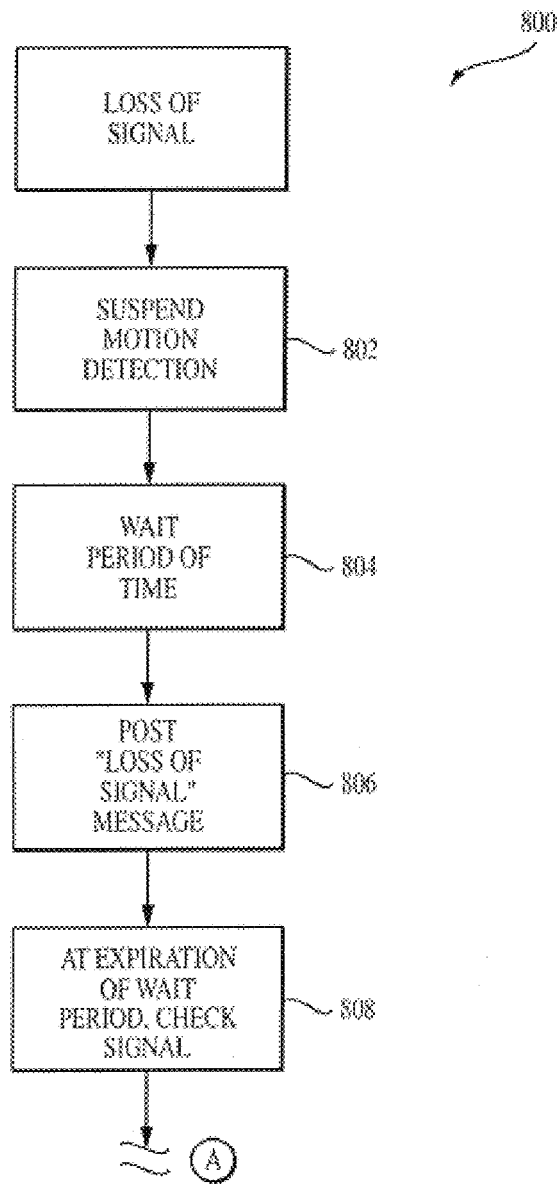
FIG. 8a is a logical flow diagram illustrating one exemplary embodiment of the method (algorithm) for compensating for loss of signal events according to the present invention.
Figure 8B:
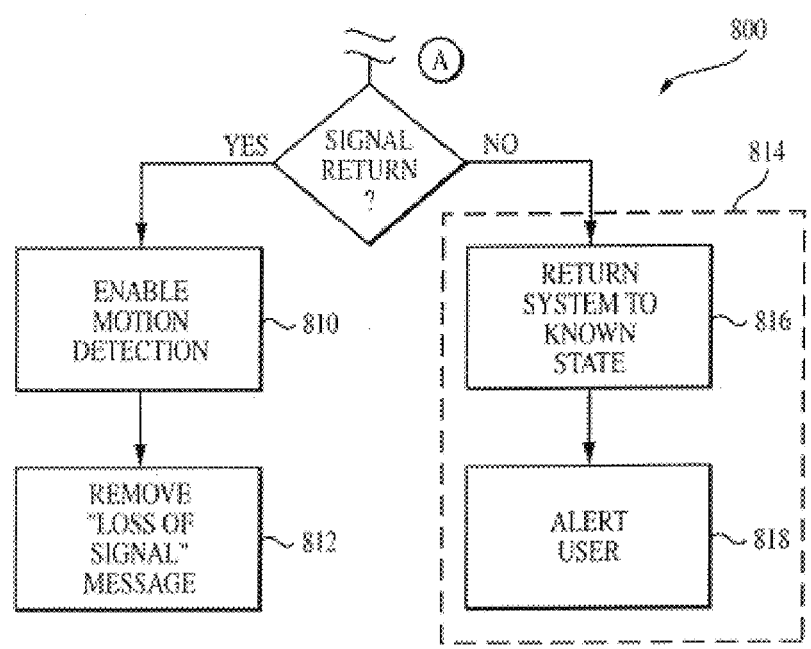
FIG. 8b is a logical flow diagram illustrating one exemplary embodiment of the method (algorithm) for compensating for loss of signal events according to the present invention.

Specifically, no attempt at discriminating ipsilateral cuff inflations from other events is used. Rather, as shown in FIGS. 8a-8b, if a loss of signal is detected for any reason, the system: suspends the motion detection of the first process 100 from triggering a motion recovery (step 802), waits an amount of time that is sufficiently longer than a cuff inflation cycle (e.g., worst case) (step 804), and optionally posts an "abrupt loss of signal" alert message to the user alerting him to the same (step 806). At the end of the wait period, the system checks to see if signal has returned on its own accord (step 808), indicating that a cuff had possibly inflated/deflated. If it has, then the aforementioned motion detectors are re-enabled (step 810) and the "abrupt loss of signal" alert message is removed from the display if used (step 812). If signal has not returned on its own accord, then the system goes into a halt state (step 814). The halt state in the illustrated embodiment comprises safely returning the system to a known initial state (step 816), as well as alerting the user as to same via an alert message posted on the internal display and/or other means such as audible alarm, etc. (step 818).

The exemplary algorithm represented by FIG. 7 has been tested by the Assignee hereof on a number of patients and found to work well. By nature of its non-discrimination of different types of events, a delay is imposed on both types of events (i.e., cuff-related and non-cuff related). However, the delay, which is set on the order of 30 sec. in the illustrated embodiment, is minimal and considered fully acceptable and clinically practicable.

Figure 8C:
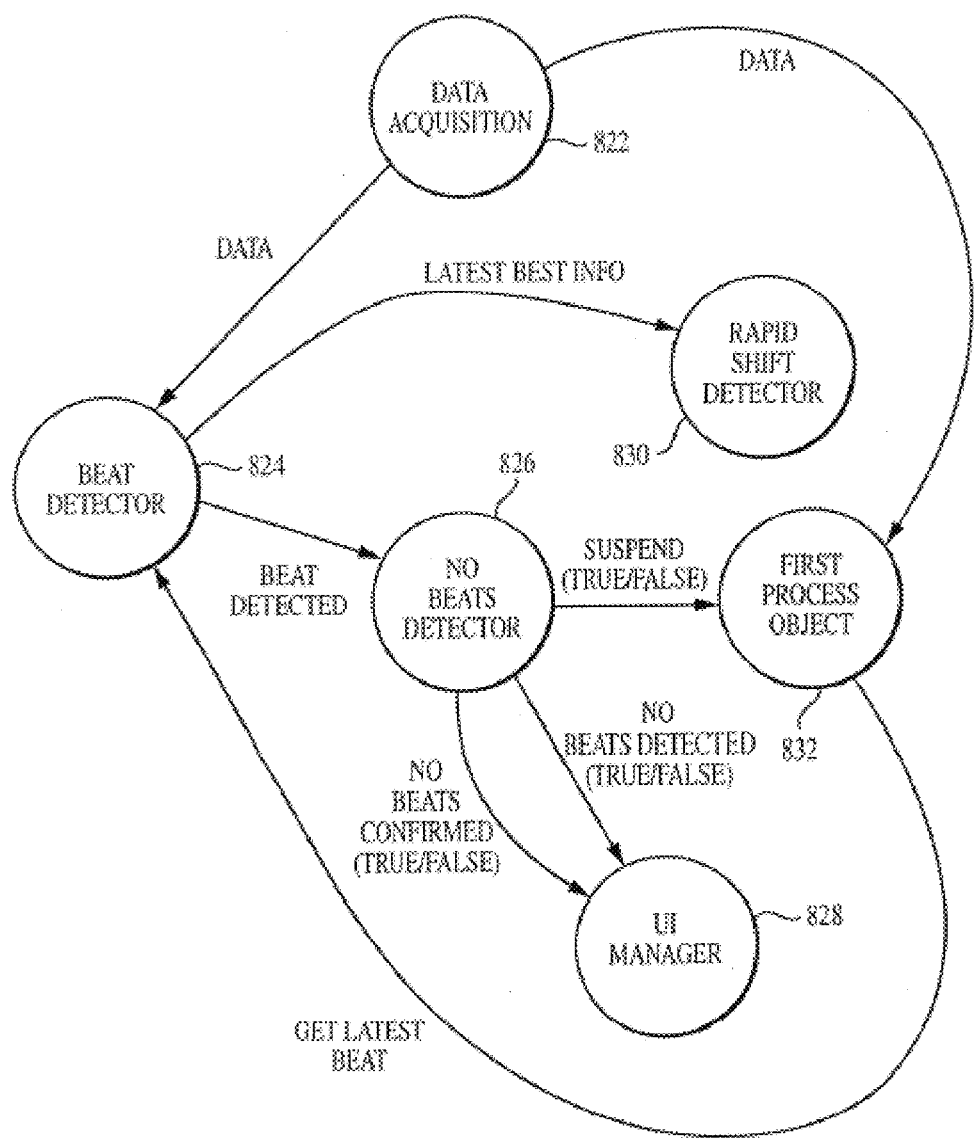
FIG. 8c is a graphical representation of first exemplary software architecture embodying the algorithm of FIGS. 8a and 8b, including a plurality of functional "objects."
Figure 9:
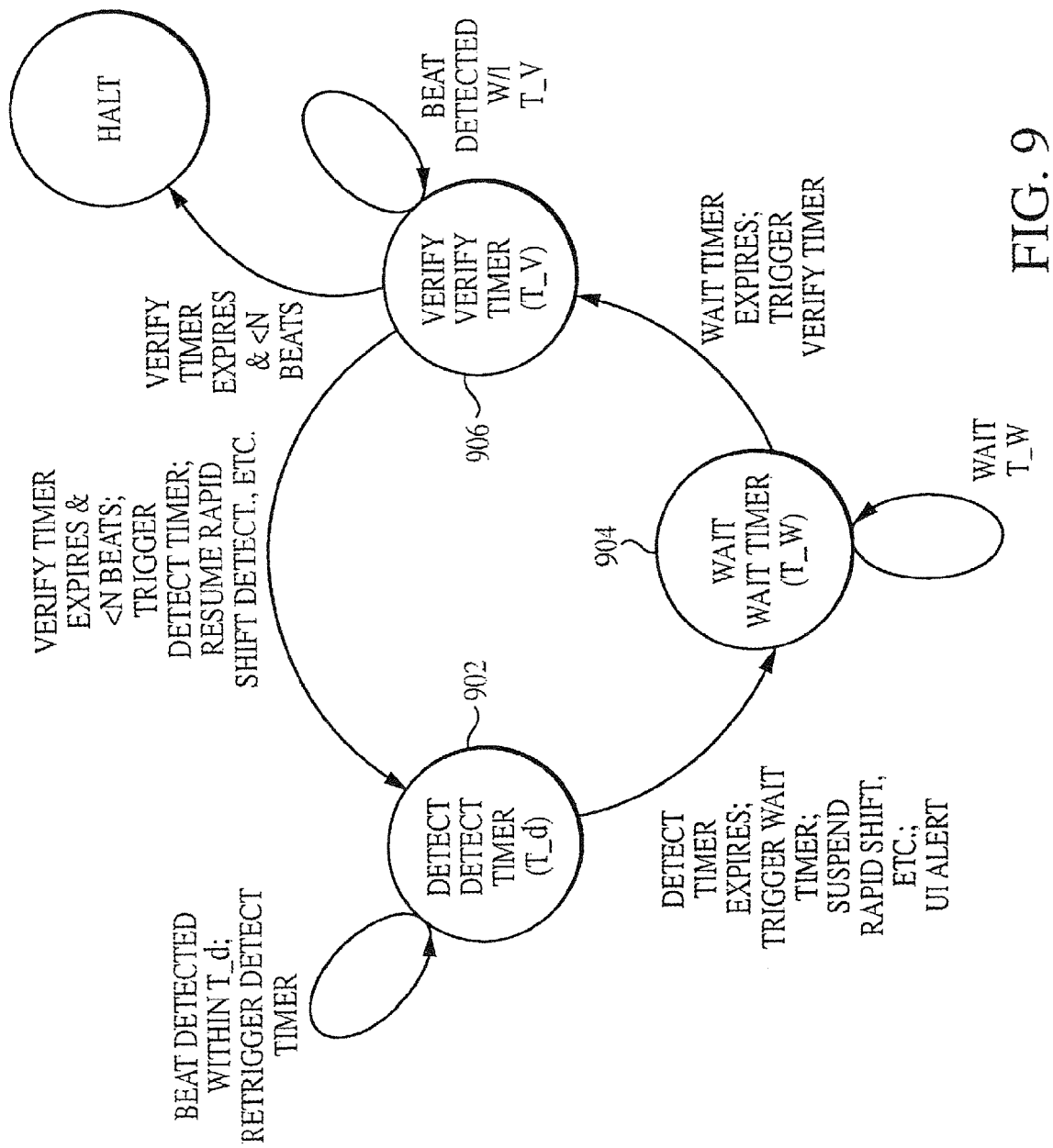
FIG. 9 is a state diagram illustrating the various states of operation associated with the algorithm and architecture of FIG. 8a-8c.

In the exemplary embodiment, several (software) objects collaborate in implementing the algorithm 800 of FIGS. 8a and 8b. The objects and their collaborations of this exemplary embodiment are shown in FIG. 8c. As seen in FIG. 8c, there are six (6) "objects" that collaborate: (i) data acquisition object 822; (ii) beat detector object 824; (iii) no beats detector object 826; (iv) rapid shift detector object 830; (v) first process object 832, and; (vi) user interface (UI) manager object 828. As will be readily understood by those of ordinary skill in the programming arts, these objects may be rendered in any form or language suitable to provide the functionality disclosed herein, including without limitation using conventional programming languages such as C, C++, Fortran, Basic, etc., which are all well known and accordingly not described further herein. Furthermore, so-called "object oriented" approaches such as for example the common object request brokered architecture (CORBA) May be used. Furthermore, the objects described herein may be purely "virtual" in nature; i.e., any architecture or configuration which provides the desired functionality may be utilized consistent with the invention. The description of the present invention in the context of software objects is merely used to clarify the principles of operation and functionality of the invention, and is therefore in no way limiting.

The data acquisition object 822 continuously acquires the digitized pressure waveform and makes it available for the other software modules in the system.

The beat detector object 824 continuously detects beats in the tonometric pressure waveform. It determines the systolic, diastolic, pulse and mean pressure of each beat, as well as its period. It also determines heart rate and notifies other (predetermined) software modules when a beat has been detected.

The no beats detector object 826 detects the absence of a beat (i.e. loss of signal) within a certain period of time ($T_{detect}$). Upon detection of a loss of signal, it suspends detectors of the first processes 100, notifies the UI manager object 828 as to the signal loss, and goes into a wait state for a period of $T_{wait}$ seconds. After $T_{wait}$ seconds, the object checks for the occurrence of N beats in a period of $T_{verify}$ seconds. If N or more beats are observed, the object 826 resumes the first process 100, notifies the UI manager object 828 as to signal restoration and; returns to a state of detecting at least one beat in a period of $T_{detect}$ seconds. If N or more beats are not observed, the object 826 puts the system into the halt state previously described.

The rapid shift detector object 830 is designed to detect slowly varying changes in mechanical coupling of the systems pressure sensor to the patients forearm. In the exemplary embodiment, the object 830 detects relatively slow changes in pulse pressure as mean pressure increases or decreases. It also attempts to discriminate changes that occur at rates more rapid than normal physiologic changes in the patient. If a significant change is pulse pressure is detected, then a motion recovery (i.e. applanation sweep optionally followed by lateral search) is performed in an attempt to recover the measurement of mean arterial pressure.

The first process object 832 is designed to detect rapid changes in mechanical coupling of the pressure sensor to the patient due to transient events. Typical transient events include "thumbs" or "bumps" upon the actuator that may happen in the course of a normal operating room, clinical, or other environment. The object 832 operates upon the tonometrically sensed waveform as well as the latest beat information provided by the beat detector object 834. If a significant change in operating level is detected, due to a transient event, then a motion recovery (i.e. applanation sweep optionally followed by lateral search) is performed in an attempt to recover the measurement of mean arterial pressure.

The UI manager object 828 displays the tonometrically obtained pressure waveform as well as posting all significant status and alert messages to the user.

An exemplary state diagram for the no beats detector object 826 described above is presented in FIG. 9. In this diagram, there are essentially three states: (i) detect 902, (ii) wait 904, (iii) and verify 906, now each described in greater detail.

(i) Detect State—The detect state is the normally operating state. In this state, the no beats detector object 826 is looking for the presence of at least one beat within a period of $T_{detect}$ seconds. The beat detector object 824 notifies the no-beats detector 826 when a new beat is detected. This event causes the retriggering of the "one-shot" timer of the detect state 902, thus preventing a timer expiration event. As long as new beats are detected within $T_{detect}$ seconds, the no-beats detector 826 remains in this state. However, if no beats are detected within $T_{detect}$ seconds, then the no-beats detector 826 transitions to the wait state 904. During the transition, the wait state timer is initiated, the rapid shift detector object 830 and first process object 832 are suspended, and the UI manager object 828 is notified as to the abrupt loss of signal.

(ii) Wait State—While in the wait state 904, the no-beats detector object 826 waits for the one-shot wait state timer to expire (in $T_{wait}$ seconds). No other activity is in progress. Upon expiration of the wait state timer, the no-beats detector transitions to the verify state and triggers a "one-shot" timer associated with the verify state 906.

(iii) Verify State—In this state 906, the no-beats detector object 826 looks for the presence of at least N beats within $T_{verify}$ seconds. If ≥N beats are detected upon expiration of the verify state timer, then the no-beats detector 826 reverts back to the detect state. During the transition, the detect state one-shot timer is triggered, the rapid shift process 830 and the first process 832 are enabled, and the UT manager 828 is notified. However, if <N beats are detected, then the system safely transitions to the "halt" state, and the user optionally alerted as to the state change.

Figure 10:
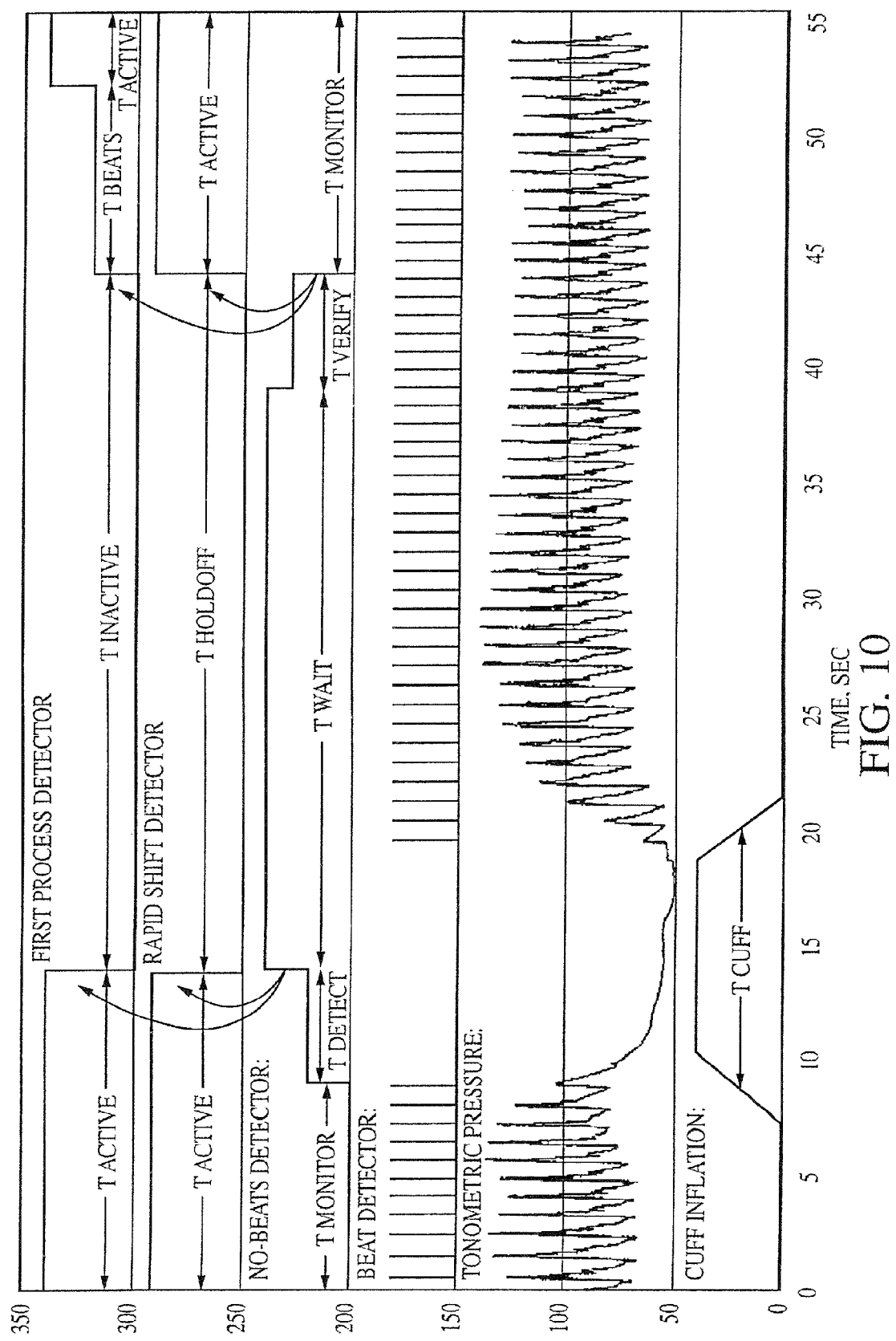
FIG. 10 is a timing diagram reflecting the variation in various parameters associated with the system when operating according to the algorithm of FIG. 8a-8c.

A timing diagram for the exemplary embodiment of the algorithm of the present invention is shown in FIG. 10. This Figure illustrates a typical cuff inflation/deflation cycle, and the detection of same by the aforementioned algorithm. As seen in FIG. 10, the cuff inflation event 1002 results in occlusion of the artery, which results in an abrupt loss of signal in the tonometrically obtained pressure waveform 1004. The beat detector object 824 detects this loss of signal. The loss of beats for a period of time greater than $T_{detect}$ results in the no-beats detector 826 transitioning from the detect state 902 to the wait state 904. Also shown in FIG. 10 is the suspension of the rapid shift detector 830 and first process objects 832. After a period of $T_{wait}$ seconds, the no-beats detector 826 is shown entering the verify state 906 whereupon a given number (here, seven (7)) of beats are detected. This results in a transition back to the detect state 902 with consequent notifications of rapid shift detector object 830, first process object 832, and the UI manager object 828. Note that, after sending the first process object 832 a resume message, an additional hold-off period of $T_{beats}$ seconds is applied to ensure that valid beats are present before re-activation of the algorithm, although other schemes for accomplishing this result may be used.

Cuff inflation/deflation cycle times can vary considerably. The variability is associated, in part, with the instrument having a "memory" as to what the previous cycles' arterial pressure values were, and hence an estimate as to how much inflation is required to occlude the artery on the next cycle. Unfortunately, the assumption that the parameters associated with one cycle are valid for the next cycle is sometimes not valid due to, inter alia, changes in patients' physiology and/or placing the cuff on another patient. As a result of this variability in cycle times, it was found by the Assignee hereof that the no-beat detector object's wait state time was best increased from a typical cuff inflation/deflation cycle time of 15 seconds to about 30 seconds. It will be recognized, however, that if the invention is used with cuff apparatus having smaller or larger variability in cycle time, then the wait state time associated with the no-beat detector object 806 may be adjusted accordingly if desired.

Typical parameters for the exemplary embodiment of the present algorithm are shown in Table 3.

TABLE 3

| T detect (sec) | T wait (sec) | T verify (sec) | T beats (sec) | N beats (counts) |
|---|---|---|---|---|
| 5 | 30 | 5 | 8 | 2 |

It is noted that as long as the cuff inflation frequency is reasonable (i.e. the period of inflation is greater than the aforementioned wait period) on the limb ipsilateral to the tonometric pressure sensor, then the operation of the algorithm described herein is optimized. Otherwise, multiple cuff inflations occurring within in a period less than the wait period may produce undesired results, and require adaptation of the algorithm to account for the increased frequency of cuff cycling. Such adaptations are readily accomplished by those of ordinary skill given the present disclosure, and accordingly not described further herein.

In another embodiment of the invention, the algorithm is adapted to check for the return of beats, while in the fixed time $T_{wait}$ state. When a sufficient number of beats have returned (e.g., ≥3 in the current implementation), then the no-beats detector notifies the UI manager 828 that beats have returned. Subsequently, the UI manager 828 removes the flashing "abrupt loss of signal" message from the display. Thus, as far as the user is concerned, the system has exited from the wait state and processing has returned back to normal. This provides added assurance to the operator that the system is operating properly, since it detected the return of beats. However, as mentioned previously, the algorithm waits a fixed amount of time until the wait timer expires (e.g., 30 see). Hence, during this remaining time, the system will not react to motion events.

It is significant to note that the foregoing embodiments advantageously provide for occlusive device (e.g., cuff) "tolerance" as opposed to detection. In this regard, the approach is largely passive in nature, and requires no electrical or mechanical connections of any kind to the occlusive device. Rather, it accommodates the effects of the occlusion by such device, thereby preventing any deleterious effects on the accuracy or robustness of the tonometric measurement. This accommodation is accomplished primarily through detection of an abrupt loss of signal; when such abrupt loss of signal occurs, the algorithm of the illustrated embodiment merely suspends the action of the motion detectors that would normally attempt to recover the lost signal, in the assumption that an ipsilateral cuff inflation might have occurred.

Herein lies a significant advantage of the present embodiment, specifically that the apparatus and algorithm can accommodate occlusive or similar events without any prior knowledge or active detection of the occlusion, and without deleterious effect on the accuracy of the resulting blood pressure value generated by the system.

However, it will be recognized that the present invention may be readily adapted for active detection of concurrent occlusive device use as well if desired. As a simple example of the foregoing, a signal generated by the occlusive device during inflation/deflation cycling (such as, for instance, the signal generated by the controller of the occlusive device initiating an inflation event) may be transmitted to the apparatus/algorithm of the present invention thereby initiating the suspension or "hold-off" described above. Such active approach, while requiring a signal or comparable interface between the two devices, has the benefit of obviating significant portions of the algorithm described above. Specifically, at least portions of the no-beats detector object 826 are not utilized since the aforementioned control signal from the occlusive device unambiguously informs the object 826 that an occlusive event has been initiated.

Transmission of the foregoing occlusive device signal between the two devices may be conducted using any number of well known interface techniques including, without limitation, direct signal transmission via an electrically or optically conductive conduit (e.g., wire, optical fiber, etc.)

according to any of the well known data interchange protocols such as USB, RS-232, IEEE 1394 ("Firewire"), RF transmission such as via IEEE 802.11, Bluetooth 2.4 GHz, or time-modulated UWB interface, IrdA infrared interface, etc. Such interface mechanisms and protocols are well known, and accordingly not described further herein.

So as to provide for universal compatibility of such "active" tonometric apparatus with the ipsilateral occlusive device, such apparatus may also be provided with the ability to detect the initiation of an inflation/deflation cycle without direct interface with the occlusive device.

For example, means adapted to detect cuff inflation or other physical events associated with the inflation/deflation cycle may be used, such as a sensor (lead) which can be clamped onto a signal cable or inflation tube of the occlusive device to detect electrical/inductive or pneumatic changes in the cable or tube, respectively, consistent with cuff inflation. Myriad different schemes for "pseudo-passively" detecting cuff inflation/deflation can be employed, the foregoing being merely illustrative of the broader principle. This pseudo-passive "universal" detection scheme allows the present apparatus to simply be connected onto any indigenous occlusive device, such as in a hospital operating room, irrespective of the configuration of the occlusive device. Much as an inductive timing gun is clamped onto the spark plug leads of an operating automobile engine, the pseudo-passive detector of this alternate configuration can be attached to any occlusive device whether it has a dedicated signal interface or not.

The pseudo-passive detection of cuff inflation is to be contrasted with the aforementioned fully passive detection of cuff inflation by the algorithm, the latter being performed entirely via hemodynamic means. While necessitating additional hardware and cost, the active or pseudo-passive approaches may have utility, for example, as a confirmatory check of the fully passive approach, during system maintenance/calibration (i.e., to see how well the cuff mitigation algorithm of the fully passive approach accommodates "known" occlusion events as identified by the pseudo-passive/active detector), or in cases where for whatever reason the fully passive approach anecdotally yields less than optimal results. Consider, for example, the case where a high frequency of events attributable to causes other than occlusive device inflation are occurring (i.e., items 1)-4) described above), such as very frequent jostling or movement of the patient. Since the present embodiment of the algorithm purposely does not attempt to differentiate between or categorize the two types of events (occlusive-related and non-occlusive related), it would in effect assume that each event might have been a cuff inflation, thereby invoking the foregoing cuff mitigation functionality for each event. However, if the algorithm is unequivocally told that an inflation event is occurring (via either active or pseudo-passive means), then it knows at least which loss-of-pressure signal events are cuff-induced and which are not. This knowledge can be used as the basis for entering different variants or subroutines in the algorithm. For example, where a known occlusive event has occurred, the foregoing cuff mitigation algorithm may be used. Where the event cannot be correlated to an occlusive event, a categorization algorithm may be used to determine the proper system response to the event, or the system may simply operate outside the cuff mitigation algorithm, such as within the first process 100 ("thump and bump") described above. It will be recognized that myriad other logical control schemes can be employed based on the foregoing information as well.

Figure 11:
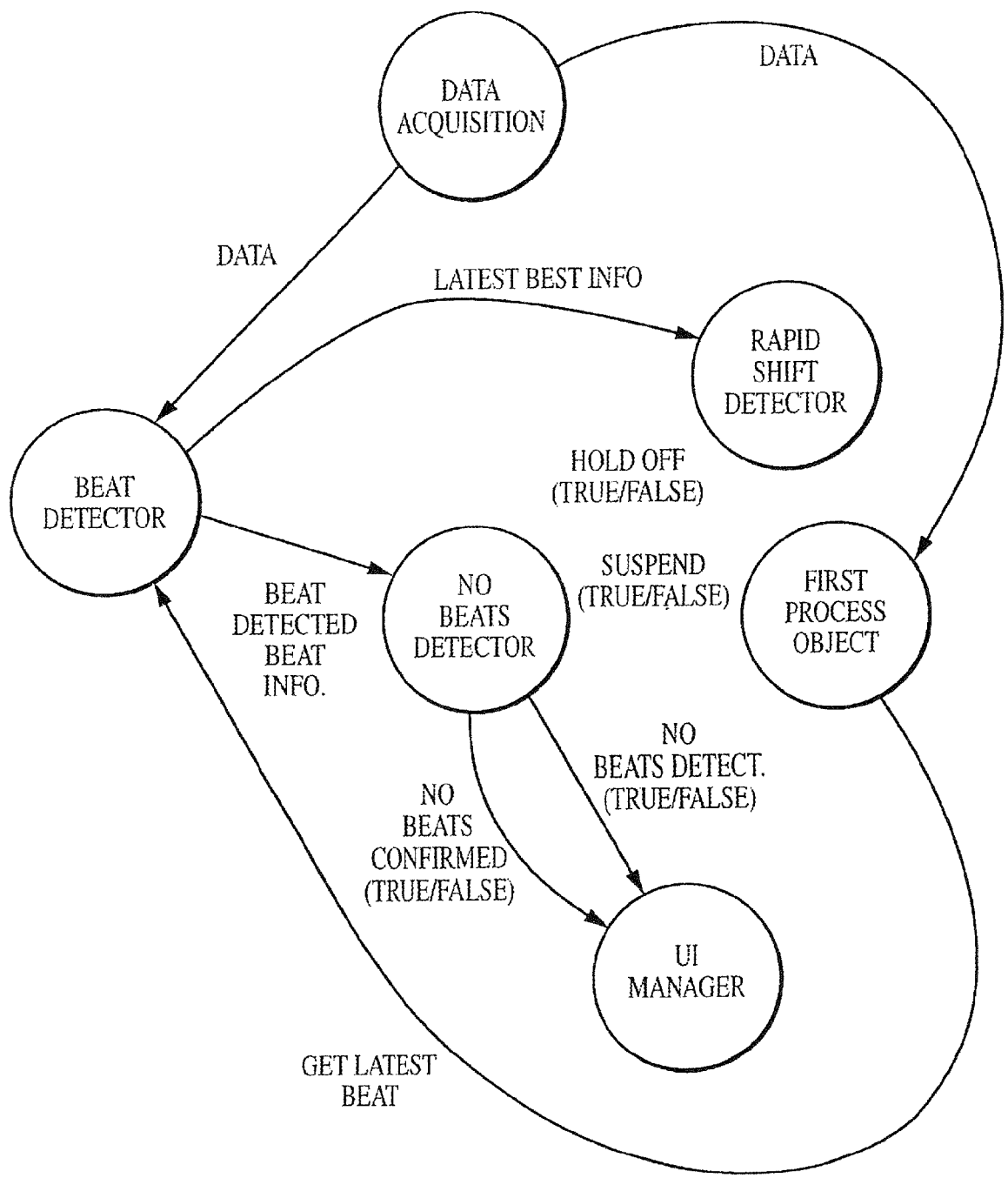
FIG. 11 is a graphical representation of second exemplary software architecture embodying an algorithm adapted for early termination of the wait state.

Referring now to FIG. 11, another exemplary embodiment of the invention is described in detail. In this embodiment, a means for early termination of the wait period is also provided. There are two primary benefits of an early termination of the wait period: 1) an increased tolerance to more frequent cuff inflation/deflation events; and 2) a decreased period wherein the motion detectors are not enabled. The early termination criteria of the present embodiment involves observing a sufficient number of "quality" beats in a time interval which is smaller than the overall wait period. One assumption supporting this approach is that these so-called quality beats are observed during the period of relaxation of the occlusive device (e.g., cuff deflation). The quality of these beats are determined by analysis and comparison with known good beats (KGBs) that were previously stored in a system (history) buffer prior to the inflation of the cuff. If the observed beats are comparable in quality to the KGBs, then the wait period can be terminated early. That is, more than likely, the cuff has fully deflated and the quality of the beats is comparable to the quality prior to the inflation of the cuff.

An exemplary variant of this second embodiment of the algorithm is now described in detail. The features of this variant can be best illustrated in comparison to the algorithm described previously herein with reference to FIGS. 7-10. Thus, FIG. 11 shows a modified object collaboration diagram. The primary point of difference relates to the beat detector object 1104. Specifically, in the present variant, the actual beat information (pulse pressure, mean pressure, etc.) is stored by the no-beat detector object 1106 and used in the above-referenced comparison of the quality of the beats.

Figure 12:
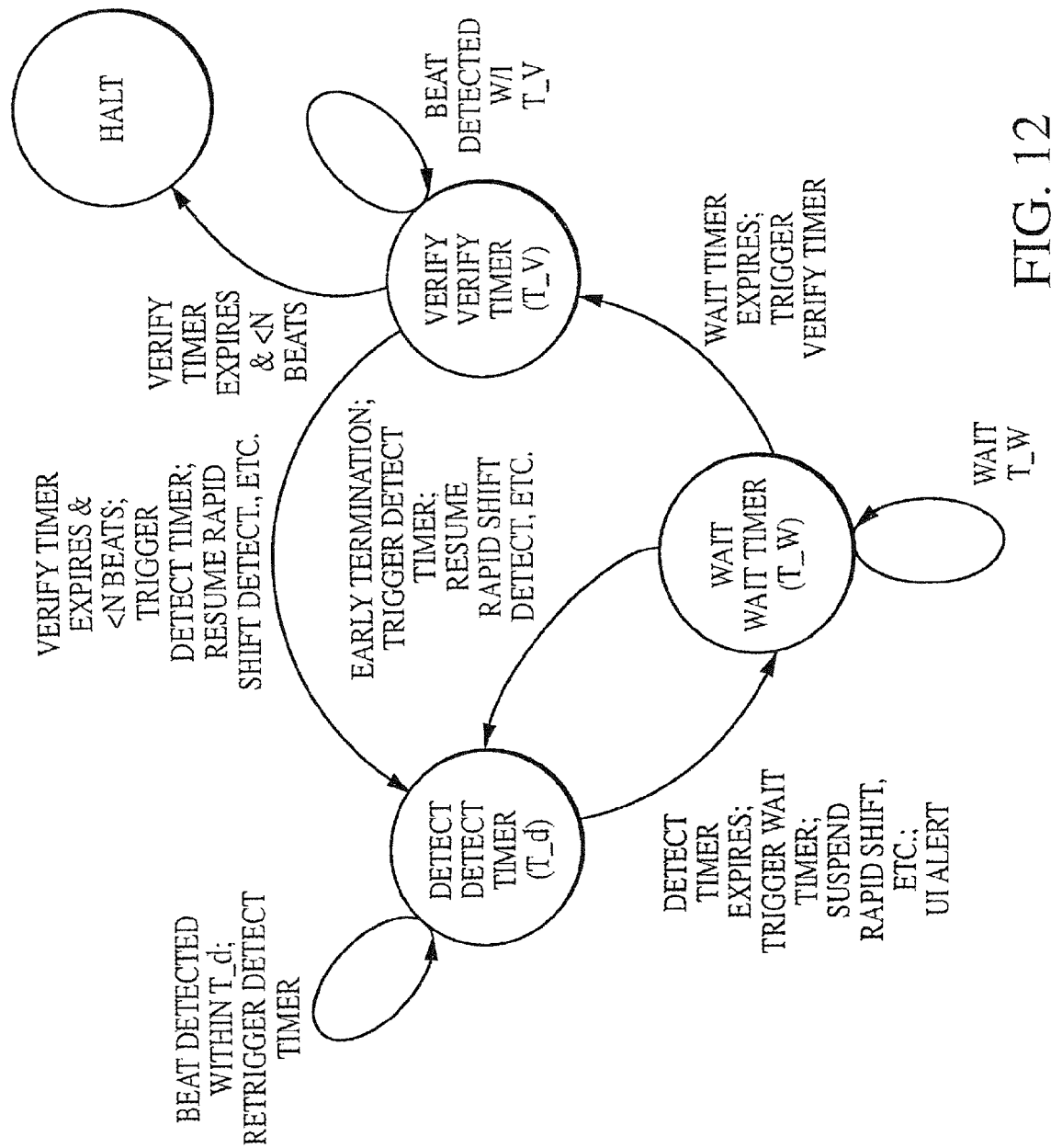
FIG. 12 is a state diagram illustrating the various states of operation associated with the architecture of FIG. 11.

A modified state diagram for the embodiment of FIG. 11 is shown in FIG. 12. Here, an early termination path is indicated. The early termination will return the no-beats detector object 1106 back to the detect state 902, with a consequent enabling of the rapid shift detector object 830 and first process object 832.

Figure 13:
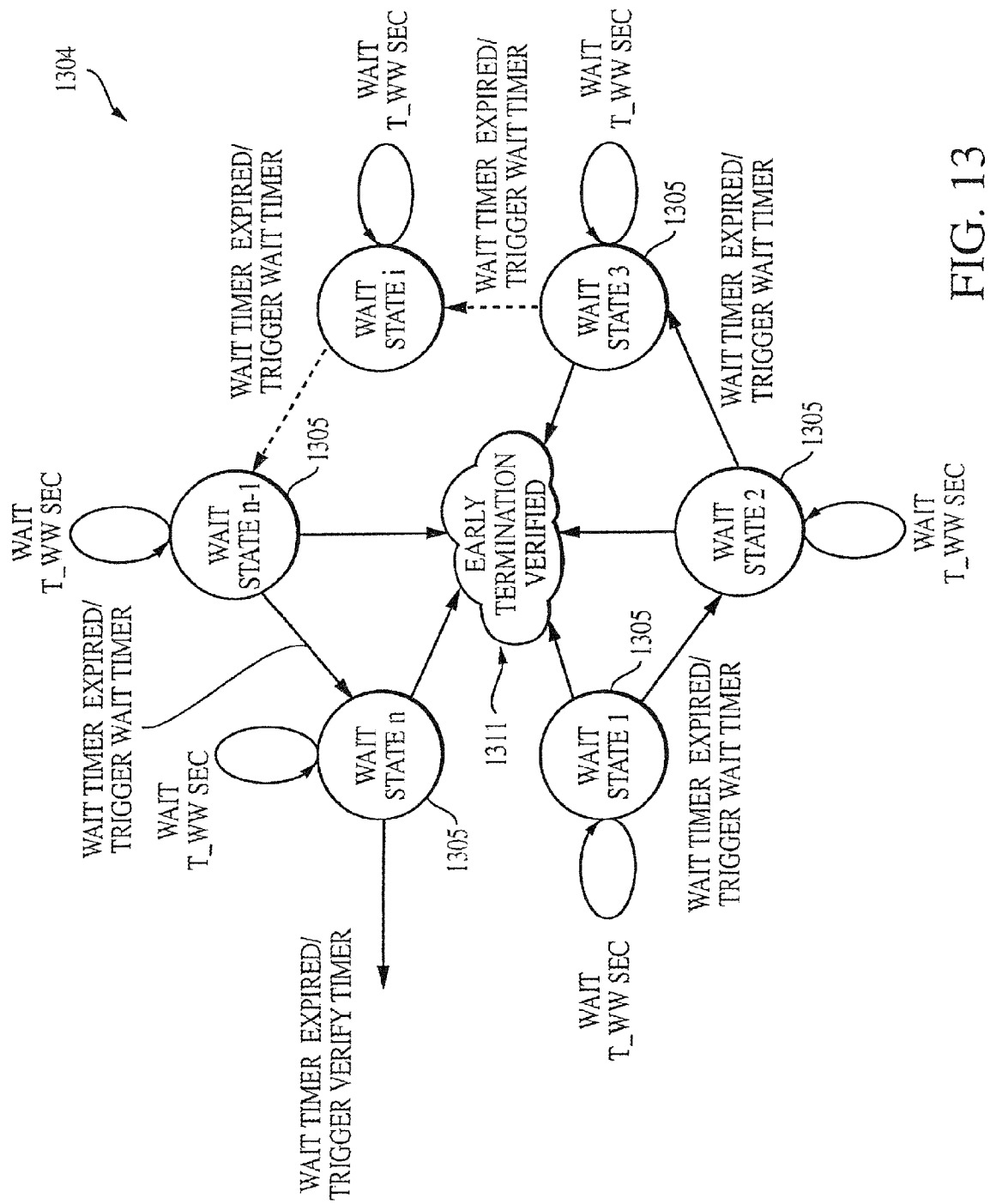
FIG. 13 is a graphical representation of wait state configuration used within the architecture of FIG. 12.

FIG. 13 presents the internal details of the exemplary wait state. That is, the wait state 1304 is shown composed of a series of smaller wait states 1305, typically each being on the order of about five (5) seconds although the number and duration of each state may be varied. In each wait state 1305, beat information is collected and stored. If a sufficient number, of beats are observed with quality comparable to the beats observed prior to cuff inflation, then an early termination state transition 1311 is allowed. Otherwise, each state 1305 transitions to the next state as its timer expires, and the process repeated for each additional state.

Figure 14:
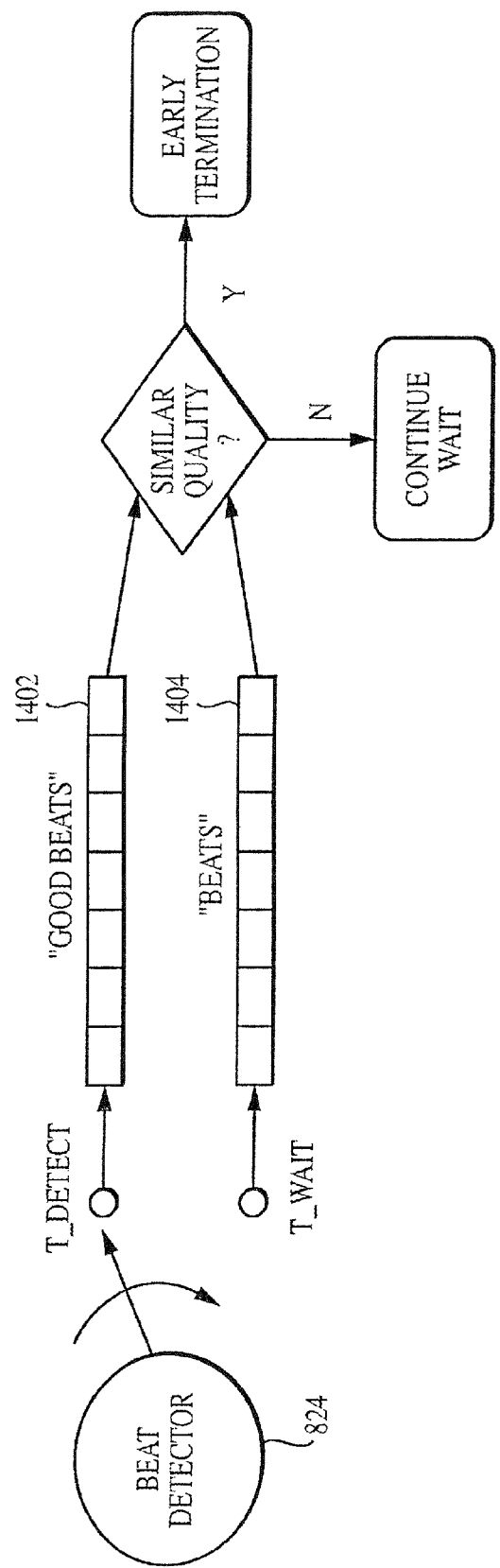
FIG. 14 is a logical block diagram illustrating an exemplary architecture for evaluating whether early termination of the wait state is appropriate.

FIG. 14 illustrates an exemplary architecture for the "quality" determination previously referenced. The beat information from the beat detector object 824 is stored in two different data buffers 1402, 1404 depending on whether the no-beat detector 826 is in the detect state 902 (good beats) or in the wait state 904 (beats). FIG. 13 shows that the stored beat information (e.g., pulse pressure and mean pressure) is used to determine and compare the quality of the beats during the previously discussed wait state transitions. If the quality of the central tendency of the data in the two buffers 1402, 1404 is comparable, then an early termination is warranted. Otherwise, the transition to the next wait state will occur.

As will be readily apparent, the metric for quality determination referenced above can have several different forms. That is, a measure of central tendency of the buffered beat data is desired. However, filtering of the data is also desirable to remove the influence of "outliers" or other artifacts attributable to the cuff inflation/deflation, noise, or other sources.

The use of quality in the aforementioned determination is illustrated by the following example. Specifically, prior to any cuff inflation, consider the system operating in the Patient Monitoring Mode (PMM) for sufficient duration such that the "good beats" (circular) buffer 1402 is filled with valid beat information consisting of pulse pressure, mean pressure, and timestamp data for each beat. When an ipsilateral cuff inflates sufficiently to cause the cessation of the detection of beats by the beat detector 824, the no-beats detect timer will trigger after a predetermined period (e.g., 5 seconds). When this happens, an "abrupt loss of signal" sequence occurs wherein the no-beats detector 826 begins to transition through its wait states as previously described. At this time, estimates of central tendency of pulse and mean pressure in the "good beats" buffer is accomplished by: 1) recording the time when the no-beats detect timer triggered; 2) parsing through the "good beats" buffer and marking all beats from the time of trigger of the no-beats detect timer back in time for the predetermined period (5 sec) plus an additional period; i.e., an estimate as to how long it took the cuff to inflate (typically on the order of 10 to 15 seconds). For all remaining beats in the "good beats" buffer, an average pulse pressure and average mean pressure are estimated. The "beats buffer"1404 is then flushed, and beats are no longer stored in the "good beats" buffer 1402 until the no-beats detector 826 returns back to the "detect" state. Rather, any new beats observed from the beat detector 824 during this period are stored in the "beats" buffer 1404.

In one exemplary variant of the invention, the quality of the beats stored in the beats buffer 1404 is compared with the previously determined "good beats" central tendency (i.e. the averages of the pulse and mean pressures are compared). To accomplish this comparison, the average mean and pulse pressure are calculated for the data stored in the beats buffer 1404. An exemplary measure of quality comprises the following: if the average pulse and average mean pressure of the beats buffer 1404 data is within a given percentage (e.g., 80%) of the previously determined average pulse and mean pressures (both high and low) associated with the "good beats" buffer 1402 data, then the beats in the "beats buffer" 1404 are considered to be of comparable quality to the beats stored in the "good beats" buffer 1402. Hence, there is sufficient evidence for an early termination of the algorithm.

If early termination is warranted, then new beat data from the beat detector object 824 is subsequently stored in the "good beats" buffer 1402 (after having flushed all previous data from the "good beats" buffer). If early termination is not warranted, then the "beats buffer" 1404 is flushed in preparation for the next mini-state beat collection and test.

In yet another alternate embodiment of the invention, the algorithm is configured so as to distinguish between at least two types of events; i.e., occlusive events and non-occlusive events. As with the first embodiment of the algorithm described above, the present embodiment is not intended to unerringly detect and discriminate occlusive events from other events. However, it does attempt to distinguish occlusive events from other types of events through passive analysis of the hemodynamic data to at least some level of accuracy, thereby obviating at least some "unnecessary" algorithm-induced sweeps and processing, and making the device track better (and more clinically robust).

The exemplary algorithm of the current embodiment operates as part of the no-beats detector process 826 previously described. Note that the patient warnings or alerts may follow an orthogonal path and are not described herein. The goal of the present embodiment is to delay, under certain circumstances, the triggering of the rapid shift detector motion recovery process. For example, such delay might comprise 15 seconds which, when added to the 5 seconds discussed above with respect to FIGS. 7a-7c, produces a 20-second total delay. After 20 seconds of no pulse pressure, the rapid shift detector object 830 will trigger motion recovery automatically. During intervening "check" intervals (e.g., 5-seconds each), tonometric pressure (average of two-second intervals) is compared with the diastolic, mean and systolic pressures to determine if the system should enter motion recovery prior to the expiration of 20 seconds. Exemplary conditions for entering the rapid shift detector motion recovery process at each of the 5-second check intervals is set forth in Table 4, although it will be appreciated that other criteria, whether alone or in combination with those of Table 4, may be utilized with equal success.

TABLE 4

| Criterion | Elapsed Time Since Last Beat (seconds) | | | |
|---|---|---|---|---|
| | 5 | 10 | 15 | 20 |
| | Enter motion recovery? | | | |
| Automatic mini-sweep initiated | No | No | No | Yes |
| First process ("thump and bump") event | Yes | Yes | Yes | N/A |
| 2-sec. block avg. pressure > systolic pressure (current median filtered) | Yes | Yes | Yes | N/A |
| 2-sec. block avg. pressure > mean pressure (current median filtered); -or- 2-sec. block avg. pressure > 2-sec. block avg. pressure from 5 sec. Past | No | Yes | Yes | N/A |
| 2-sec. block avg. pressure > maximum diastolic pressure (current median filtered); -or- 2-sec. block avg. pressure > 2-sec. block avg. pressure from 5 sec. Past | No | No | Yes | N/A |
| 2-sec. block avg. pressure < diastolic pressure (current median filtered) minues 25 mmHg | Yes | Yes | Yes | N/A |
| 2 sec blcok avg. pressure < 30 mmHg | Yes | Yes | Yes | N/A |

Note that the direction of the recovery mini-sweeps are mapped to the triggering criteria described in the table above. For the trigger conditions within the table, those at the 5-second and 15-second points should be mapped to an initial mini-sweep wherein applanation (compression) increases. The other motion recovery triggers are mapped to an initial mini-sweep wherein the sensor is retracted from the blood vessel.

Furthermore, needless and unwanted mini-sweeps that extend significantly beyond preexisting systolic pressure upwards to the preset maximum turnaround (280 mmHg in the exemplary configuration) should be avoided. During this upward search, a condition statement to terminate (or change sweep direction) is utilized. The following exemplary code implements this functionality. Note that in the present embodiment, this code is called only when a new beat is detected.

```
if((((AppMotorTach.lGetParameter( ) – MIN_COUNT_FROM_END_OF_TRAVEL < –
lGetMaxTravelAllowed(APPLANATION_CONTROL))
    ||(dGetApplanationServoPressure( ) > MAX_PRESSURE_FOR_TURN_AROUND))
    ||( ( (dMaxPulsePressure * .90 > dAvgPulse)&&(dMaxPulsePressure – dAvgPulse > 5. )&&
(dAvgMean >        pApplanationThumpAndBump->fGetGoalMean( ))&& (iArrayPointer > 8) ))
)
    ||((((dMaxPulsePressure * .80 > dAvgPulse) && dMaxPulsePressure – dAvgPulse > 5.) &&
(iFirstPass) && (iArrayPointer > 8) ))))
```

©Copyright 2003 Tensys Medical, Inc. All rights reserved. To the foregoing condition statement (code), an a conditional statement (logical "OR") may be added, such that:

IF either (i) no pulse has been observed for the last X seconds (e.g., 3 seconds), OR (ii) the pulse pressure for the observed pulses was less than 5 mmHg;
AND
the two second average pressure exceeds the last "good" systolic pressure by 40 mmHg;
THEN
the current upward (i.e., increasing compression) mini-sweep should (i) terminate, OR (ii) change direction.

In addition, the "IF" statement in the example above is preceded by a condition statement that permits mini-sweep termination or direction change??? only when a new beat is detected (condition precedent). To this condition precedent, a second condition precedent may be added checking whether no beat has been detected for the last Y (e.g., three) seconds, as exemplified in the following code:

```
else if (bTLineBeatHappened)
{
    App.logMsg("AS_STATE_THUMP_BUMP-->NewBeatDetected\n");
```

© Copyright 2003 Tensys Medical, Inc. All rights reserved. In yet another variant, an algorithm is implemented so as to "passively" detect cuff inflation onset via pressure wave parameters. This approach utilizes a series of special routines within the computer code including: (i) a curve fitting algorithm that models the aforementioned exponential decay of the tonometric pressure waveform during the continued cuff inflation; (ii) an algorithm for detection of the rise in diastolic pressure during the initial stages of cuff inflation; and (iii) an algorithm for evaluating a change in waveshape for the last beat prior to pulse cessation when compared to previous beats (the so-called "top hat" effect).

Such algorithms (i.e., curve-fitting, artifact detection, and wave shape analysis) are well known in the signal processing arts, and may be readily implemented within the present invention by those of ordinary skill provided the present disclosure. These algorithms, however, generally involve a restructuring of the system code to provide more extensive beat and waveshape information to support the required waveform analysis, and therefore should be optimized so as to minimize or avoid any deleterious effects on device timeline.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. Physiologic parameter measuring apparatus configured to mitigate effects of a first change in blood vessel dynamics, said apparatus comprising:
   a non-invasive parameter sensor configured to sense a parameter associated with a blood vessel at a first location on a body of a subject and generate a signal relating thereto;
   a processor operatively coupled to said sensor; and
   a computer program configured to be executed by said processor, said computer program comprising a plurality of instructions which are configured to, when executed:
   process said signal to produce a representation of said measured parameter;
   passively detect a second change within said signal resulting from said first change in said dynamics; and
   delay processing of said signal until said second change has substantially subsided.

2. The apparatus of claim 1, further comprising a mechanism coupled to said sensor and configured to move at least said sensor relative to said subject as said non-invasive parameter sensor senses said parameter.

3. The apparatus of claim 2, wherein said computer program is further configured to modulate a position of said sensor via said mechanism.

4. The apparatus of claim 2, wherein said second change comprises a change in mechanical coupling between said sensor and said subject so that an effective flow area of said blood vessel is altered.

5. The apparatus of claim 1, wherein said computer program further comprises:
   a physiologic parameter event detector; and
   an analytical routine; and
   wherein said event detector advises said analytical routine as to detected events within said signal, said routine configured to cause said signal to stop being processed when no events are detected within a first time interval.

6. A method of mitigating an effect of an alteration within physiologic parameter data obtained from a sensor applied to a living subject, said method comprising:
   analyzing said data, via a processor, to derive a substantially continuous representation of said physiologic parameter;
   detecting an event within said physiologic parameter within said signal;
   suspending said act of analyzing for a predetermined period based at least in part on said act of detecting said event;
   after expiration of said period, determining whether said event has terminated; and
   when said event has terminated, re-initiating said act of analyzing.

7. The method of claim 6, wherein said physiologic parameter data is obtained non-invasively from said subject using said sensor.

8. The method of claim 6, wherein said physiologic parameter data is obtained at least in part while said sensor is compressing tissue of said subject, and method further comprises changing a level of compression applied to said subject during said act of obtaining of said data during said event.

9. The method of claim 6, wherein said physiologic parameter data comprises pressure data obtained from said subject, and said act of detecting an event comprises detecting a reduction in a difference between systolic and diastolic pressures present in said data.

10. The method of claim 6, wherein said act of detecting an event comprises detecting a loss of one or more cardiac beats in said data.

11. Physiologic parameter measuring apparatus configured to mitigate an effect of an alteration, said apparatus comprising:

a sensor configured to sense a physiologic parameter at a first location on a body of a subject and generate a signal relating thereto;

a processor operatively coupled to said sensor; and a computer program configured to be executed by said processor, said computer program comprising a plurality of instructions which are configured to when executed:

analyze said signal to derive a continuous representation of said measured parameter;

detect a change within said signal resulting from said alteration;

based at least in part on said detected change, suspend said analysis for a predetermined period;

determine whether said event has terminated upon expiration of said period; and when said event has terminated, re-initiate said analysis.

12. The apparatus of claim 11, wherein said physiologic parameter signal is obtained non-invasively from said subject via said sensor.

* * * * *